US006599705B2

(12) United States Patent
Rupp et al.

(10) Patent No.: US 6,599,705 B2
(45) Date of Patent: Jul. 29, 2003

(54) REGULATION OF FUNGAL GENE EXPRESSION

(75) Inventors: Steffen Rupp, Stuttgart (DE); Laura Robertson, Cambridge, MA (US); Eric F. Summers, Jamaica Plain, MA (US); Peter Hecht, Newton, MA (US); Radclyffe Roberts, Seattle, WA (US); Hiten Madhani, Brookline, MA (US); Cora Ann Styles, Arlington, MA (US); Hsiu-Jung Lo, Taipei (TW); Amir Sherman, Boston, MA (US); Brian Cali, Somerville, MA (US); Gerald R. Fink, Chestnut Hill, MA (US)

(73) Assignee: The Whitehead Institute for Biomedical Research, Cambridge, MA (US)

( * ) Notice: Subject to any disclaimer, the term of this patent is extended or adjusted under 35 U.S.C. 154(b) by 35 days.

(21) Appl. No.: 09/863,040

(22) Filed: May 22, 2001

(65) Prior Publication Data

US 2002/0155517 A1 Oct. 24, 2002

Related U.S. Application Data

(62) Division of application No. 09/189,462, filed on Nov. 10, 1998, now Pat. No. 6,303,302.
(60) Provisional application No. 60/094,523, filed on Jul. 29, 1998, provisional application No. 60/078,610, filed on Mar. 19, 1998, provisional application No. 60/066,462, filed on Nov. 24, 1997, provisional application No. 60/066,308, filed on Nov. 21, 1997, and provisional application No. 60/066,129, filed on Nov. 19, 1997.

(51) Int. Cl.[7] ................................................ C12Q 1/68
(52) U.S. Cl. ........................... 435/6; 435/441; 435/446; 435/473
(58) Field of Search .......................... 435/6, 441, 446, 435/473

(56) References Cited

U.S. PATENT DOCUMENTS

| 5,024,941 A | 6/1991 | Maine et al. ............... 435/69.9 |
| 5,633,146 A | 5/1997 | Fleer et al. .................. 435/69.1 |
| 5,665,543 A | 9/1997 | Foulkes et al. ................. 435/6 |

FOREIGN PATENT DOCUMENTS

| WO | WO 94/26885 | 11/1994 |

OTHER PUBLICATIONS

Csank et al., "Roles of the *Candida albicans* mitogen–activated protein kinase homolog . . . " Infect. Immun. 66:2713–2721, 1998.

Denison et al., "Putative membrane components of signal transduction pathways . . . " Mol. Microbiol. 30:259–264, 1998.

Fujita et al., "Domains of the SFL1 protein of yeasts are homologous to Myc oncoproteins . . . " Gene 85:321–328, 1989.

Gimeno et al., "Inductin of pseudohyphal growth by overexpression of PHD1, . . . " Mol. Cell. Biol. 14:2100–2112, 1994.

Goldberg et al., "A *Candida albicans* homolog of CDC25 is functional in *Saccharomyces cerevisiae* . . . " Eur. J. Biochem. 213:195–204, 1993.

Goshorn et al., "Gene isolation by complementation in *Candida albicans* and applications . . . " Infect. Immun. 60:876–884, 1992.

Kartasheva et al., "Genetic aspects of carbon catabolite repression of the STA2 glucoamylase gene . . . " Yeast 12:1297–1300, 1996.

Kohler and Fink, "*Candida albicans* strains heterozygous and homozygous for mutations in . . . " Proc. Natl. Acad. Sci. USA 93:13223–13228, 1996.

Lambrechts et al., "Primary structure and regulation of a glucoamylease–encoding genet (STA2) . . . " Gene 100:95–103, 1991.

Lambrechts et al., "Multiple positive and negative cis–acting elements of the STA2 gene regulate . . . " Gene 146:137–144, 1994.

Lambrechts et al., "A multicopy suppressor gene, MSS10, restores STA2 expression in *Saccharomyces* . . . "Curr. Genet. 29:523–529, 1996.

Lambrechts et al., "The S1, S2 and SGA1 ancestral genes for the STA glucoamylase genes all map to . . . " Yeast 11:783–787, 1995.

Leberer et al., "Virulence and hyphal formation of *Candida albicans* require the Ste20p–like protein kinase CaCla4p" Curr. Biol. 7:539–546, 1997.

Leberer et al., "Signal transduction through homologs of the Ste20p and Ste7p protein kinase . . . " Proc. Natl. Acad. Sci. USA 93:13217–13222, 1996.

Li et al., "Proteolytic activation of Rim1p, a positive regulator of yeast sporulation and invasive growth" Genetics 145:63–73, 1997.

Liu et al., "*Saccharomyces cerevisiae* S288C has a mutation in FLO8, a gene required for filamentous growth" Genetics 144:967–978, 1996.

Liu et al., "Suppression of hyphal formation in *Candida albicans* by mutation of a STE12 homolog" Science 266:1723–1726, 1994.

Lo et al., "Nonfilamentous *C. albicans* mutants are avirulent" Cell 90:939–949, 1997.

Lo and Dranginis, "The cell surface flocculin Flo11 is required for pseudohyphae formation by . . . " Mol. Biol. Cell 9:161–171, 1998.

(List continued on next page.)

*Primary Examiner*—James Ketter
(74) *Attorney, Agent, or Firm*—Fish & Richardson P.C.

(57) ABSTRACT

Disclosed herein are methods for regulating fungal gene expression, and reagents for carrying out those methods.

16 Claims, 27 Drawing Sheets

OTHER PUBLICATIONS

Lo and Dranginis, "FLO11, a yeast gene related to the STA genes, encodes a novel cell surface flocculin" J. Bacteriol. 178:7144–7151, 1996.

Lo et al., "Development of pseudohyphae by embedded haploid and diploid yeast" Curr. Genet. 32:197–202, 1997.

Madhani et al., "The control of filamentous differentiation and virulence in fungi" Cell Biol. 8:348–353, 1998.

Mosch et al., "Dissection of filamentous growth by transposon mutagenesis in *Saccharomyces cerevisiae*" Genetics 15:671–684, 1997.

Orejas et al., "Activation of the Aspergillus PacC transcription factor in response to alkaline ambient . . . " Genes Dev. 9:1622–1632, 1995.

Perez–Esteban et al., "Molecular characterization of fungal secondary metabolism promoter . . . " Mol. Microbiol. 9:881–895, 1993.

Roberts et al. "Elements of a single MAP kinase cascade in *Saccharomyces cerevisiae* mediate two . . . " Genes Dev. 8:2974–2985, 1994.

Rosenbluh et al., "Isolation of genes from *Candida albicans* by complementation in *Saccharomyces cerevisiae*" Mol. Gen. Genet. 200:500–502, 1985.

Stoldt et al., "Efg1p, an essential regulator of morphogenesis of the human pathogen *Candida albicans*, . . . " EMBO J. 16:1982–1991, 1997.

Su et al., "Identification of functionally related genes that stimulate early meiotic gene expression in yeast" Genetics 133:67–77, 1993.

Vivier et al., "Coregulatin of starch degradation and dimorphism in the yeast *Saccharomyces cerevisiae*" Crit. Rev. Biochem. Mol. Biol. 32:405–435, 1997.

Webber et al., "MSS1, a novel yeast gene involved in the regulation of starch metabolism" Curr. Genet. 32:260–266, 1997.

Xu and Hamer, "MAP kinase and camp signaling regulate infection structure formation and pathogenic growth . . . " Genes Dev. 10:2696–2706, 1996.

```
                        Dra I
SEQ ID NO 1             ─────
TTAAAAGTTTTTGATTGTTGAACTTTTTAAATTTTTCTTGGCAATCCATTCCCAGACAAAGTAATAACTACGAATAGAT
---+----+----+----+----+----+----+----+----+----+----+----+----+----+----+----+   80
AATTTTCAAAAACTAACAACTTGAAAAATTTAAAAAGAACCGTTAGGTAAGGGTCTGTTTCATTATTGATCCTTATCTA

HinD III
                                ───────
CATTCATTGGTTTATTATTTTTGCATGGAAATATTTGAATTTCCATTTTTTTTTTTTATAGTGGTTGTTAAGCTTCGCA
---+----+----+----+----+----+----+----+----+----+----+----+----+----+----+----+   160
GTAAGTAACCAAATAATAAAAACGTACCTTTATAAACTTAAAGGTAAAAAAAAAAAATATCACCAACAAATTCGAAGCGT

Ssp I
            ─────

GTTTTTTTTTCTAGGGAGAAATTATTATACATTATATATATATATATCAACTTTTTCTCGTTACAAAAGTCACACCTTT
---+----+----+----+----+----+----+----+----+----+----+----+----+----+----+----+   240
CAAAAAAAAAGATCCCTCTTTAATATATGTAATATATATATAATAGTTGAAAAGAGCAATGTTTTCAGTGTGGAAA

TTTTTTCTACTTGTTCTCTTCAACAACTAACTAATTTTATACTATCCACGAACTATAGATATTACATATAAGTTTTT
---+----+----+----+----+----+----+----+----+----+----+----+----+----+----+----+   320
AAAAAAGATGAACAAGAGAAAGTTGTTGATTGAATTAAAATATGATAGGTGCTTGATATCTATAATGTATATTCAAAAA

Age I
                                                        ─────
AACCTAGACAAACGAGATTTTTAGACAATGAATTACAACATTCATCCCGTAACATACTTAAATGCTGATAGCAATACCGG
---+----+----+----+----+----+----+----+----+----+----+----+----+----+----+----+   400
TTGGATCTGTTTGCTCTAAAAATCTGTTACTTAATGTTGTAAGTAGGGCATTGTATGAATTTACGACTATCGTTATGGCC

SEQ ID NO 2  M  N  Y  N  I  H  P  V  T  Y  L  N  A  D  S  N  T  G
             ↑START              ──Ca RIM1──────────────────────────

Fig. 5A-1
```

```
            Sca I            Nco I
TGCAAGTGAGAGTACTGCAAGTCACCATGGTTCCAAGAAATCACCTTCCTCAGATATTGATGTAGATAATGCTWCGTCAC    480
---+----+----+----+----+----+----+----+----+----+----+----+----+----+----+----
ACGTTCACTCTCATGACGTTCAGTGGTACCAAGGTTCTTTAGTGGAAGGAGTCTATAACTACATCTATTACGAWCAGTG

A  S  E  S  T  A  S  H  H  G  S  K  K  S  P  S  S  D  I  D  V  D  N  A  ?  S
                                     Ca RIM1

Vsp I
CTTCATCTTTTACTTCGTCCCAATCACCTCACATTAATGCTATGGGTAACAGTCCCCATTCCTCATTCACTTCTCAATCT    560
---+----+----+----+----+----+----+----+----+----+----+----+----+----+----+----
GAAGTAGAAAATGAAGCAGGGTTAGTGGAGTGTAATTACGATACCCATTGTCAGGGGTAAGGAGTAAGTGAAGAGTTAGA

P  S  S  F  T  S  S  Q  S  P  H  I  N  A  M  G  N  S  P  H  S  S  F  T  S  Q  S
                                               Ca RIM1

PstI                     Xcm I
GCAGCCAATTCTCCTATCACTGATGCCAAACAACATTGGTTAAACCAACCACCACCAAGCCAGCTTTTGCTCCTAG        640
---+----+----+----+----+----+----+----+----+----+----+----+----+----+----+----
CGTCGGTTAAGAGGATAGTGACTACGGTTTGTTGTAACCAATTTGGTTGGTGGTGGTTCGGTCGAAAACGAGGATC

A  A  N  S  P  I  T  D  A  K  Q  H  L  Y  K  P  T  T  T  K  P  A  A  F  A  P  S
                                               Ca RIM1
```

Fig. 5A-2

```
                                                                                  720
TGCTAATCAATCTAACACCACAGCTCCGCAATCTTATACCCAACCAGCACAACAATTACCAACTCAGTTACACCCAAGTC
----+----|----+----|----+----|----+----|----+----|----+----|----+----|----+----|
ACGATTAGTTAGATTGTGGTGTCGAGGCGTTAGAATATGGGTTGGTCGTGTTGTTAATGGTTGAGTCAATGTGGTTCAG
 A  N  Q  S  N  T  T  A  P  Q  S  Y  T  Q  P  A  Q  Q  L  P  T  Q  L  H  P  S
                           Ca RIM1
                                    Xcm I
                                    Van91 I                                   800
TTAACCAAGCCTACAACAACCAACCATCTTATTATTACACCAACCAACTTATGGCTACCAACAACAACAACAACAACAA
----+----|----+----|----+----|----+----|----+----|----+----|----+----|----+----|
AATTGGTTCGGATGTTGTTGGTTGGTAGAATAATAAATGTGGTTGAATACCGATGGTTGTTGTTGTTGTTGTTGTTGTT
 N  Q  A  Y  N  N  Q  P  S  Y  Y  L  H  Q  P  T  Y  G  Y  Q  Q  Q  Q  Q  Q  Q
                           Ca RIM1
                                                                              880
CAACACCAAGAGTTTAACCAACCAAGTCAACAACCATCACGACAATATACCACGGATACTACTCAAACAACAACATTTGAATCA
----+----|----+----|----+----|----+----|----+----|----+----|----+----|----+----|
GTTGTGGTTCTCAAATTGGTTGGTTCAGTTGTTGGTAGTGTCGTTATGGTGCCTATGATGAGTTTGTTGTTGTAAACTTAGT
 Q  H  Q  E  F  N  Q  P  S  Q  Q  Y  H  D  H  H  G  Y  Y  S  N  N  N  I  L  N  Q
                           Ca RIM1
                                                          Esp31               960
GAATCAACCAGCTCCCACAACAAATCCAGTCAAGCCATTCAAAAAGACATACAAGAAAATCAGAGACGAAGATTTGAAAG
----+----|----+----|----+----|----+----|----+----|----+----|----+----|----+----|
CTTAGTTGGTCGAGGGTGTTGTTTAGGTCAGTTCGGTAAGTTTTTCTGTATGTTCTTTTAGTCTCTGCTTCTAAACTTTC
 N  Q  P  A  P  Q  Q  N  P  V  K  P  F  K  K  T  Y  K  K  I  R  D  E  D  L  K
                           Ca RIM1
```

```
                                                                    Dra III
ACTTGCCATCTTATCCTCAAATCAACCGTCTCTTTGCCATATTCTTCTGGTGTGGCACAACAACCACCAAGTGCATTAGAG
---------+---------+---------+---------+---------+---------+---------+---------+   2000
TGAACGGTAGAATAGGAGTTTAGTTGGCAGAGAAACGGTATAAGAAGACCACACCGTGTTGTTGGTGGTTCACGTAATCTC

Y  L  P  S  Y  P  Q  I  N  R  S  L  P  Y  S  S  S  Y  A  Q  Q  P  P  S  A  L  E
                                         Ca RIM1

Bsg I                          Nde I             Bbs I              Eco57 I
                                                                              Bbs I
TTTGGCGGTGTGTTTCAACCTACCAGAAATCTGCACAATCATATGAAGAAGACAGCAGCGACAGTTCAGAGAAGACGATTA
---------+---------+---------+---------+---------+---------+---------+---------+   2080
AAACCGCCACACAAAGTTGGATGGTCTTTAGACGTGTTAGTATACTTCTTCTGTCGTCGCTGTCAAGTCTCTTCTGCTAAT

F  G  G  Y  S  T  Y  Q  K  S  A  Q  S  Y  E  E  D  S  S  D  S  S  E  E  D  D  Y
                                                             Ca RIM1

Bbs I                                    BspD I
                                                             Cla I
CAGCACTTCTTCAGAAGACGAGCTTGACACCTTGTTTGATAAATTAAACATGATGACAATAAAGTTGAAGAAGTGACGA
---------+---------+---------+---------+---------+---------+---------+---------+   2160
CTCGTGAAGAAGTCTTCTGCTCGAACTGTGGAACAAACTATTTAATTTGTAGCTACTGTTATTTCAACTTCTTCACTGCT

S  T  S  S  E  D  E  L  D  T  L  F  Q  K  L  N  I  D  D  N  K  V  E  E  Y  T
                                         Ca RIM1
```

Fig. 5A-8

```
                                                                    Xcm I
TTGATGGGTTCAATTTGAAGGATGTGCCAAGCACAGAGAAATGATCCATGCTGTTCTTGGCTATTTGAGAAACCAAATC
---+---+---+---+---+---+---+---+---+---+---+---+---+---+---+---+  2240
AACTACCCAAGTTAAACTTCCTACACGGTTCGTGTCTCTTTACTAGGTACGACAAGAACCGATAAACTCTTTGGTTTAG

I  D  G  F  N  L  K  D  V  A  K  H  R  E  M  I  H  A  V  L  G  Y  L  R  N  Q  I
                                           Ca RIM1

GAACAACAAGAAAAGAGCAAAGAGCAAAGGAGGTTGACGTTAATGAAACTAAATTATATCCAACTATAACTGC
---+---+---+---+---+---+---+---+---+---+---+---+---+---+---+---+  2320
CTTGTTGTTCTTTTCTCGTTTCTCGTTTCCTCCAACTGCAATTACTTTGATTTAATATAGGTTGATATTGACG

E  Q  Q  E  K  E  K  S  K  E  Q  K  E  V  D  V  N  E  T  K  L  Y  P  T  I  T  A
                                           Ca RIM1
            BspD I
            Cla I              Bcg I
TTTCTAAGCAATTATATCGATTTTACTTTTTTATTTATTTTATTTTTGTTTAGGGTGGTTTTCAATTTTTTTTTTT
---+---+---+---+---+---+---+---+---+---+---+---+---+---+---+---+  2400
AAAGATTCGTTAATATAGCTAAAATGAAAATAAAATAAAATAAAAACAAATCCCACCAAAAGTTAAAAAAAAAA

F
Ca RIM1 ▲
        STOP
```

Fig. 5A-9

```
                                                                          Eco57 I
ACTGCGTCAATTCCACAGTTTGTTTGAACAACTTGGGGTTATCGTGACCTTTAACTATGATGATTTGATTTTTCTCATAA
---+---!---+---!---+---!---+---!---+---!---+---!---+---!---+---!---+---!---+---!   2800
TGACGCAGTTAAGGTGTCAAACAAACTTGTTGAACCCCAATAGCACTGAAATTGATACTACTAAACTAAAAAGAGTATT

Sph I
TTCTTATCGCTGACAAACCAAATGCCTTGGTATTGTGGATCTCGTTGCGCATGCAAGATTTCTGGCCTATCGT
---+---!---+---!---+---!---+---!---+---!---+---!---+---!---+---!---+---!---+---!   2880
AAGAATAGCGACTGTTTGGTTTACGGAACCATAACACCTAGACGAACGCCGTACGTTCTAAAGACCGGATAGCA

BsrS I
Sph I                            Eco57 I
AGCATGCCATAGCCCCCTGTGTTGACCCCAAACCTTACCATCTCTCAGTGATTATGTCACCTGGGTTTTCTCGGATATAAT
---+---!---+---!---+---!---+---!---+---!---+---!---+---!---+---!---+---!---+---!   2960
TCGTACGGTATCGGGGACACAACTGGGGTTTGGAATGGTAGAAGTCACTAATACAGTGGACCCAAAAGACCCTATATTA

Dra I
CATTTAAAAACTCTCGGAAGTTTGACTGCTGCTGCGGATTAACAAAGCATAGCCCCTTGGGAGTCGGGTTTTGTGCTGTGT
---+---!---+---!---+---!---+---!---+---!---+---!---+---!---+---!---+---!---+---!   3040
GTAAATTTTTGAGAGCCTTCAAACTGACGACGCCTAATTGTTCGTATCGGGAACCCTCAGCCCAAAACAACGACACACA

Bal I
              MluN I
              Msc I
AATTTAAACTGGTCATGTGCCAATTCCCGAATCTGTGGTTTGATATAGTGGCCAATGGGTAATAAGATTTTCGATAACGA
---+---!---+---!---+---!---+---!---+---!---+---!---+---!---+---!---+---!---+---!   3120
TTAAATTTGACCAGTACACGGTTAAGGGCTTAGACACCAAACTATATCACCGGTTACCCATTATTCTAAAAGCTATTGCT

Dra I
```

Fig. 5A-11

(SEQ ID NO:3)

```
CCCAGTTTCT CATAACCCGT CATTTGAGCG ATTGCTAGTT GAAACTATAT
ACAGCTAGTT AGTAAGATTT TAAAAGACGA AAAGAACGGA AAGTAGGACA
ACTACCAAAA AAAAAGATGG AAGGTTTCTT TGGTTAGTTA GCAGTATCCG
CGTAATGCCT TAGACGTTTT TGATCAGAAA AAAATAAAAC TTGATTTCGC
CCAGGATCGA ACTGGGGACG TTCTGCGTGT TAAGCAGATG CCATAACCGA
CTAGACCACG AAACCAGTTT TTTGATGTTT CGTTTAGGAC AAGAGTCCTA
TGAGAGTCCA CTAAAATTCT AAAAATAATT GTATCAACAA CCGTCATGCA
GCTGTTGTAT CAAGAATCGA CCACCATCTA TAGACTATTG TTCATAGCTG
TATTACAATA TCATATAAGA TGTAAGGATA GAACGTGAAG ATCGAGAAAC
AGTCAGCAGA TTTAATGGAA GCTGAAATGC ACGGATTGAT AATGTAATAG
AATAAGTGAC AACATAAGAA ATGAAAGAAA AAAAATAACA TTAATATAAT
TTAGAAATGT TAGTTTCCTT CTATGAACTC TCGTATCCCT GGGGAGGACT
TTCAATATAT TCAGTATACC TACCGTTCAA ATGATACTCT AAAATATCAT
CTATTAAGTG GTATTCAGGT TTTTCCACG CAAGATTGAG TGCGTCAGGC
AAAGCCACGA TCGCAGATTA CTCTCCTAAC AATATTAAGA TCGTCAAGAA
CATCCGGTTT TACTCAAGCG CTTAATACAA CACGTCGGCT TTCGCTCAAC
TGCAGTATAT TGTGTCTGTA ACCTCTCCCG TCAAGTTTGC GCCACGGGCC
CAATAACCAA CTTCTGCGCC ATTGTTACGG AAAAGTGGCC ATCTTTGCTA
TGCTCGTAAG GCTAGCGCTC TCTAAGTACG CCAGCCCAAA AACTCCGTAT
CGCTCTTCAT CGGAATTGCT ATATCTACAG CCGGACGGGC ACTCTATGTA
TACTCATATC ACAGCCACTG TTGCACTACA TTATTCGCAG GGACTCCGAG
ATCGCTGAGC ATGTTGCTAA GCAACTTACC AAGGTTGGAA TGCATTATAT
AGTCCGATAT AGACCCCGCT CGGACTATAT TATATAAATT CAAATAGCAC
TTTCAACGAG TGTCTTAATC CGTCCTAGTT CCTGCTCTCG CTCCACGTTG
TCATCCCACC CATTCGCACG GGTCTTCTGT GCGAATGAGC CACAACGGGG
CCGAGTTCAG GCCGTGTCCG CCTACAACGT CCGCCAACTA GTGGCAATTG
CTACGTACGC CGACCACGCT GACACGCACC GTTCTACTCG CTCTATGCTG
CGGTGTGACG TGTGAACGCG CGATCGTTCG CAATCGTATC GTTTGCCAAG
AAAAAAAGCC AATCGGAGAA TCTGAAAATC GCTATTCGGC TTGCAGGTCG
CACGCACTCA GAGTACGAAA TGCCAAGTAC CGGAATTTCC TTGGCCTTTT
TTAAGTTTCT TCTCTTCTAT TCTTTTTCCC CTTTCTTTCT TCCTTTGCTA
TCTGTCTGGT TTAAATAAAC ATAGTATTTT TTTGTGTCTA AGCCTCTTCC
TCTTCTCTCG TACTTGCTCT ACTACCACTT TACTTAATCG CCTTTCTTTG
TTTTCTTTCT TCGTTATTTG TTCTTGGAAC TTTTCCGCTC CAATCCCAAC
GATTGGCTTC AAAACACGTT CTACTGTCTA GCAATTTCTG CAGGTGCCAT
TTTTCTTAGG CTTATACCCT TTCCTTTTCC CCTTACATTT GATTTCTTCT
TCAAAGTTCC TTATAGTATT ATTGTCTAAG CTCTATTGAG TCAAAAGTAA
CAATCTAGAC GAAGGAAAAA AAAAAATAG AAAATAGACA TCCCCGAATA
CGCATCATCT CACGCACGTA CAAGATTTTA ACGTTAAAGC CAAAGTACGC
TAGTATAGTA TCATCAGCAT CACCCTCACT ATCGGTAGCA TTGACCAAAC
ATGTCGTTAC TGAGACTGTG GAACAAAGAA TCAAGGGCAC CATCAAAAAT
```

Fig. 6A-1

```
AAAGAGTCAT GGTATTGTTG GCAGTTACGG CAACAGCATG CTGGCCCATA
ACAACGTGAA GCAATTTCGT ATAGACATAG ACGAACCGCA TAGAGTATGG
AAACCGAATG AAAGCATAAC CGGAGAAGCG GTCATTGACA TAAAGAGAGA
CATAACTAAC GTAGCGATCA AATTATCGCT AGTATGTGAG GTTCGCGTGA
AAACGGGGAA CAGTCCAACC TCCAAGAATA AGAGAATTGA GAAAACCTTA
GAGAAGTCGA CGTTTCTTTA TGGACAGGAC TACGTAAAGA CAGCTTTTTC
GGCTAAGGAA AAGAAACCGC ATGTTGACAA AACCACCATT CTCAATGGTT
TAAGCAAGGG GGAACACAGG TTTCCCTTTA GGATACGAAT ACCACGAGGC
AGAGGAATGT TGAGCTCTAT AAAGTTCGAA AGGGGCTCGA TAACATACTT
CCTCTCTTGC ACTTTAGAAT CCCTCAACAA CATCAACGGA TTAAAAAAAC
CGGAAGCAAG ATGCGAACGT GAGTTTGCAG TCATAGTTCC GCTGGACGTC
TCGAGGCTGC CCAAGCCGAA AACTAAGACA GTGGTTTTAC AATCAGCATC
TATGGTCCAA AACAAAAGA ACAAATCTAC AGAGGACGAA TCCTCATCGT
ATACACAATT AACTCAAAAG TCTACTACTT CTAATTCTTC TAGCAGTTCA
GTAAACTCCA AGACGTCCCC CTTACCAAAT AAAACGGTGA CTATATCCGT
AGACATACCG CAGGCTGGAT TCATGATTGG TGAAATTATC CCTATAGACG
TTAAGATTGA CCACTATAAG CCTTTCTATG CCCCTGCGGG TCTCACCACC
ACTTTGGTGA GGATATGTAG GGTGGGCGGT GCAGGCAAAG ATGATCCTAT
GGAGACTTTC AGAAAGATA TATGTCAGAG TATCTCTCCT ATATATATTA
ACCCTGAAAC GTTGCAGTTT CAATCTAGAG TTTATCTGAA AGTGCCCCTT
GATGCATTTT CGACCCTTAC TACTGTGGGA AAATTTTTCT CCTTCCAATA
CTATATCGAG GTTATGGTTA ACTTATCAAA AAAAAACGTG GTTTACACAG
AATCTAATAG AATAATAGGA ACTCCTATTG GAGAACAAAA TGGCTTGGGC
GTAGAGAATA ATATCAACCG TATCCAAGG AAAATGCTAC GTATGGTCAA
TCCAGAAACG TTGGAGAACG ATTCTGAGGG TTATGAATCC AGTATATTTT
TCAAAGATAT GGTAAATGTG GAAAAGCTAA AGAGACTGAG GAATGTAACT
GGTATGTCCA TAGAAACCGT CATAGGAACG ACGAGATCCG AACAGCAGCA
ATCTGATGCA AGCATCCCAT CCCAATCCTC AATCACGGCT CCTCAAAATT
CTCCATCGAA TTTAAGAGAT TGGTTGGCCC CATTAAATGC ATATGATAGT
GACGATGTTC CAGTTCCAAA GTATTCGCCA AATGATAAAG TCAGTGTACC
GTCGGAAGAC AAACAAGAAC TTGAACAAAA AAGACTACAA CAGTTAGAAA
GCGATCCTCC CCCTTGTGAT GACTATTAAA AAGTGCAGGT AACAAGTCAT
ATACTCGCAG CTTGCGCCGT GTTGGAACTA GGCGCCTTAA TCATGTTTGC
ATATTCCAC TATCCCAGCC ACGTAATGAT CCATGACATT AACATAGAAA
AAAAAAATCG AAGCATGCAC AAACCTGAGA TTTATATATG TTCATGTGTA
CTTAATATAC GTTTAATGAT TAAAACTATA GCCGTCCTCA GGCAAACTGA
GATAAGAAAC GAAAAATAG CAGTAACGTA AACGTTATTC TATATTTATA
AAGACGTCAA AAAAAAAGT GATTGTGATA TTGAGATGTA AGCTATATAC
CGAACTTTGA GCTCCCTCAC GTGGAAAATA TGATAGATTG TTGCCTCATC
ATTGCGGAAC CGCATTTTTT TTTGTATTT TTGCCTCCCT AGTTTCAAAA
TGCACCAAAT TCTCCCCTTA ATGCTTTTG TTTAAGTCC CAAATAGCCA
TCCTTTCATC ATCGGGCAAG ATAGAAATTT GACTGTCATT CAGTTGTAAC
ACCTGTTTCA GTAGTTCTTT CTGTTTGTTA AGCACAGCTG GATCCACCAC
```

Fig. 6A-2

```
CTCGTTCACG CTATTGTTAT TCGTAGCCGA TGCCTCTTCT TGCGGCCTGG
AAGCTAACGG GATCAAATCA TCCACTTTAC ATATCCCATT CGTTAGCAAT
AATTCAGCCG TAACAAAACT CAACTGTGGA CACAGCTCTA ATAGCGAAAC
AGCATCTTCA GGATGCGCTC TTGTCCATTC TTGGAATTTT TGTAAAAATT
TCAACTGCAC CTCTTTCGGT TTTTAGCTA GTTCGCTCGA TATCATCATA
GCAGGGGTGG TCATGTTTAT GTTAACGTCG ATACCAGAGG GCAATTCTGG
AAACTTTTGA CTTAGAAAAT TGGCATTTCC GCTGTTTTGA AAGTCCGGCC
CATTACTATT ATTATTATTA TTTCCATTGT TGTTATTGTT CCCATTAATG
TTGTTGTACT GTTGTTGTTG CTGTTGTGAA ACTCCCGATA TATCACTATT
GCTGGAGTAA CCGCATTTCA AAAACCTAGA GCCTAATTGG TATCCATTCA
AATTACGTAC TGCGCTGGCA CTGGACTCTA AATCTCTAAA TTCAATAAAC
GCGTACCCTT TCGACCTACC AGTTGGGGG TCGAACATCA TT
```

Fig. 6A-3

(SEQ ID NO:4)
MSLLRLWNKESRAPSKIKSHGIVGSYGNSMLAHNNVKQFRIDIDEPHRVW
KPNESITGEAVIDIKRDITNVAIKLSLVCEVRVKTGNSPTSKNKRIEKTL
EKSTFLYGQDYVKTAFSAKEKKPHVDKTTILNGLSKGEHRFPFRIRIPRG
RGMLSSIKFERGSITYFLSCTLESLNNINGLKKPEARCEREFAVIVPLDV
SRLPKPKTKTVVLQSASMVQNKKNKSTEDESSSYTQLTQKSTTSNSSSSS
VNSKTSPLPNKTVTISVDIPQAGFMIGEIIPIDVKIDHYKPFYAPAGLTT
TLVRICRVGGAGKDDPMETFRKDICQSISPIYINPETLQFQSRVYLKVPL
DAFSTLTTVGKFFSFQYYIEVMVNLSKKNVVYTESNRIIGTPIGEQNGLG
VENNINRIQRKMLRMVNPETLENDSEGYESSIFFKDMVNVEKLKRLRNVT
GMSIETVIGTTRSEQQQSDASIPSQSSITAPQNSPSNLRDWLAPLNAYDS
DDVPVPKYSPNDKVSVPSEDKQELEQKRLQQLESDPPPCDDY

Fig. 6B

REGULATION OF FUNGAL GENE EXPRESSION

CROSS REFERENCE TO RELATED APPLICATIONS

This application is a divisional of Ser. NO. 09/189,462 filed Nov. 10, 1998 now U.S. Pat. No. 6,303,302, which claims benefit from provisional applications "Fungal Switching" (U.S. Ser. No. 60/066,129), "*Candida albicans* RIM1 Gene is Essential for Invasive Hyphal Growth" (U.S. Ser. No. 60/066,308), "*Candida albicans* RIM1 Gene is Essential for Invasive Hyphal Growth" (U.S. Ser. No. 60/066,462), "Novel Screens and Selections Based on Fungal Invasion: Tools for New Drug Discovery" (U.S. Ser. No. 60/078,610), and "Fungal-Specific AFL1 Gene and its Function in Antifungal Drug Screening and in the Enhancement of Fungal Product Expression" (U.S. Ser. No. 60/094,523), which were filed on Nov. 19, 1997, Nov. 21, 1997, Nov. 24, 1997, Mar. 19, 1998, and Jul. 29, 1998, respectively.

STATEMENT AS TO FEDERALLY SPONSORED RESEARCH

The invention was supported, in whole or in part, by funding from the Government. The Government has certain rights in the invention.

BACKGROUND OF THE INVENTION

The present invention relates to methods of identifying and isolating genes which are involved in the regulation of fungal gene expression. The invention also relates to methods useful for identifying fungal virulence factors. It further relates to a method of identifying agents which increase or decrease the expression or activity of a gene that regulates or is required for fungal pathogenesis. The invention also relates to the use of such agents as fungicides or fungistats.

Fungi are a large and diverse group of organisms with enormous importance to humans. Pathogenic fungi are a significant cause of human disease, particularly in the rapidly increasing proportion of the population whose immune system has been compromised by disease, chemotherapy, or immunosuppressive drugs. A wide variety of plant-pathogenic fungi (e.g., blights, rusts, molds, smuts, mildews) cause huge food crop loss and damage to ornamental plants. Plant diseases are caused by a myriad of invasive fungal pathogens falling into many genera, for example: soft rot (e.g., Rhizopus), leaf curl (e.g., Taphrina), powdery mildew (e.g., Sphaerotheca), leaf spots (e.g., Fulvia), blight (e.g., Alternaria), blast (e.g., Magnaporthe), black rot (e.g., Guignardia), scab (e.g., Venturia), wilts (e.g., Fusarium), rusts (e.g., Puccinia), smuts (e.g., Ustilago), and cankers (e.g., Rhizoctonia). In addition, fungal species are the commercial source of a great many medicinally useful products, such as antibiotics (e.g., beta-lactam antibiotics such as penicillin, cephalosporin, and their derivatives), anti-hypercholesterolemic agents (e.g., lovastatin and compactin), immunosuppressives (e.g., cyclosporin), and antifungal drugs (e.g., pneumocandin and echinocandin). All of these drugs are fungal secondary metabolites, small secreted molecules that fungi utilize against competitors in their microbial environment. Finally, fungi also produce commercially important enzymes (e.g., cellulases, proteases, and lipases) as well as other products (e.g., citric acid, gibberellic acid, natural pigments, and flavorings).

The specifics by which fungi invade their growth substrate are not understood in detail. However, two important themes regarding the fungal invasion process have emerged in recent years. First, important human fungal pathogens, such as Candida sp., Aspergillus sp., Mucor sp., Rhizopus sp., Fusarium sp, *Penicillium marneffei,* Microsporum sp. and Trichophyton sp. invade through host tissues as filamentous hyphae. The virulence of *Candida (C.) albicans* has been shown to be dependent upon invasion of host tissues; mutations in any of several genes required for invasive growth substantially reduce virulence in a mouse model of systemic infection. Pathogenesis of the plant fungal pathogen *Ustilago (U.) maydis* also requires invasion. Second, there is a correlation between genes that regulate agar invasion in *Saccharomyces (S.) cerevisiae* and genes that control invasion in pathogenic yeast. As *S. cerevisiae* is amenable to genetic studies, it can be utilized to molecularly dissect the genetics of fungal invasion.

Homologs of certain *S. cerevisiae* genes required for invasion also regulate the production of secondary metabolites and secreted catabolic enzymes in other fungi. For example, activating mutations in Aspergillus homologs of the *S. cerevisiae* INV genes cause increased production of the secondary metabolite penicillin and a secreted alkaline phosphatase (Orejas et al., Genes Dev. 1995, 9:1622).

SUMMARY OF THE INVENTION

In one aspect, the invention features a method for determining whether a candidate compound decreases the expression of a gene operably linked to a fungal invasin gene promoter. The method generally includes the steps of (a) providing a fungus expressing the gene operably linked to a fungal invasin gene promoter; (b) contacting the fungus with the candidate compound; and (c) detecting or measuring expression of the gene following contact of the fungus with the candidate compound. In preferred embodiments, the fungus is a wild-type strain (e.g., *Saccharomyces cerevisiae, Candida albicans,* or *Aspergillus nidulans*); a mutant strain; or a transgenic fungus. In other preferred embodiments, the gene used in the method of the invention is a fungal invasin gene. Exemplary fungal invasin genes include, without limitation, AFL1, DHH1, INV1, INV5, INV6, INV7, INV8, INV9, INV10, INV11, INV12, INV13, INV14, INV15, BEM2, CDC25, FLO11, IRA1, MCM1, MGA1, MUC1, PET9, PHD2, PHO23, PTC1, RIM15, SFL1, SRB11, SSD1, STE21, STP22, SWI4, TPK2, TPK3, RIM1, or YPR1.

In still other preferred embodiments, the gene used in the method of the invention is a reporter gene. Exemplary reporter genes useful in the methods of the invention include, without limitation, chloramphenicol transacetylase (CAT), green fluorescent protein (GFP), β-galactosidase (lacZ), luciferase, URA3, or HIS3.

In preferred embodiments, the fungal invasin gene promoter utilized in the methods of the invention is derived from the FLO11, MUC1, STA1, ST2, or STA3 gene promoter. In other preferred embodiments, the fungal invasin gene promoter includes a promoter sequence derived from an AFL1, DHH1, INV1, INV5, INV6, INV7, INV8, INV9, INV10, INV11, INV12, INV13, RIM1, INV14, INV15, BEM2, CDC25, HOG1, IRA1, MCM1, MGA1, PET9, PHD2, PHO23, PTC1, RIM15, SFL1, SRB11, SSD1, STE21, STP22, SWI4, TPK2, TPK3, or YPR1 gene promoter. Preferably, the fungal invasin gene promoter is a fragment or a deletion of the fungal invasin gene promoter (e.g., a fragment of the FLO11 gene promoter); and, if desired, the fragment is fused to a basal promoter (e.g., a basal promoter from a PGK1, ADH1, GAL1-10, tet-R, MET25, CYC1 or CUP1 gene).

Typically, the expression of the gene (e.g., the endogenous FLO11 or a recombinant reporter gene expressed under the control of the FLO11 gene promoter or fragment thereof) is measured by assaying the RNA or protein levels or both of the expressed gene. For example, the polypeptide expressed by the fungal invasin gene or by the reporter gene produces a detectable signal under conditions such that the compound causes a measurable signal to be produced. Quantitatively determining the amount of signal produced requires comparing the amount of signal produced to the amount of signal detected in the absence of any compound being tested or upon contacting the cell with any other compound as is described herein. The comparison permits the identification of the compound as one which causes a change in the detectable signal produced by the expressed gene (e.g., at the RNA or protein level) and thus identifies a compound that is capable of inhibiting fungal invasion. A decrease in the expression of the fungal invasin gene is generally accompanied by an inhibition of fungal invasion or an inhibition of the developmental switch from yeast form to pseudohyphal growth or both.

In related aspects, the invention also features a method for determining whether a candidate compound increases the expression of a gene operably linked to a fungal invasin gene promoter. The method generally includes the steps of (a) providing a fungus expressing the gene operably linked to a fungal invasin gene promoter; (b) contacting the fungus with the candidate compound; and (c) detecting or measuring expression of the gene following contact of the fungus with the candidate compound. In preferred embodiments, the method further includes determining whether the candidate compound increases the production of a secondary metabolite in the fungus.

In another aspect, the invention features a method for determining whether a candidate compound inhibits fungal invasion. The method generally includes the steps of (a) contacting a fungus with a candidate compound under conditions suitable for invasion and (b) measuring or detecting invasion by the fungus following contact with the candidate compound. In preferred embodiments, the fungus is *Candida albicans* or *Saccharomyces cerevisiae*.

In another aspect, the invention features a method for determining whether a candidate compound promotes fungal invasion. The method generally includes the steps of (a) contacting a fungus with a candidate compound under conditions suitable for invasion and (b) measuring or detecting invasion by the fungus following contact with the candidate compound. In preferred embodiments, the fungus is *Candida albicans, Saccharomyces cerevisiae,* or *Aspergillus nidulans*.

In still another aspect, the invention features a method for identifying a fungal invasion-promoting gene. The method generally includes the steps of (a) expressing in a fungus (i) a first gene operably linked to a fungal invasin gene promoter and (ii) a second candidate gene or fragment thereof and (b) monitoring the expression of the first gene, wherein an increase in the expression of the first gene identifies the second candidate gene as a fungal invasion-promoting gene. In preferred embodiments, the fungus is a wild-type strain (e.g., *Saccharomyces cerevisiae, Aspergillus nidulans, Penicillium chrysogenum,* or *Acremonium chrysogenum*); is a mutant strain; or is a transgenic fungus.

Preferably, the first gene includes a fungal invasin gene (e.g., FLO11 or MUC1). In yet other preferred embodiments, the first gene includes a fungal invasin gene derived from AFL1, DHH1, INV1, INV5, INV6, INV7, INV8, INV9, INV10, INV11, INV12, INV13, INV14, INV15, BEM2, CDC25, HOG1, IRA1, RIM1, MCM1, MGA1, PET9, PHD2, PHO23, PTC1, RIM15, SFL1, SRB11, SSD1, STE21, STP22, SWI4, TPK2, TPK3, or YPR1 gene; or the first gene includes a reporter gene (e.g., lacZ URA3, or HIS3).

In preferred embodiments, the fungal invasin gene promoter is derived from the FLO11, MUC1, STA1, STA2, or STA3 gene promoter. In other preferred embodiments, the fungal invasin gene promoter is derived from the AFL1, DHH1, INV1, RIM1, INV5, INV6, INV7, INV8, INV9, INV10, INV11, INV12, INV13, INV14, INV 15, BEM2, CDC25, HOG1, IRA1, MCM1, MGA1, PET9, PHD2, PHO23, PTC1, RIM15, SFL1, SRB11, SSD1, STE21, STP22, SWI4, TPK2, TPK3, or YPR1 gene promoter; or is a fragment or a deletion of the above-mentioned fungal invasin gene promoters. Preferably, the fragment of a fungal invasin gene promoter is fused to a basal promoter (e.g., a basal promoter of a PGK1, ADH1, GAL1-10, tet-R, MET25, CYC1, or CUP1 gene).

Preferably, the expression of the gene utilized in the method of the invention is measured by assaying the protein level of the expressed first gene or by assaying the RNA level of the expressed first gene.

In related aspects, the invention also features a method for identifying a fungal invasion-inhibiting gene. The method generally includes the steps of (a) expressing in a fungus (i) a first gene operably linked to a fungal invasin gene promoter and (ii) a second candidate gene or fragment thereof and (b) monitoring the expression of the first gene, wherein a decrease in the expression of the first gene identifies the second candidate gene as a fungal invasion-inhibiting gene.

In yet another aspect, the invention features a method for increasing production of a secondary metabolite in a fungal cell; the method generally includes the step of contacting the fungal cell with a fungal invasion-promoting compound and culturing the cells under conditions which promote the increased synthesis of a secondary metabolite.

In another aspect, the invention features a method for increasing production of a secondary metabolite in a fungal cell. The method generally includes the step of decreasing the expression of a fungal invasion-inhibiting gene. In preferred embodiments, the decreased expression of the fungal invasion-inhibiting gene (e.g., HOG1, BEM2, RIM15, SFL1, IRA1, SSD1, SRB11, SWI4, or TPK3) results from an inactivation of the fungal invasion-inhibiting gene. In other preferred embodiments, the increased production of a secondary metabolite results from the expression of a mutated fungal invasion-inhibiting gene.

In still another aspect, the invention features a method for increasing production of a fungal secondary metabolite. The method generally includes the step of increasing the expression of a fungal invasion-promoting gene. In preferred embodiments, the fungal invasion-promoting gene is AFL1, DHH1, INV7, INV8, STE21, PET9, MEP2, INV1, INV5, INV6, INV9, INV10, INV11, INV12, INV13, INV14, INV15, CDC25, MCM1, MGA1, PHD2, PHO23, PTC1, RIM1, STP22, TPK2, or YPR1. In other preferred embodiments, the increased expression of the fungal invasion-promoting gene is achieved by constitutively expressing the fungal invasion-promoting gene or by overexpressing such a gene. In yet other preferred embodiments, the fungal invasion-promoting gene is mutated.

In another aspect, the invention features a method for increasing production of a fungal secondary metabolite. The method generally includes the step of expressing a gene or fragment thereof that encodes an activated form of a invasion-promoting polypeptide. In preferred embodiments, the activated form of the invasion-promoting polypeptide includes a fusion between the invasion-promoting polypeptide and a second polypeptide that further enhances the activity of the invasion-promoting polypeptide. In other preferred embodiments, the gene has a mutation.

In another aspect, the invention features a method for increasing production of a secondary metabolite in a fungal cell. The method generally includes the step of decreasing the activity of a fungal invasion-inhibiting polypeptide. In preferred embodiments, the fungal invasion-inhibiting polypeptide has a mutation (e.g., a dominant-inactive polypeptide). In other preferred embodiments, the fungal invasion-inhibiting polypeptide is Hog1, Bem2, Rim15, Ira1, Sfl1, Ssd1, Srb11, Swi4, or Tpk3.

In another aspect, the invention features a method for increasing production of a fungal secondary metabolite. The method generally includes the steps of increasing the activity of a fungal invasion-promoting polypeptide. In preferred embodiments, the fungal invasion-promoting polypeptide has a mutation (e.g., a dominant-active polypeptide). In other preferred embodiments, the fungal invasion-promoting polypeptide is Afl1, Dhh1, Inv1, Inv5, Inv6, Inv9, Inv10, Inv11, Inv12, Inv13, Inv14, Rim1,Inv15, Cdc25, Inv7, Mcm1, Mga1, Phd2, Pho23, Ptc1, Inv8, Ste2, Pet9, Mep2, Stp22, Ypr1.

In another aspect, the invention features a method of isolating a fungal invasin gene. The method generally involves the steps of (a) providing a fungus expressing a gene operably linked to a fungal invasin gene promoter; (b) mutagenizing the fungus; (c) measuring expression of the gene, wherein an increase or decrease in the expression of said gene identifies a mutation in said invasin gene; and (d) using said mutation as a marker for isolating said invasin gene. In preferred embodiments, the fungus is a wild-type strain (e.g., *Saccharomyces cerevisiae*) or is a mutant strain. In preferred embodiments, the gene utilized in the method includes a fungal invasin gene (e.g., FLO11, MUC1, AFL1, DHH1, INV1, INV5, INV6, INV7, INV8, INV9, INV10, INV11, INV12, INV13, INV14, INV15, BEM2, CDC25, HOG1, IRA1, MCM1, MGA1, PET9, PHD2, PHO23, RIM1, PTC1, RIM15, SFL1, SRB11, SSD1, STE21, STP22, SWI4, TPK2, TPK3, or YPR1). In other preferred embodiments, the gene includes a reporter gene (e.g., lacZ, URA3, or HIS3). In still other preferred, the fungal invasin gene promoter is from FLO11, MUC1, STA1, STA2, or STA3 gene promoter; or is from the AFL1, DHH1, INV1, INV5, INV6, INV7, INV8, INV9, INV10, INV11, INV12, INV13, INV14, INV15, BEM2, CDC25, RIM1, HOG1, IRA1, MCM1, MGA1, PET9, PHD2, PHO23, PTC1, RIM15, SFL1, SRB11, SSD1, STE21, STP22, SWI4, TPK2, TPK3, or YPR1 gene promoter. In other preferred embodiments, the fungal invasin promoter is a fragment or deletion of the above-mentioned fungal invasin gene promoters. Preferably, the fragment of a fungal invasin gene promoter is fused to a basal promoter (e.g., a basal promoter of a PGK1, ADH1, GAL1-10, tet-R, MET25, CYC1 or CUP1 gene).

In another aspect, the invention features a method of using a cell (e.g., a fungal cell) for identifying a gene which regulates the expression from a *Candida albicans* gene promoter. The method generally includes the steps of (a) providing a cell expressing a reporter gene operably linked to a *Candida albicans* gene promoter; (b) expressing a candidate gene in the cell; and (c) detecting or measuring the expression of the reporter gene. In preferred embodiments, the fungal cell is *Saccharomyces cerevisiae*.

In another aspect, the invention features a method for preparing a transgenic fungal cell having increased secondary metabolite production. The method generally includes the steps of (a) introducing a transgene (e.g., a transgene encoding an invasin gene such AFL1, DHH1, INV7, INV8, STE21, PET9, MEP2, INV1, INV5, INV6, INV9, INV10, INV11, RIM1, INV12, INV13, INV14, INV15, CDC25, MCM1, MGA1, PHD2, PHO23, PTC1, STP22, TPK2, YPR1 or a fragment thereof, which is positioned for expression in a fungal cell) and (b) selecting a cell that expresses the transgene. In preferred embodiments, the transgene has a mutation (e.g., a dominant-active mutation or a dominant-inactive mutation).

In another aspect, the invention features a method for increasing a secondary metabolite in a fungus. The method generally includes the steps of (a) culturing the fungus in culture with conditions allowing for secondary metabolite production; (b) adding to the culture a fungal invasion-promoting compound; and (c) isolating the metabolite from the culture. In preferred embodiments, the fungus has a mutation. In other preferred embodiments, the fungus is a wild-type strain.

In still another aspect, the invention features a transgenic fungus (e.g., a filamentous fungus) which includes a mutation in an invasin gene that inhibits its activity. Preferably, the invention features a transgenic filamentous fungus having a mutation in a HOG1, SWI4, BEM2, SRB11, SSD1, TPK3, SFL1, or an IRA1 gene or any combination thereof. Preferably, such mutations inhibit the activity of the expressed protein (e.g., Hog1, Swi4, Bem2, Srb 11, Ssd1, Tpk3, Sfl1, or Ira1 or any combination thereof). In other preferred embodiments, the transgenic fungus has increase secondary metabolite production (e.g., increased production of antibiotics).

In another aspect, the invention features a substantially pure Inv9 polypeptide. Preferably, the Inv9 polypeptide is at least 55% identical to the amino acid sequence of FIG. 6B (SEQ ID NO: 6). In preferred embodiments, the Inv9 polypeptide is from a fungus (e.g., a yeast such as Saccharomyces). In other preferred embodiments, the Inv9 has invasion promoting activities.

In a related aspect, the invention features an isolated nucleic acid (e.g., DNA) encoding an Inv9 polypeptide. Preferably, such an isolated nucleic acid sequence includes the INV9 gene of FIG. 6A (SEQ ID NO: 5) and complements an INV9 mutation in *Saccharomyces cerevisiae.*

In another aspect, the invention features a substantially pure Rim1 polypeptide. Preferably, the Rim1 polypeptide is at least 75% identical to the amino acid sequence of FIG. 5A (SEQ ID NO: 4) in the zinc-finger domain, and at least 25% identical throughout the entire length of the polypeptide amino acid sequence. In preferred embodiments, the Rim1 polypeptide is from a fungus (e.g., a yeast such as Saccharomyces). In other preferred embodiments, the Rim1 polypeptide has invasion promoting activities.

In a related aspect, the invention features an isolated nucleic acid (e.g., DNA) encoding a Rim1 polypeptide. Preferably, such an isolated nucleic includes the RIM1 gene of FIG. 5A (SEQ ID NO: 3) and complements a RIM1 mutation in *Saccharomyces cerevisiae,* as is described herein.

In related aspects, the invention further features a cell or a vector (for example, a fungal expression vector), each of which includes an isolated nucleic acid molecule of the invention. In preferred embodiments, the cell is a fungal cell (for example, *S. cerevisiae*). In yet another preferred embodiment, the isolated nucleic acid molecule of the invention is operably linked to a promoter that mediates expression of a polypeptide encoded by the nucleic acid molecule. The invention further features a cell (for example, a fungal cell) which contains the vector of the invention.

In still another aspect, the invention features a transgenic fungus including any of the above nucleic acid molecules of the invention, wherein the nucleic acid molecule is expressed in the transgenic fungus.

In related aspects, the invention also features a method of producing an Inv9 or Rim1 polypeptide. The method involves: (a) providing a cell transformed with a nucleic acid molecule of the invention positioned for expression in the cell; (b) culturing the transformed cell under conditions for expressing the nucleic acid molecule; and (c) recovering the Inv9 or Rim1 polypeptide. The invention further features a recombinant Inv9 or Rim1 polypeptide produced by such expression of an isolated nucleic acid molecule of the invention, and a substantially pure antibody that specifically recognizes and binds to each of these polypeptides or a portion thereof.

By "fungal invasion" is meant a process by which a fungus penetrates, digs, adheres to, or attaches to a substrate. Invasion of a substrate by a fungus may be measured according to standard methods as described herein.

By "fungal invasin" gene is meant a gene encoding a polypeptide capable of promoting or inhibiting the invasion by a fungus into a substrate. This response may occur at the transcriptional level or it may be enzymatic or structural in nature. Fungal invasin genes may be identified and isolated from any fungal species, using any of the sequences disclosed herein in combination with conventional methods known in the art.

By "polypeptide" is meant any chain of amino acids, regardless of length or post-translational modification (for example, glycosylation or phosphorylation).

By a "reporter gene" is meant a gene whose expression may be assayed; such genes include, without limitation, genes encoding β-galactosidase, β-glucosidase, β-glucosidase, and invertase, amino acid biosynthetic genes, e.g., the yeast LEU2, HIS3, LYS2, TRP1 genes, nucleic acid biosynthetic genes, e.g., the yeast URA3 and ADE2 genes, the mammalian chloramphenicol transacetylase (CAT) gene, or any surface antigen gene for which specific antibodies are available. A reporter gene may encode a protein detectable by luminescence or fluorescence, such as green fluorescent protein (GFP). Reporter genes may encode also any protein that provides a phenotypic marker, for example, a protein that is necessary for cell growth or viability, or a toxic protein leading to cell death, or the reporter gene may encode a protein detectable by a color assay leading to the presence or absence of color. Alternatively, a reporter gene may encode a suppressor tRNA, the expression of which produces a phenotype that can be assayed. A reporter gene according to the invention includes elements (e.g., all promoter elements) necessary for reporter gene function.

By "substantially identical" is meant a polypeptide or nucleic acid exhibiting at least 25%, preferably 50%, more preferably 80%, and most preferably 90%, or even 95% identity to a reference amino acid sequence (for example, the amino acid sequence shown in FIG. 5A (SEQ ID NO: 4) or nucleic acid sequence (for example, the nucleic acid sequences shown in FIG. 5A; SEQ ID NO: 3). For polypeptides, the length of comparison sequences will generally be at least 16 amino acids, preferably at least 20 amino acids, more preferably at least 25 amino acids, and most preferably 35 amino acids or greater. For nucleic acids, the length of comparison sequences will generally be at least 50 nucleotides, preferably at least 60 nucleotides, more preferably at least 75 nucleotides, and most preferably 110 nucleotides or greater.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BEAUTY, or PILEUP/PRETTYBOX programs). Such software matches identical or similar sequences by assigning degrees of homology to various substitutions, deletions, and/or other modifications. Conservative substitutions typically include substitutions within the following groups: glycine alanine; valine, isoleucine, leucine; aspartic acid, glutamic acid, asparagine, glutamine; serine, threonine; lysine, arginine; and phenylalanine, tyrosine.

By a "substantially pure polypeptide" is meant a polypeptide (for example, an invasin polypeptide such as the Inv9 or Rim1 polypeptide) that has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, an invasin polypeptide. A substantially pure invasin polypeptide may be obtained, for example, by extraction from a natural source (for example, a fungal cell); by expression of a recombinant nucleic acid encoding an invasin polypeptide; or by chemically synthesizing the protein. Purity can be measured by any appropriate method, for example, column chromatography, polyacrylamide gel electrophoresis, or by HPLC analysis.

By "derived from" is meant isolated from or having the sequence of a naturally-occurring sequence (e.g., a cDNA, genomic DNA, synthetic, or combination thereof).

By "isolated DNA" is meant DNA that is free of the genes which, in the naturally-occurring genome of the organism from which the DNA of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. It also includes a recombinant DNA which is part of a hybrid gene encoding additional polypeptide sequence.

By "transgenic fungal cell" is meant a fungal cell into which (or into an ancestor of which) has been introduced, by means of recombinant DNA techniques, a DNA molecule encoding (as used herein) an invasin polypeptide.

By "positioned for expression" is meant that the DNA molecule is positioned adjacent to a DNA sequence which directs transcription and translation of the sequence (i.e., facilitates the production of, for example, an invasin polypeptide, a recombinant protein, or an RNA molecule).

By "promoter sequence" is meant any minimal sequence sufficient to direct transcription. Included in the invention are promoter elements that are sufficient to render promoter-dependent gene expression controllable for gene expression, or elements that are inducible by external signals or agents; such elements may be located in the 5' or 3' regions of the native gene or engineered into a transgene construct.

By "operably linked" is meant that a gene and a regulatory sequence(s) are connected in such a way as to permit gene expression when the appropriate molecules (for example, transcriptional activator proteins) are bound to the regulatory sequence(s).

By "candidate gene" is meant any piece of DNA which is inserted by artifice into a cell and expressed in that cell. A candidate gene may include a gene which is partly or entirely heterologous (i.e., foreign) to the transgenic organism, or may represent a gene homologous to an endogenous gene of the organism.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic fungal cells. A transgenic fungal cell according to the invention may contain one or more invasin genes.

By "increasing production of a secondary metabolite" is meant a greater level of production of a secondary metabolite in a transgenic fungus of the invention than the level of production relative to a control fungus (for example, a non-transgenic fungus). In preferred embodiments, the level of secondary metabolite production in a transgenic fungus of the invention is at least 10% greater (and preferably more than 30% or 50%) than the resistance of a control fungus. The level of secondary metabolite production is measured using conventional methods.

By "detectably-labelled" is meant any direct or indirect means for marking and identifying the presence of a molecule, for example, an oligonucleotide probe or primer, a gene or fragment thereof, or a cDNA molecule or a fragment thereof. Methods for detectably-labelling a molecule are well known in the art and include, without limitation, radioactive labelling (for example, with an isotope such as $^{32}P$ or $^{35}S$) and nonradioactive labelling (for example, chemiluminescent labelling, for example, fluorescein labelling).

By "purified antibody" is meant antibody which is at least 60%, by weight, free from proteins and naturally-occurring organic molecules with which it is naturally associated. Preferably, the preparation is at least 75%, more preferably 90%, and most preferably at least 99%, by weight, antibody, for example, an acquired resistance polypeptide-specific antibody. A purified invasin antibody (e.g. Inv9 or Rim1) may be obtained, for example, by affinity chromatography using a recombinantly-produced acquired resistance polypeptide and standard techniques.

By "specifically binds" is meant an antibody which recognizes and binds an invasin polypeptide but which does not substantially recognize and bind other molecules in a sample, for example, a biological sample, which naturally includes an invasin polypeptide such as Inv9 or Rim1.

By a "mutation" is meant an alteration in sequence, either by site-directed or random mutagenesis. A mutated form of a protein encompasses point mutations as well as insertions, deletions, or rearrangements. A mutant is an organism containing a mutation The invention provides long awaited advantages over a wide variety of standard screening methods used for distinguishing and evaluating the efficacy of a compound in regulation of gene expression in fungal pathogens. For example, the methods allow for the identification, by genetic selection in a high throughput format, of peptides and compounds that specifically activate or inhibit fungal invasion. These methods also allow the mode of action for such agents to be rapidly delineated. Moreover, these methods are amenable to an iterative compound modification and retesting process to allow for the evolution of more effective compounds from initial hits and leads.

Compounds which inhibit fungal invasion will likely also prevent fungal virulence. These compounds may have therapeutic value in treating plant or animal fungal diseases. Compounds which promote fungal invasion may be useful in increasing yields of commercially important fungal secondary metabolites.

The invention also provides an approach to isolating novel fungal genes important for pathogenesis. These novel genes and the proteins they encode comprise additional targets for compounds.

In addition, the invention provides a means to increase the yield of commercially important secondary metabolites by genetic manipulation of the fungal organism itself. This facilitates the large scale production of fungal products which to date has not been possible. In addition, it allows for the facile identification of "potentiators," (i.e., compounds and peptides) that can activate secondary metabolite production when contacting, or expressed in, fungi. The ability to increase fungal secondary metabolite production has at least two important applications. First, increasing production of secondary metabolites will facilitate identification of new antimicrobial compounds in fungi that otherwise make undetectable levels of these compounds in the laboratory. Second, it will allow increased production of existing secondary metabolites which are useful clinically or for research.

Other features and advantages of the invention will be apparent from the following description of the preferred embodiments thereof, and from the claims.

DETAILED DESCRIPTION

The drawings will first be described.

Drawings

Figure 3:
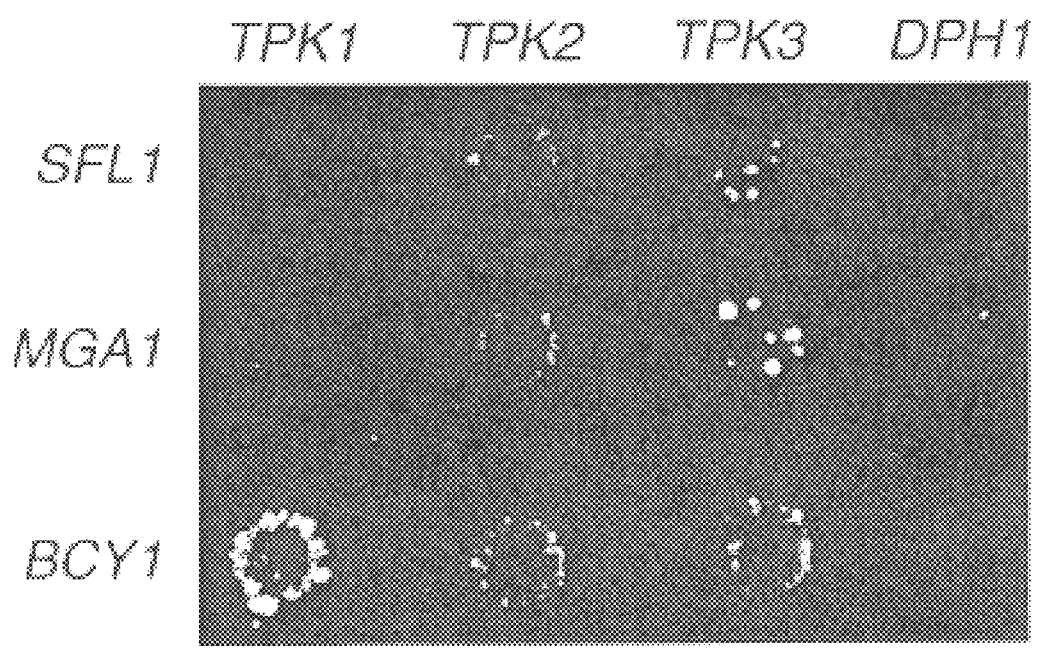

FIG. 3 is a photograph showing the results of a yeast two-hybrid analysis showing preferential affinity of Tpk2 for Mga1 and Sfl1. Gene products tested are shown on the vertical and horizontal axes. Yeast growth indicates an interaction between the products of the genes shown on the respective axes.

Figure 4A:
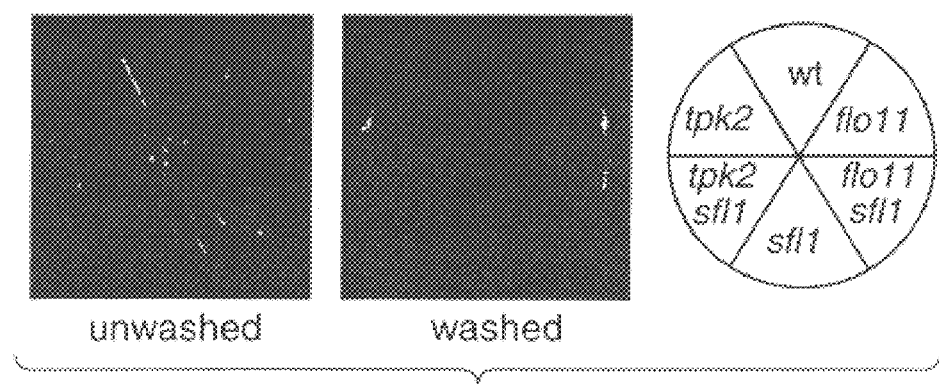

FIG. 4A is a photograph of an epistasis analysis slowing that FLO11 acts downstream of both SFL1 and TPK2 during haploid invasive growth.

Figure 4B:
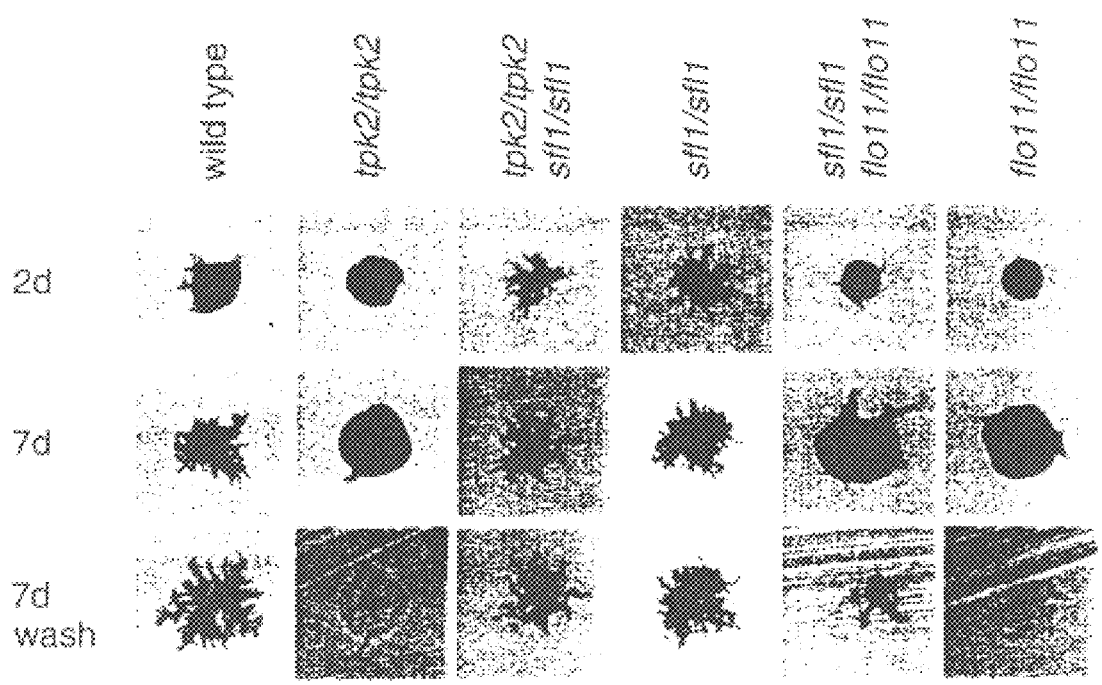

FIG. 4B is a photograph of an epistasis analysis showing that FLO11 acts downstream of both SFL1 and TPK2 during pseudohyphal growth.

FIGS. 5A-1 to 5A-12 show the DNA sequence of the Candida RIM1 gene (SEQ ID NO: 3) and the predicted encoded protein (SEQ ID NO: 4).

Figures 4, 5A:
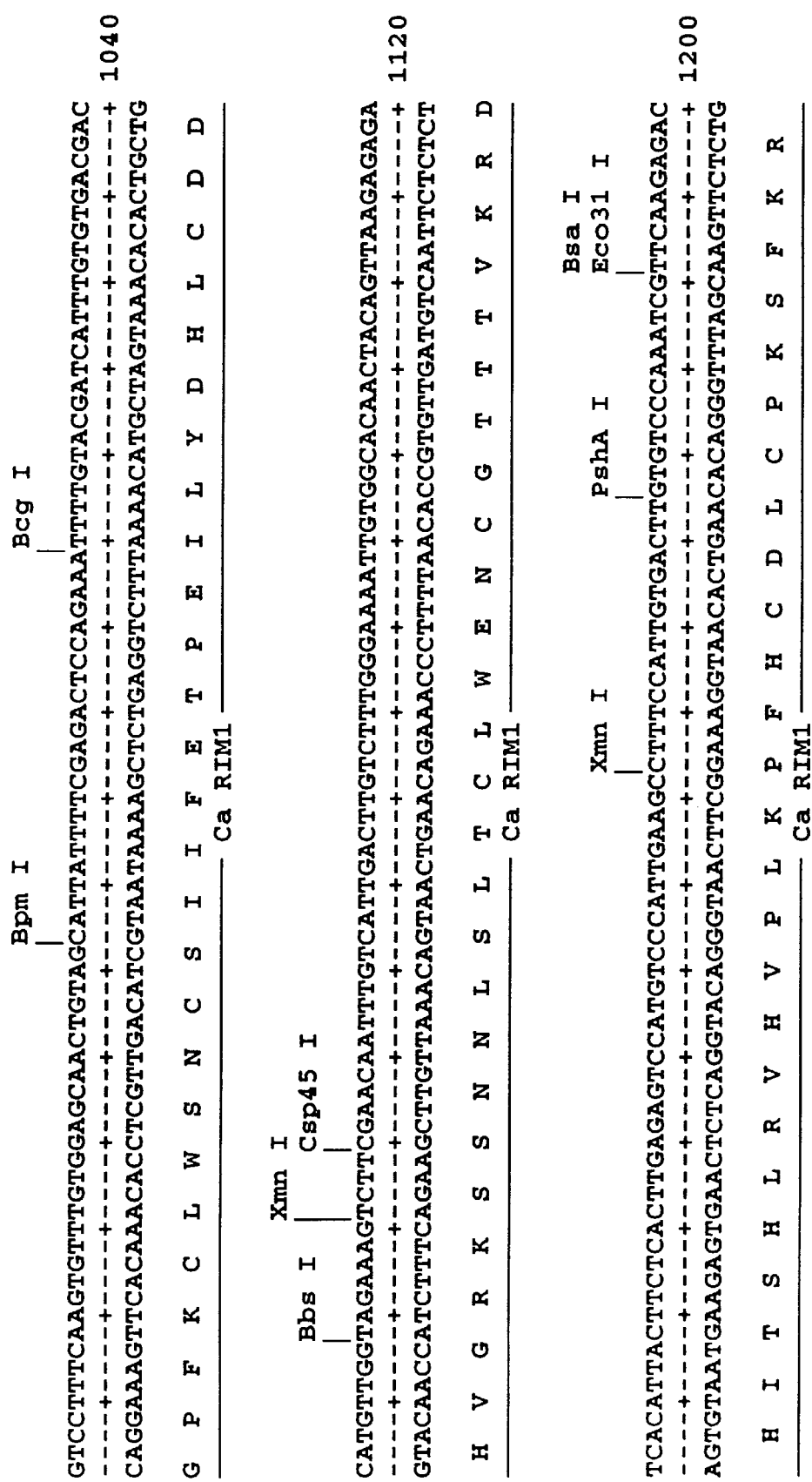
Figures 5, 5A:
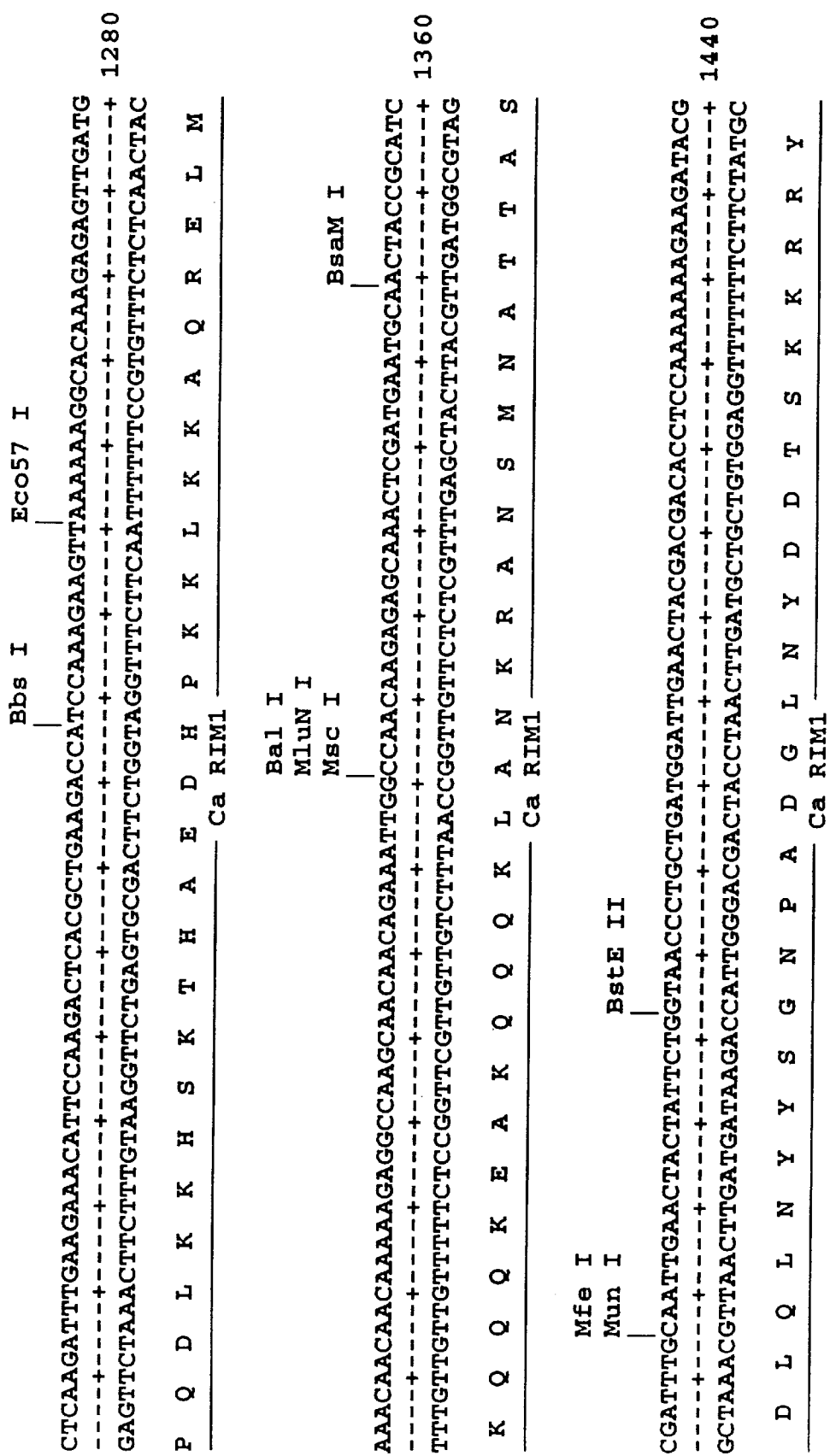
Figures 5, 5A, 6:
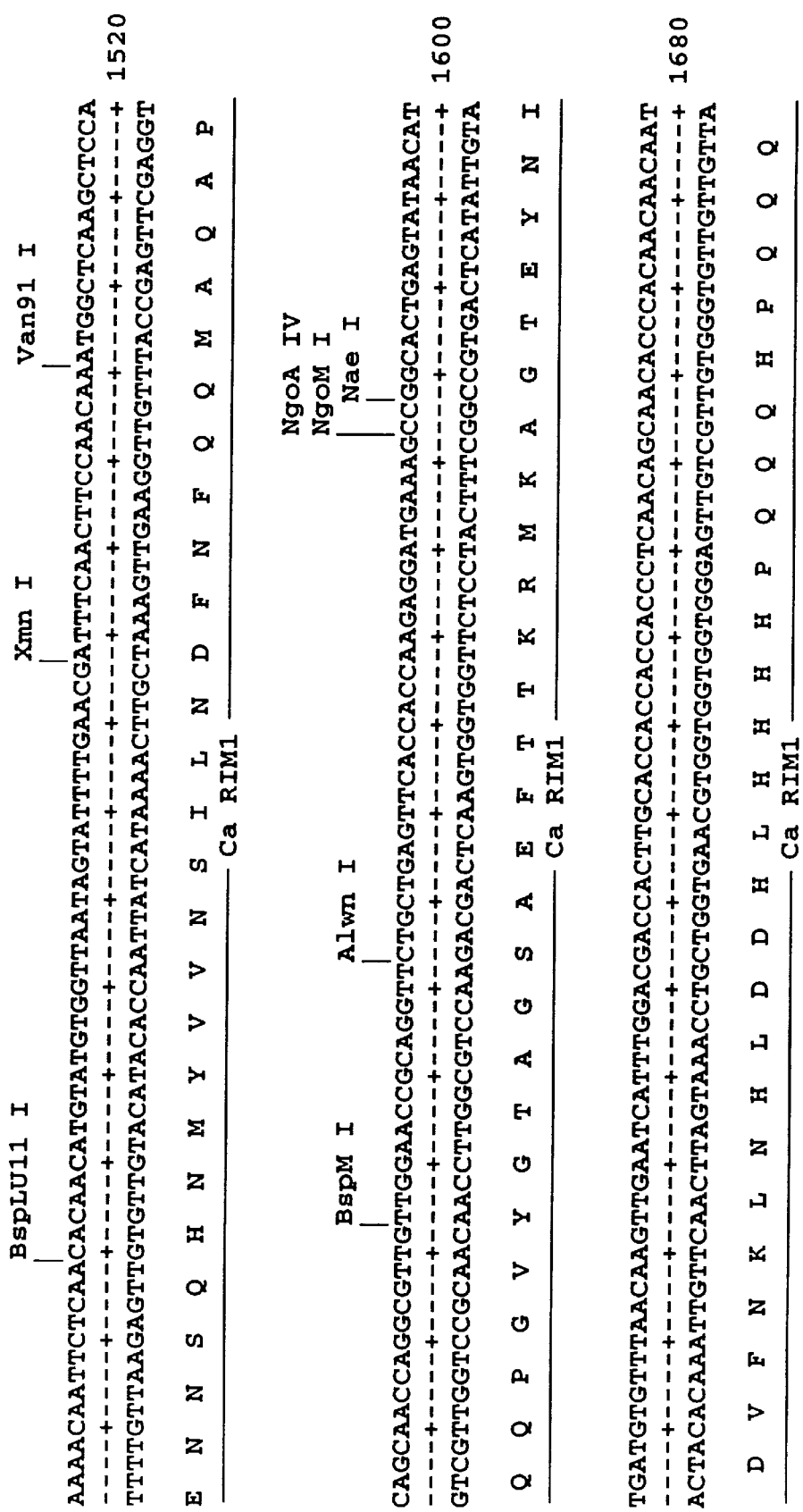
Figures 5, 5A, 6, 7, 8, 9, 10:
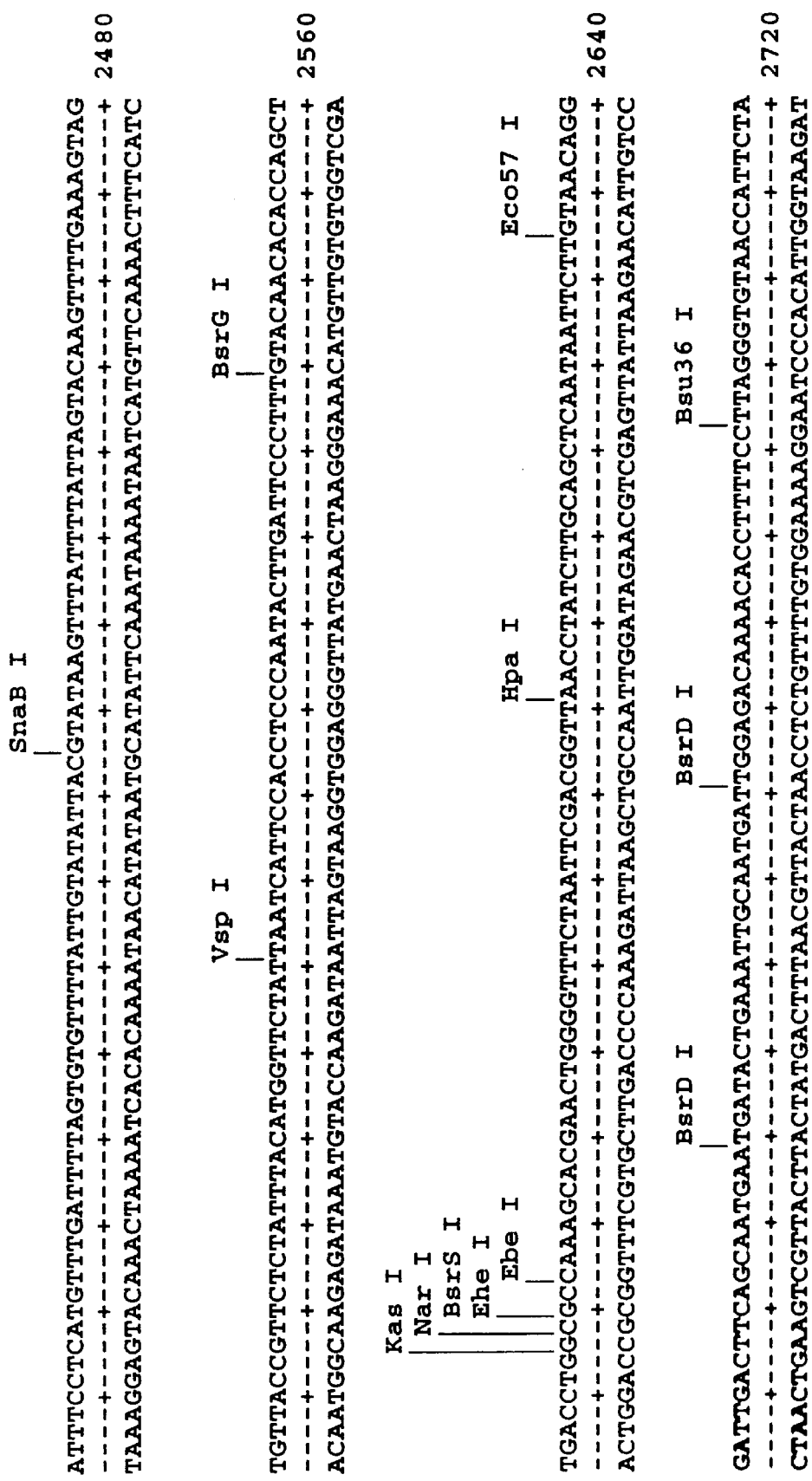
Figures 5, 5A, 6, 7, 8, 9, 10, 11, 12:
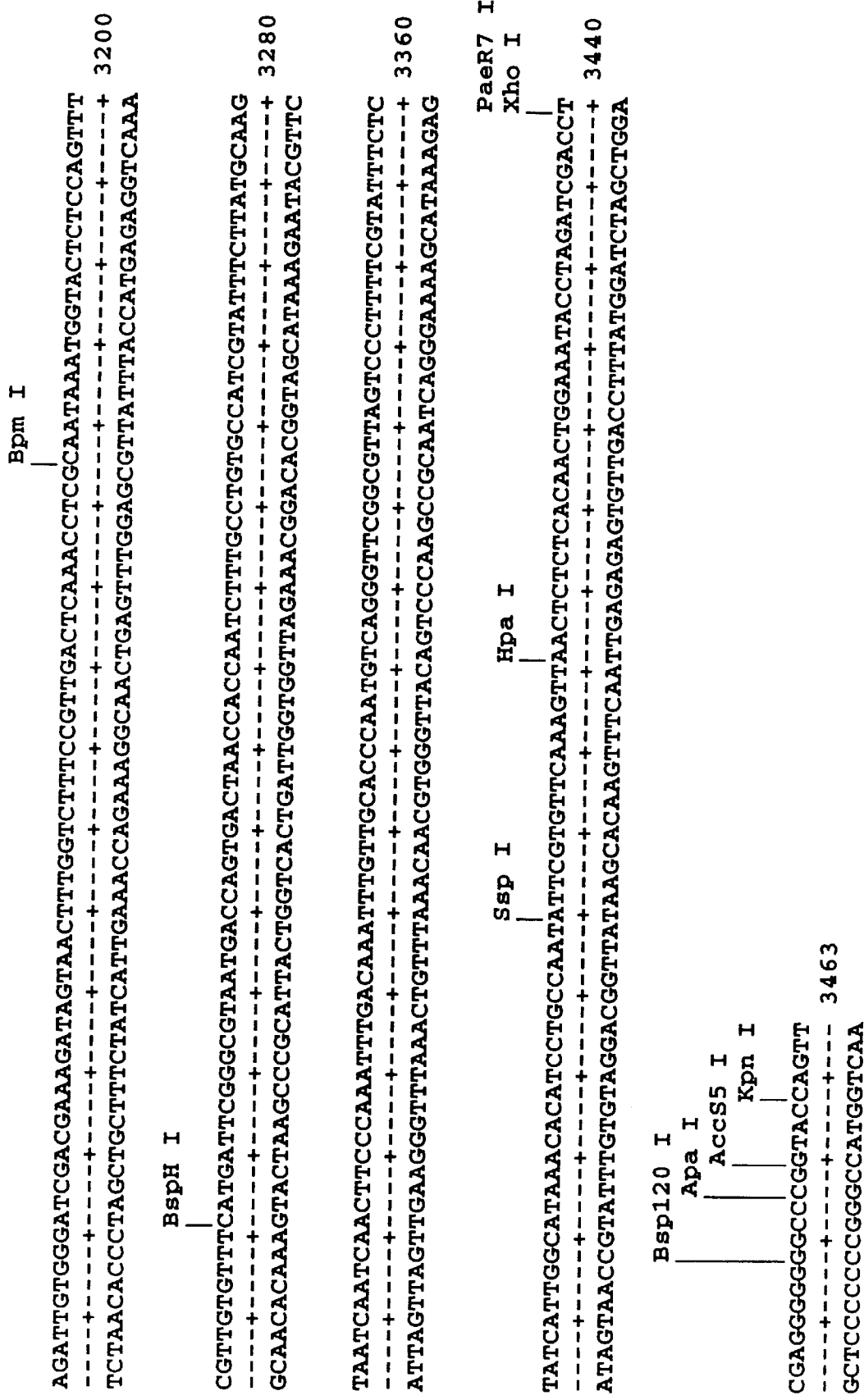
Figure 5B:
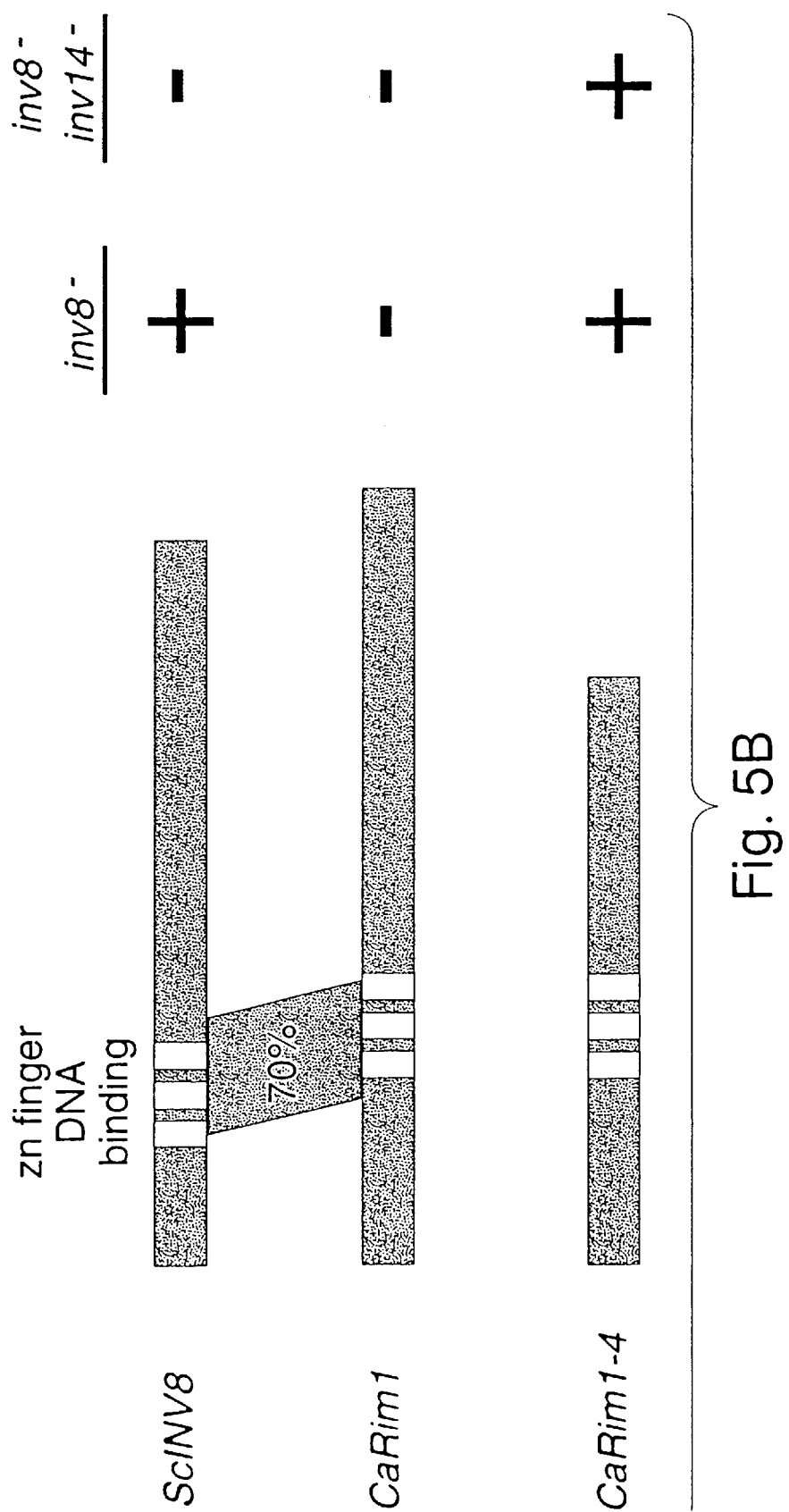
Figure 7:
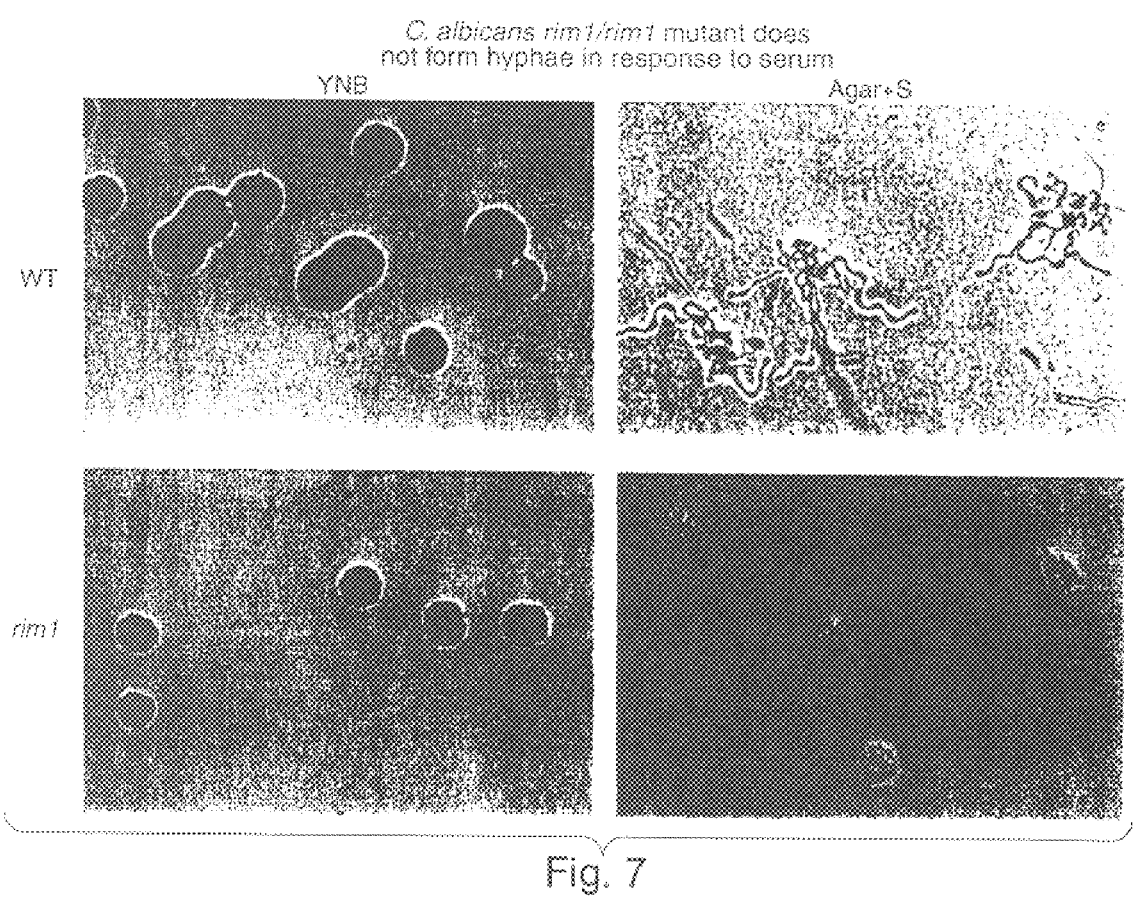
Figure 8:
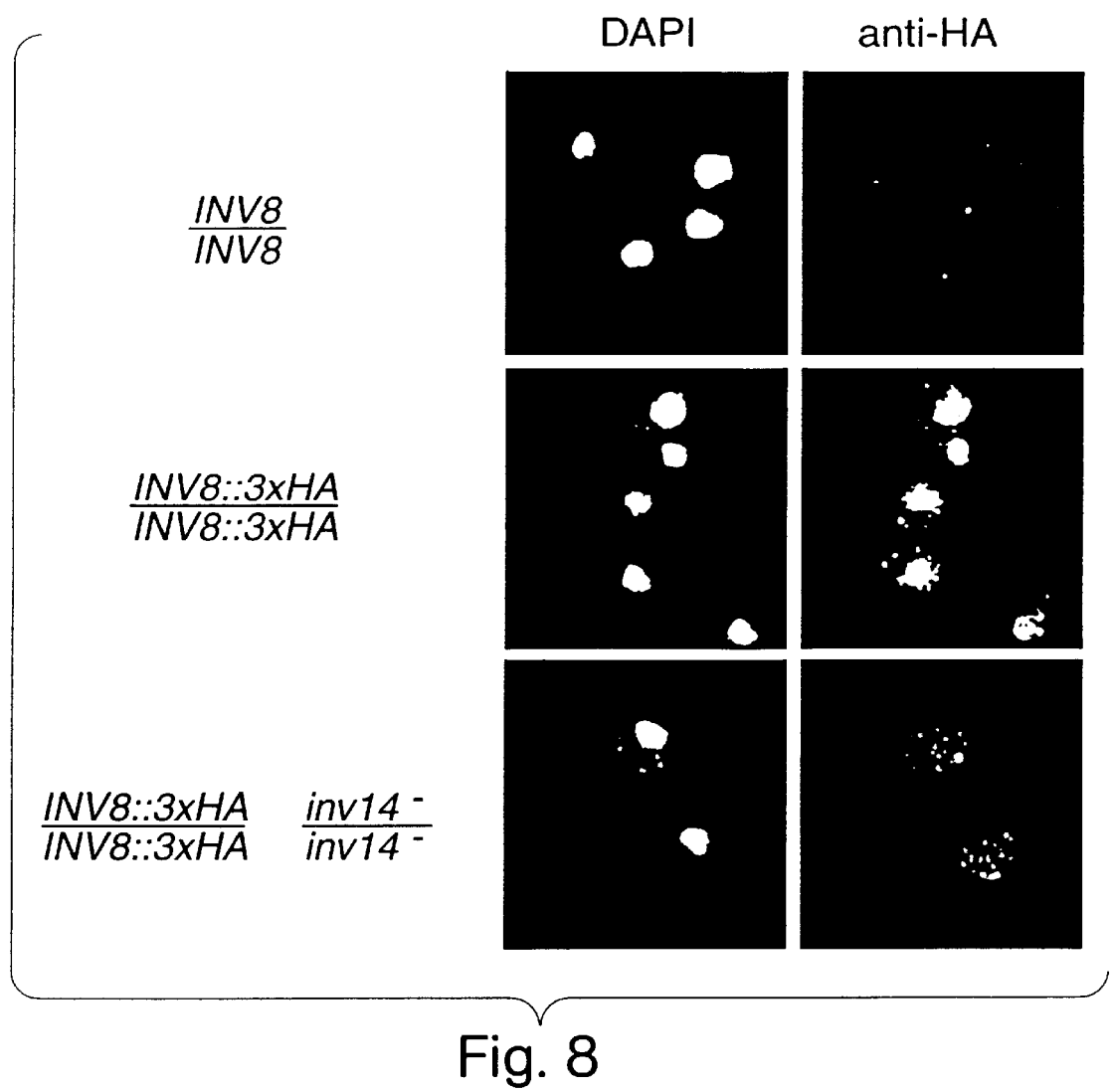
Figure 9:
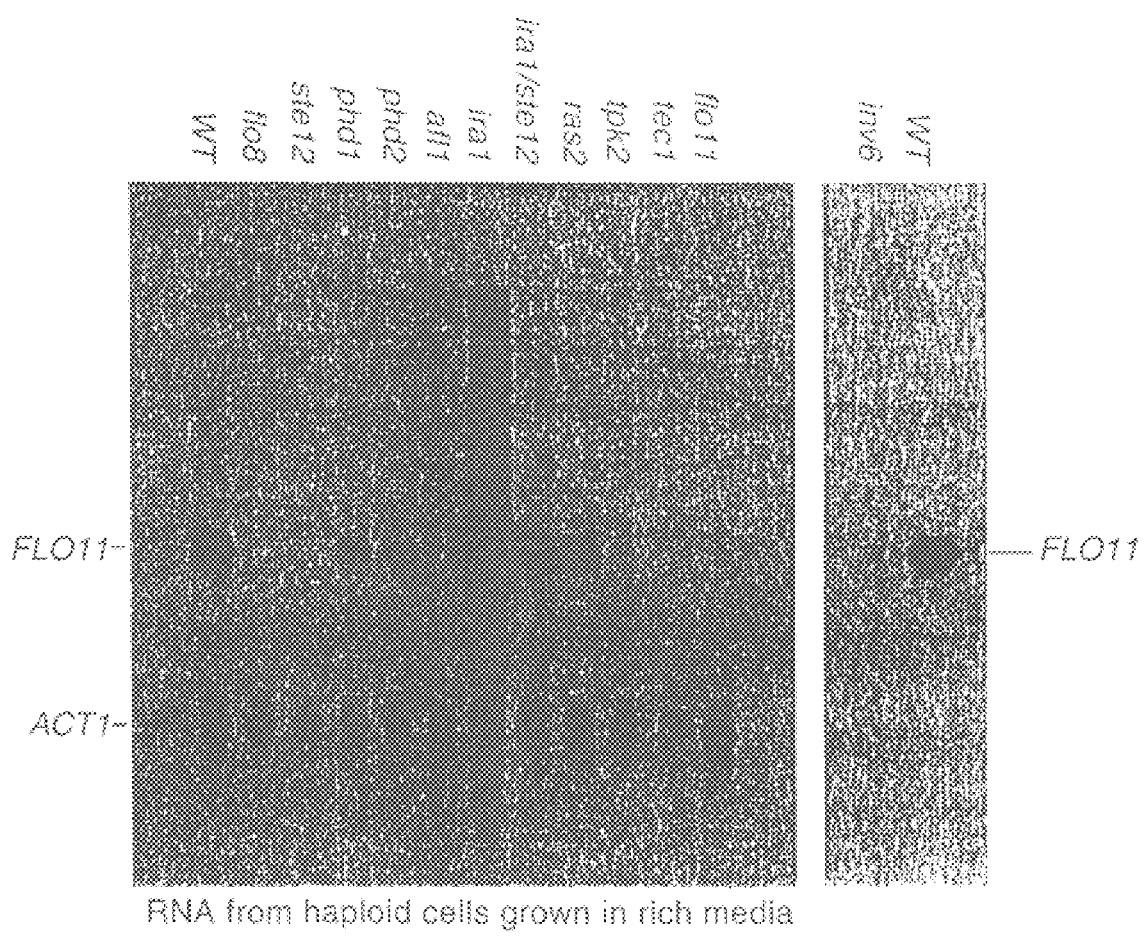
Figure 10:
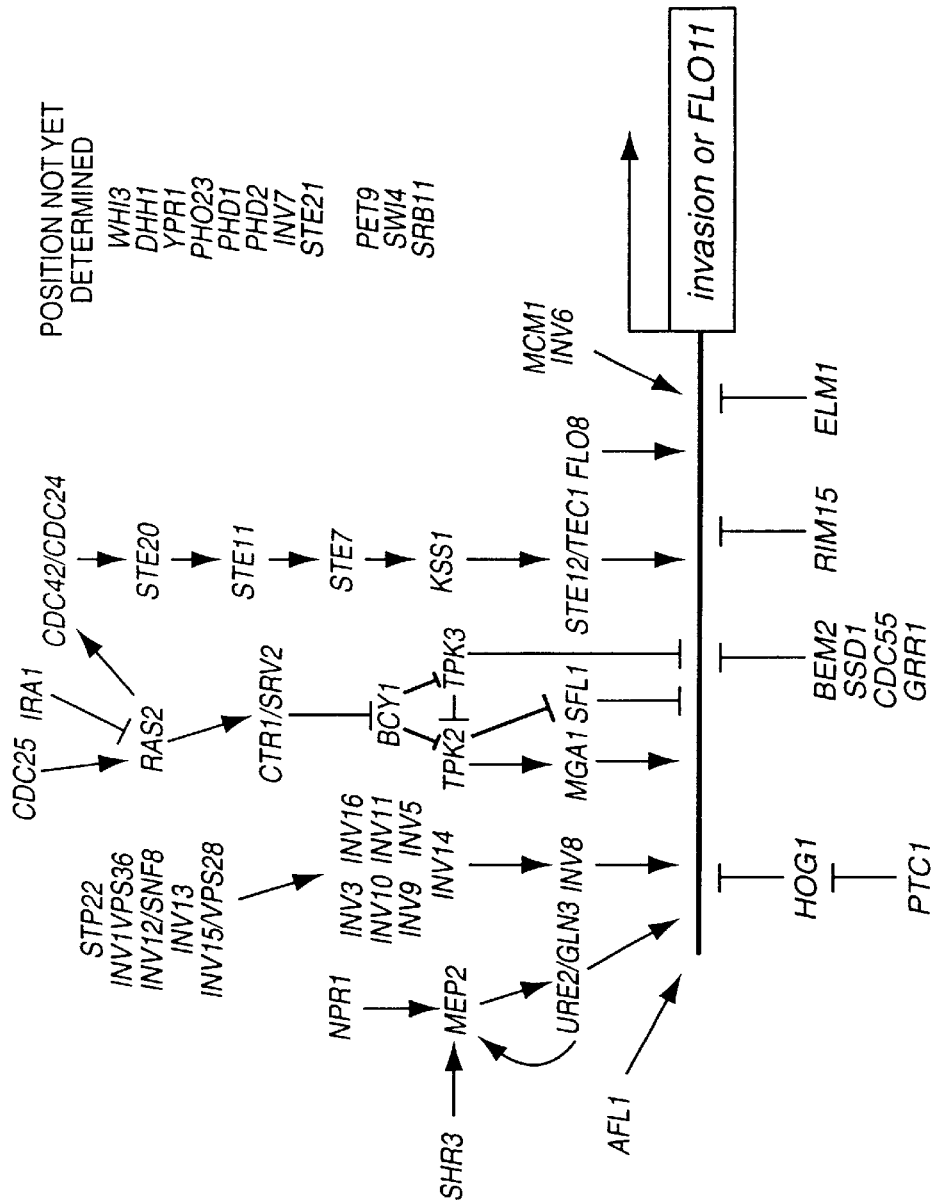
Figure 11:
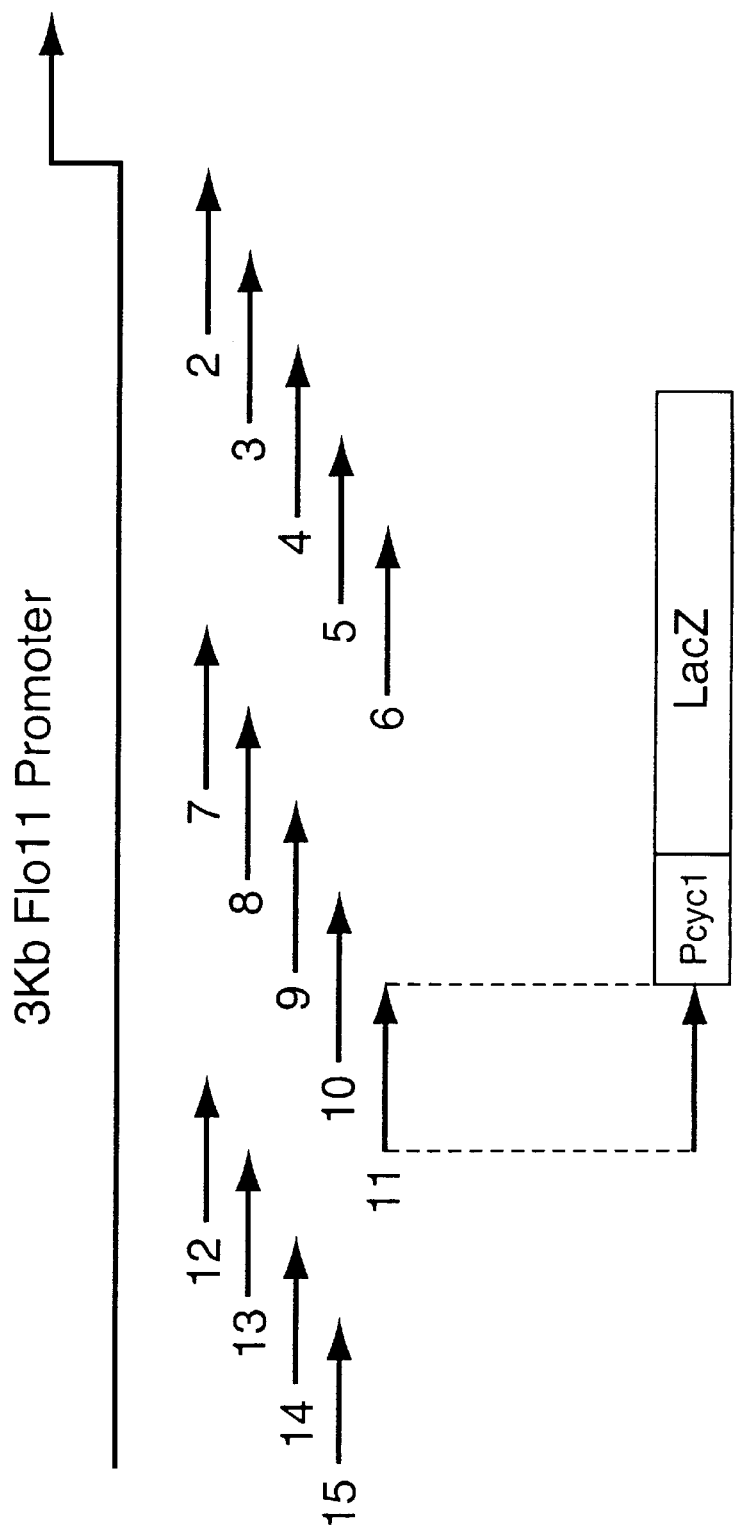
Figure 12:
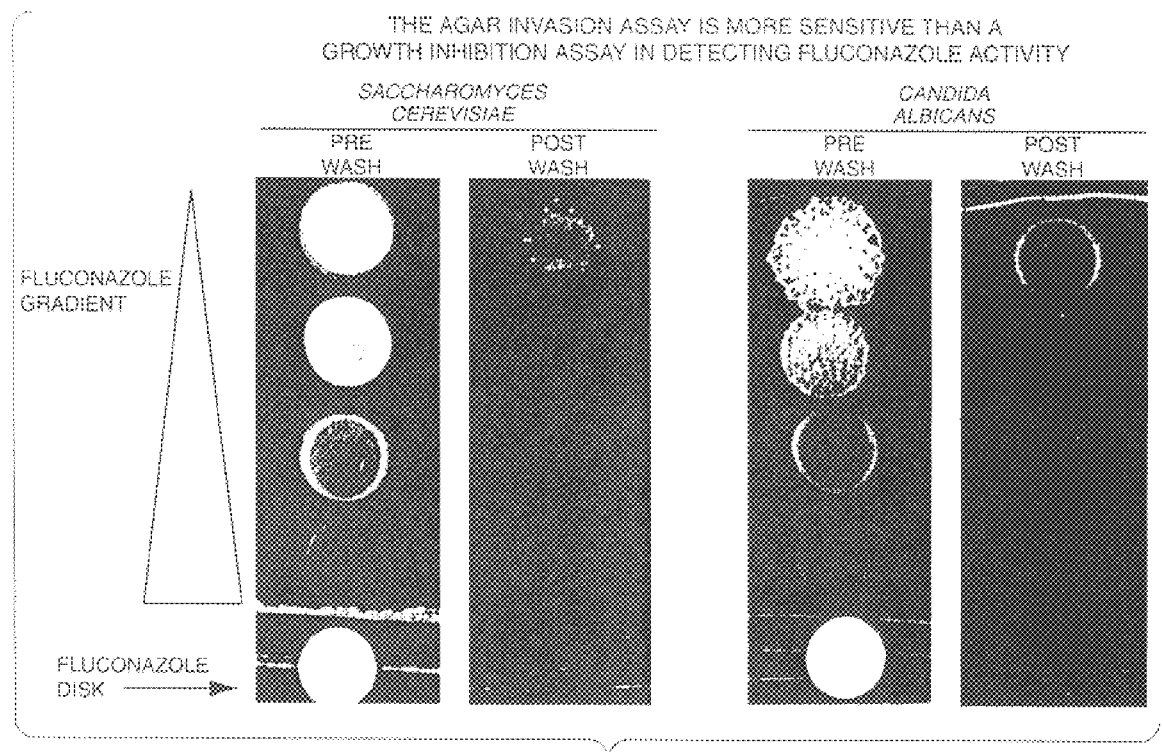

FIG. 5B is a schematic illustration describing the complementation of the S. cerevisiae inv8 phenotype with Candida RIM1.

Figure 1:
FIG. 1 is a western blot showing the effect of mutations in the INV pathway and STE pathway on Inv8 proteolytic processing.

FIGS. 6A-1 to 6A-3 show the DNA sequence of S. cerevisiae INV9 (SEQ ID NO: 5).

FIG. 6B shows the predicted amino acid sequence of S. cerevisiae Inv9 (SEQ ID NO: 6).

FIG. 7 is a series of photographs of phenotypic analysis of the serum response of Candida rim1/rim1 mutants.

FIG. 8 is a series of photographs showing that processing of Inv8 is required for its nuclear accumulation.

FIG. 9 is a photograph of a northern blot showing the steady-state levels of FLO11 mRNA in a variety of invasion-defective (flo8, ste12, phd1, phd2, afl1, ras2, tpk2, tec1, flo11, and inv6) and hyper-invasive mutants (ira1). The blot was probed with probes for FLO11 and ACT1.

FIG. 10 is a schematic illustration of genes and pathways that regulate invasion. Pointed arrows denote activation, flat-ended arrows indicate repression.

FIG. 11 is a schematic illustration showing the relative positions of the FLO11 promoter fragments used to generate reporter constructs.

FIG. 12 shows the results of a gradient plate assay, demonstrating that an agar invasion screen could be employed as a system for identifying antifungal compounds.

We have discovered a series of interconnected signal transduction cascades which regulate fungal invasion and pseudohyphal growth. From S. cerevisiae, we identified new roles for previously characterized genes invasion and pseudohyphal growth (AFL1, DHH1, INV1, INV5, INV6, INV7, INV8, INV9, INV10, INV11, INV12, INV13, INV14, INV15, BEM2, CDC25, HOG1, IRA1, MCM1, MGA1, PET9, PHD2, PHO23, PTC1, RIM15, SFL1, SRB11, SSD1, STE21, STP22, SWI4, TPK2, TPK3, YPR1). Genetic and biochemical analysis has allowed us to place these genes, and other genes known to regulate invasion, into a series of parallel signal transduction cascades. Table 1, below, lists the genes of which we have identified that regulate invasion and/or pseudohyphal growth in S. cerevisiae. These genes are cross-referenced with the corresponding sequence name as designated by the Saccharomyces Genome Database. Sequences of these genes and their putative transcriptional regulatory elements are also found at the Saccharomyces Genome Database (http://genome-www.stanford.edu/Saccharomyces/).

TABLE 1

| Gene Name | Sequence Name | Gene Name | Sequence Name |
| --- | --- | --- | --- |
| INVI/VPS36 | YLR417w | PHD1 | YKL043w |
| INV3/DFG16 | YOR030w | ELM1 | YKL048c |
| INV5 | YOR275c | FLO11 | YIR019c |
| INV6 | YMR164c | SSD1 | YDR293c |
| INV7 | YDL233w | IRA1 | YBR140c |
| INV8 | YHL027w | CDC25 | YLR310c |
| INV9 | YGL046w + YGL045w | RAS2 | YNL098c |
| INV10 | YMR063w | BCY1 | YIL033c |
| INV11 | YNL294c | TPK3 | YKL166c |
| INV12/SNF8 | YPL002c | MGA1 | YGR249w |
| INV13 | YJR102c | SFL1 | YOR140w |
| INV14 | YMR154c | BEM2 | YER155c |
| INV15/VPS28 | YPL065w | CDC55 | YGL190c |
| INV16 | not cloned | NPR1 | YNL183c |
| STP22/ | YCL008c | MEP2 | YNL142w |
| MCM1 | YMR043w | SHR3 | YDL212w |
| FLO8 | YER108c | URE2 | YNL229c |
| WH13 | YNL197c | GLN3 | YER040w |
| SRV2 | YNL138w | CDC42 | YLR229c |

TABLE 1-continued

| Gene Name | Sequence Name | Gene Name | Sequence Name |
| --- | --- | --- | --- |
| CYR1 | YJL005w | CDC24 | YAL041w |
| AFL1 | YEL007w | STSE11 | YLR362w |
| PTC | YDL006w | STE7 | YDL159w |
| STE20 | YHL007c | KSS1 | YGR040w |
| TPK2 | YPL203w | STE12 | YHR084w |
| YPR1 | YDR368w | TEC1 | YBR083w |
| PHO23 | YNL097c | STE21 | YDR335w |
| DHH1 | YDL160c | SIR4 | YDR227w |
| PHD2 | YOL116w | PET9 | YBL030c |
| GRR1 | YJR090c | SWI4 | YER111c |
| RIM15 | YFL033c | SRB11 | YNL025c |
| HOG1 | YLR113w | | |

We have constructed a "wiring diagram" of these signal transduction cascades and shown directly that many of these genes regulate fungal invasion, at least in part, through the regulation of a single gene, FLO11. The identification of the convergence of signals onto a single target has facilitated improved screening methods designed to evaluate and identify therapeutic agents useful for inhibiting fungal pathogenesis in either animal or plant hosts. Furthermore, our discovery provides the basis for screening methods useful for identifying a variety of new fungal virulence factors. Identification of such virulence factors further facilitates the development of targeted reagents for use as anti-pathogens. In addition, the improved screening methods provide the basis for identifying factor that increase production of important fungal secondary metabolites.

The following experimental examples are intended to illustrate, not limit, the scope of the claimed invention.

Screens to Isolate Genes Involved in Pseudohyphal Growth and Invasion

Below we describe experimental evidence that a series of signal transduction cascades operates in cooperation to regulate pseudohyphal growth and haploid digging in solid medium in S. cerevisiae.

On solid media containing high glucose and low nitrogen, diploid cells of S. cerevisiae form pseudohyphae, which consist of chains of elongated cells that form invasive filaments (Gimeno et al., Cell 1992, 68:1077–1090). On rich medium, haploid cells, but not diploid cells, manifest invasive growth, referred to as "digging" (Roberts and Fink, Genes Dev. 1994, 8:2974–85). The nutritional signals that eventuate in both pseudohyphal growth and haploid invasive growth involve several pathways. To isolate S. cerevisiae genes involved in these behaviors, we have performed a series of screens for mutants defective in either pseudohyphal growth or haploid invasion. These screens are described below.

Screen 1. Identification of Mutants that Eliminate Invasion During Pseudohyphal Growth.

Mutagenesis of yeast and screens were conducted as described in Mosch and Fink, (Genetics 1997, 145:671–684). Briefly, a direct visual screen for transposon-induced mutants unable to invade the agar when grown on low nitrogen SLAD agar was conducted in a MATa/α haploid strain capable of pseudohyphal growth. Secondary screening identified a subset of mutants that make long cells and, thus, are capable of all aspects of pseudohyphal growth other than invasion.

Screen 2. Identification of Digging-Defective Mutants.

S. cerevisiae mutants defective for haploid invasive growth were identified using a plate washing assay described in (Roberts and Fink, supra). Transposon-mutagenized haploids, constructed as described in Mösch and Fink (Genetics 1997, 145:671–84 and Burns et al., Genes Dev. 1994 8:1087–105), were plated on YPD to allow formation of well-isolated single colonies. After 3–5 days growth at 30° C., plates were replica-plated and the surface of the master plate was washed with a stream of water. Colonies of invasion-defective mutants wash completely (or nearly so) from the agar, whereas many cells of a wild-type strain remained in the agar after washing. Mutant strains were subsequently picked from the replicas of colonies that exhibited an invasion-defective phenotype.

Screen 3. Identification of Hyperinvasive Mutants.

Transposon-mutagenized haploids were plated to YPD and grown as described in Screen 2 above. Colonies with a surface morphology that appeared more "rough" than wild-type colonies were picked—a rough colony surface is indicative of hyperinvasion. Secondary testing subsequently identified mutants in which more cells remained in the agar after washing as compared to wild-type controls. Such mutants were retained as hyper-invasive mutants.

Screen 4. Identification of Mutations Specifically Affecting The INV Pathway.

This screen relied upon our observation that, unlike mutations affecting other characterized genes required for pseudohyphal growth, inv mutants were more resistant than wild-type strains to the whitening agent calcoflour. In addition, as is true for all invasion-defective mutants, inv haploids exhibited a colony surface morphology that appears more smooth than wild-type colonies when grown on YPD agar. A collection of transposon-induced calcoflour-resistant mutants exhibiting a smooth colony morphology when grown on YPD agar were also identified.

For all mutations induced by transposon insertion, genomic DNA flanking the transposon insertion site was isolated and sequenced by conventional methods. Nucleotide sequence of flanking DNA was then compared to the genomic sequence of *S. cerevisiae* to identify the affected gene.

Screen 5. Identification of High-Copy Suppressors of an Invasion-Defective Mutant.

A library of plasmids containing yeast genomic DNA was transformed into an invasion-defective (Inv-) diploid whi3 strain. These library plasmids contained an origin of replication that promotes maintenance in high-copy number (the 2 $\mu$ origin). Transformants were plated on selective media (SC-URA), plates were incubated for 1–2 days, and then a plate washing assay was performed. High-copy plasmids that suppress the Inv-phenotype promoted a transient period of invasive growth into synthetic media. This growth was identified as small pits of colonies that remained in the agar after the plate washing assay. Several genes were identified as high-copy suppressors of the Inv-phenotype of whi3 mutants, including MCM1 and PHD2. Subsequent analysis of phd2-deleted and mcm1 partial loss-of-function mutants demonstrated that these genes regulate invasion and FLO11 expression.

From the above screens, we have identified 60 genes which regulate pseudohyphal growth or haploid invasion in *S. cerevisiae*. These genes, referred to as invasins, have been further categorized into at least six signal transduction cascades. Based on the resulting phenotype following mutation or overexpression, these genes can be further classified as "fungal invasion-promoting" or "fungal invasion-inhibiting." For example, a *S. cerevisiae* strain containing a complete deletion of AFL1 does not form filaments or invade under conditions in which a wild-type strain does, and no invasion is observed under conditions that normally induced invasion during pseudohyphal growth or haploid digging. An example of a signal transduction cascade is described below Twelve *S. cerevisiae* genes which comprise this signal transduction pathway required for agar invasion have been identified, cloned, and characterized. INV8, encoding a transcription factor whose activity is regulated by proteolysis, is the most downstream member of the pathway. The other twelve members (INV1, INV3, INV5, INV9, INV10, INV11, INV12, INV13, INV14, INV15, INV16, and STP22) are all required for proteolytic regulation of Inv8. As shown in FIG. 1, mutations in these genes, but not mutations in any other invasin genes thus far examined, block Inv8 processing. One of the INV members, Inv14, is a cytoplasmic cysteine protease of the calpain family. It was surprising that this signal transduction pathway was conserved in fungi and served, in other fungi, to regulate the production of secondary metabolites and secreted enzymes that are able to degrade extracellular substrates. Homologs of the *S. cerevisiae* genes have been found, for example, in *A. nidulans*, where a similar set of genes regulate transcription of a number of secreted catabolizing enzymes in response to extracellular pH; in *Yarrowia lipolytica*, as the transcriptional regulator of an abundant, secreted alkaline protease; and in *Penicillium (P.) chrysogenum* and *A. niger*, where it has a role similar to that found in *A. nidulans*. In *A. nidulans* and in *P. chrysogenum*, the pathway directly regulates the production of penicillin (penicillin production is regulated by the activated form of the transcription factor).

Figure 2A:
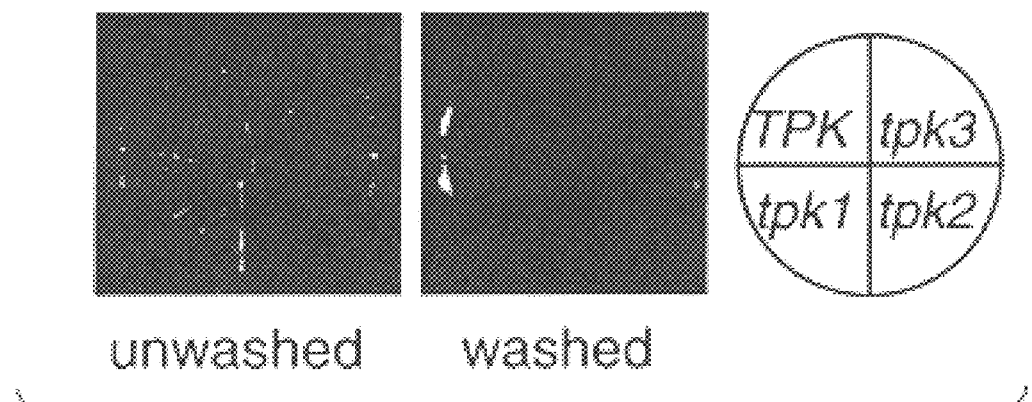
FIG. 2A is a series of photographs showing haploid invasion phenotypes for wild-type strains and strains with mutations in TPK genes.
Figure 2B:
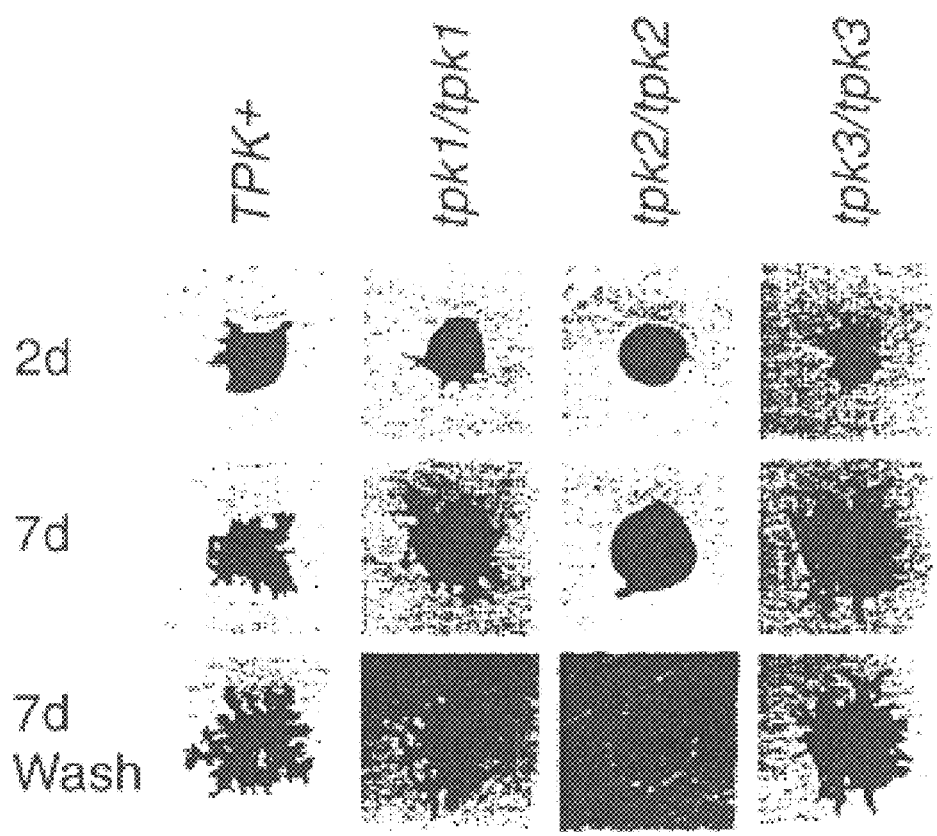
FIG. 2B is a series of photographs showing pseudohyphal phenotypes for wild-type strains and strains with mutations in TPK genes.

Other additional members of these signal transduction cascades are identified through a variety of standard techniques. First, enhancers and suppressors of phenotypes of mutant strains are isolated using standard techniques known to those skilled in the art (Ausubel, supra). Second, proteins which interact with pathway members are isolated using yeast two-hybrid methods (Fields and Song, Nature 1989, 340:245–246; Chien et al., Proc. Natl. Acad. Sci. USA 1991, 88:9578–9582; Brent and Finley, Annu. Rev. Genet. 1997, 31:663–704). In one example, proteins which specifically interact with an A kinase catalytic subunit Tpk2, and not with related proteins Tpk1 and Tpk3 were identified and shown to be important for pseudohyphal development. Diploid tpk2 strains grown on SLAD (low nitrogen medium) were completely defective for pseudohyphal development, whereas tpk3 diploid strains were greatly enhanced for filamentation (FIG. 2B). Similarly, haploid tpk2 mutants were defective for invasive growth and tpk3 mutants were hyperinvasive (FIG. 2A). tpk1 mutants were indistinguishable from wild-type strains as both haploids and diploids. The accentuated filamentation and invasion phenotypes of tpk3 mutants required a functional Tpk2 as tpk2 tpk3 mutants had the same phenotype as tpk2 single mutants. As Tpk2 appeared to be uniquely required for pseudohyphal growth, we used a two-hybrid screen to identify proteins that interact specifically with Tpk2. The intact open reading frame of TPK2 was fused to coding sequence for the Gal4 DNA binding domain and used to screen a library of yeast genomic fragments fused to coding sequence for the Gal4 transcriptional activation domain. Activation of the GAL4-ADE2 reporter, leading to adenine-independent growth of an ade-strain, was taken as preliminary evidence for an interaction between the Gal4 DNA binding domain:Tpk2 fusion and the Tpk2 interacting protein fused to the Gal4 activation domain. Positive clones were then retested in the two-hybrid assay with Tpk1, Tpk2, Tpk3, or Dph1 fused to the Gal4 DNA binding domain. DPH1, a gene required for diphthamide biosynthesis, was used to control for interactions that were not specific to the PKA isoforms.

Two classes of proteins interacted with Tpk2 in the two-hybrid assay: the first class was indiscriminate and interacted with Tpk1, Tpk2, and Tpk3; the second class was selective and interacted preferentially with Tpk2 (FIG. 3). One of the proteins that interacted with all three catalytic subunits is Bcy1, the negative regulatory subunit of PKA, which had previously been shown to bind Tpk1, Tpk2, and Tpk3. The second class consisted of Sfl1 and Mga1, putative transcription factors belonging to a group of five yeast proteins (Mga1, Sfl1, Hsf1, Skn7, and Hms2) containing a helix-turn-helix DNA binding motif. All but Skn7 contain at least one consensus PKA phosphorylation site ([R/K][R/K]X[S/T]): Sfl1 has five, Mga1 has two, Hsf1 has four, and Hms2 has one.

We deleted the open reading frame of both MGA1 and SFL1. sfl1 mutants had a dramatic phenotype: sfl1 haploid strains were extremely flocculent and hyperinvasive, whereas diploids homozygous for a deletion of sfl1 were greatly enhanced for filamentation (FIG. 4A–B). We constructed an sfl1 tpk2 double mutant to see if the tpk2 pseudohyphal defect was blocked by loss of function of Sfl1. sfl1 tpk2 double mutants had the same phenotype as sfl1 single mutants, suggesting Sfl1 acts downstream of Tpk2 (FIG. 4A–B). We could not detect a dramatic defect in pseudohyphal formation in mga1 null mutants.

Similar two-hybrid screens can also be used to identify additional members of any of the signal transduction cascades described herein. Candidate genes are then analyzed using a variety of techniques known to those skilled in the art, such as construction of mutant strains or overexpression.

Identification of transcriptional targets of genes in the fungal signal transduction pathways, such as Inv8 or Sfl1, are used to identify gene products which are directly responsible for extracellular substrate degradation or invasion. For example, identification of Inv8 transcriptional targets is useful to identify gene products directly responsible for agar invasion. Identification of such target genes provides excellent reporters of the INV pathway, which will make it possible to demonstrate the relative activities of the unprocessed versus the proteolyzed Inv8 protein and to define the mechanisms by which Inv8 activates and represses target genes. Alternatively, identification of homologs, such as by screening for complementation of the phenotype in *S. cerevisiae,* in other fungi can be carried out to identify fungal gene products which regulate production of secondary metabolites, such as antibiotics, anti-hypercholesterolemic agents, immunosuppressives, or antifungal drugs.

Based on the work described herein, it is possible to discover and develop novel antifungal therapeutic drugs; identify and commercialize new fungal secondary metabolites; improve yields of presently available fungal products; and develop technologies and products to address unmet fungal challenges. It is likely that the signal transduction machinery is conserved among fungi. Thus, based on the discoveries described herein, each of these signal transduction cascades represents a target for antifungal drugs and/or regulation of secondary metabolites. Strains of *S. cerevisiae* carrying mutant alleles of any of the genes can be used to screen for fungal homologs, including those from important pathogenic fungi and commercially important fungi, such as Aspergillus sp., Penicillium sp., *Acremonium chrysogenum, Yarrowia lipolytica* and *Phaffia rhodozyma,* which are capable of complementing or rescuing the mutant phenotype. These strains can be genetically modified such that the rescued organisms are capable of increased growth or survival, such that these organisms can be isolated using selection based screens described herein. Selection-based screens allow for high-throughput, and thus provide a more rapid approach to gene isolation than those currently used. Moreover, screens for genes which complement mutant phenotypes allows for isolation of genes which share functional properties but which do not contain high degrees of similarity at the nucleotide or amino acid level.

Isolation of Invasin Homologs

Any fungal cell can serve as the nucleic acid source for the molecular cloning of an invasin homolog. Isolation of an invasin homolog (e.g., AFL1, DHH1, INV1, INV5, INV6, INV7, INV8, INV9, INV10, INV11, INV12, INV13, INV14, INV15, BEM2, CDC25, HOG1, IRA1, MCM1, MGA1, PET9, PHD2, PHO23, PTC1, RIM1, RIM15, SFL1, SRB11, SSD1, STE21, STP22, SWI4, TPK2, TPK3, or YPR1) involves the isolation of those DNA sequences which encode a polypeptide exhibiting properties or activities associated with promotion or inhibition of fungal invasion. Based on the sequences of the invasin genes and polypeptides described herein, the isolation of additional invasin homolog regulatory and coding sequences from a variety of fungi (e.g.,Candida, Aspergillus, Penicillium, Mucor, Monascus, Trichoderma, Fusarium, Tolypocladum, Acremonium, Cryptococcus, Ustilago, Magneporthe, Acremonium, Yarrowia, and Phaffia) is made possible using standard strategies and techniques that are well known in the art.

In one particular example, any of the invasin sequences described herein may be used, together with conventional screening methods of nucleic acid hybridization screening. Such hybridization techniques and screening procedures are well known to those skilled in the art and are described, for example, in Benton and Davis, Science 1977, 196:180; Grunstein and Hogness, Proc. Natl. Acad. Sci., USA 1975, 72:3961; Ausubel et al. et al., 1997, *Current Protocols in Molecular Biology,* Wiley Interscience, New York; Berger and Kimmel, *Guide to Molecular Cloning Techniques,* 1987, Academic Press, New York; and Sambrook et al., *Molecular Cloning: A Laboratory Manual,* Cold Spring Harbor Laboratory Press, New York. In one particular example, all or part of the *Candida albicans* RIM1 cDNA (described herein) may be used as a probe to screen a recombinant fungus DNA library (e.g., a recombinant expression library prepared from *Aspergillus nidulans*) for homologs having sequence identity to the *Candida albicans* RIM1 gene. Hybridizing sequences are detected by plaque or colony hybridization according to the methods described below.

Alternatively, using all or a portion of the amino acid sequence of the Rim1 polypeptide, one may readily design Rim1-specific oligonucleotide probes, including Rim1 degenerate oligonucleotide probes (i.e., a mixture of all possible coding sequences for a given amino acid sequence). These oligonucleotides may be based upon the sequence of either DNA strand and any appropriate portion of the Rim1 sequence. General methods for designing and preparing such probes are provided, for example, in Ausubel et al. (supra), and Berger and Kimmel (supra). These oligonucleotides are useful for RIM1 homolog isolation, either through their use as probes capable of hybridizing to RIM1 complementary sequences or as primers for various amplification techniques, for example, polymerase chain reaction (PCR) cloning strategies. If desired, a combination of different oligonucleotide probes may be used for the screening of a recombinant DNA library. The oligonucleotides may be detectably-labeled using methods known in the art and used to probe filter replicas from a recombinant DNA library. Recombinant DNA libraries are prepared according to methods well known in the art, for example, as described in Ausubel et al. (supra), or they may be obtained from commercial sources.

In one particular example of this approach, homolog RIM1 sequences having greater than 75% identity are detected or isolated using high stringency conditions. High stringency conditions may include hybridization at about 42° C. and about 50% formamide, 0.1 mg/mL sheared salmon sperm DNA, 1% SDS, 2×SSC, 10% Dextran sulfate, a first wash at about 65° C., about 2×SSC, and 1% SDS, followed by a second wash at about 65° C. and about 0.1×SSC. Alternatively, high stringency conditions may include hybridization at about 42° C. and about 50% formamide, 0.1 mg,/mL sheared salmon sperm DNA, 0.5% of the amplified fragment (as described herein). If desired, RIM1 sequences may be isolated using the PCR "RACE" technique, or Rapid Amplification of cDNA Ends (see, e.g., Innis et al. (supra)). By this method, oligonucleotide primers based on an *Candida albicans* RIM1 sequence are oriented in the 3' and 5' directions and are used to generate overlapping PCR fragments. These overlapping 3'- and 5'-end RACE products are combined to produce an intact full-length cDNA. This method is described in Innis et al. (supra); and Frohman et al., *Proc. Natl. Acad. Sci. USA* 85:8998, 1988. Exemplary oligonucleotide primers useful for amplifying RIM1 homolog sequences include, without limitation:

A. GAATTAACCCTCACTAAAGGGAAARMGNGAYCAYATHAC (SEQ ID NO: 1); and

B. GTAATACGACTCACTATAGGGTGYTTYTTNARRTCYTG (SEQ ID NO: 2).

SDS, 5×SSPE, 1×Denhardt's, followed by two washes at room temperature and 2×SSC, 0.1% SDS, and two washes at between 55–60° C. and 0.2×SSC, 0.1% SDS.

In another approach, low stringency hybridization conditions for detecting RIM1 homologs having about 25% or greater sequence identity to the *Candida albicans* RIM1 gene described herein include, for example, hybridization at about 42° C. and 0.1 mg/mL sheared salmon sperm DNA, 1% SDS, 2×SSC, and 10% Dextran sulfate (in the absence of formamide), and awash at about 37° C. and 6×SSC, about 1% SDS. Alternatively, the low stringency hybridization may be carried out at about 42° C. and 40% formamide, 0.1 mg/mL sheared salmon sperm DNA, 0.5% SDS, 5×SSPE, 1× Denhardt's, followed by two washes at room temperature and 2×SSC, 0.1% SDS and two washes at room temperature and 0.5×SSC, 0.1% SDS. These stringency conditions are exemplary; other appropriate conditions may be determined by those skilled in the art.

If desired, RNA gel blot analysis of total or poly(A+) RNAs isolated from any fungus (e.g., those fungi described herein) may be used to determine the presence or absence of a RIM1 transcript using conventional methods. As an example, a northern blot of *Aspergillus nidulans* RNA is prepared according to standard methods and probed with a RIM1 gene fragment in a hybridization solution containing 50% formamide, 5×SSC, 2.5×Denhardt's solution, and 300 μg/mL salmon sperm DNA at 37° C. Following overnight hybridization, the blot was washed two times for ten minutes each in a solution containing 1×SSC, 0.2% SDS at 37° C. An autoradiogram of the blot is used to demonstrate the presence an RIM1-hybridizing RNA in the fungal RNA sample. A hybridizing band is taken as an indication that this fungus expresses a *C. albicans* RIM1 homolog. Isolation of this hybridizing transcript is performed using standard cDNA cloning techniques. Other fungal invasions may be evaluated and cloned in a similar fashion.

As discussed above, invasin oligonucleotides (e.g., oligonucleotides prepared from the *Candida albicans* RIM1 gene) may also be used as primers in amplification cloning strategies, for example, using PCR. PCR methods are well known in the art and are described, for example, in *PCR Technology,* Erlich, ed., Stockton Press, London, 1989; *PCR Protocols: A Guide to Methods and Applications,* Innis et al., eds., Academic Press, Inc., New York, 1990; and Ausubel et al. (supra). Primers are optionally designed to allow cloning of the amplified product into a suitable vector, for example, by including appropriate restriction sites at the 5' and 3' ends For each of the above sequences, N is A, T, G or C.

Alternatively, any fungal cDNA or cDNA expression library may be screened by functional complementation of an invasin mutant (for example, the RIM1 and AFL1 mutants described herein) according to standard methods described herein.

Confirmation of a sequence's relatedness to an invasin polypeptide may be accomplished by a variety of conventional methods including, but not limited to, functional complementation assays and sequence comparison of the homolog and its expressed product. In addition, the activity of the gene product may be evaluated according to any of the techniques described herein, for example, the functional or immunological properties of its encoded product.

Once an invasin homolog is identified, it is cloned according to standard methods and used for the construction of fungal expression vectors according to standard methods.

Interactin, Polypeptides

The isolation of invasin protein sequences also facilitates the identification of polypeptides which interact with the invasin proteins. Such polypeptide-encoding sequences are isolated by any standard two hybrid system (see, for example, Fields et al., Nature 1989, 340:245–246; Yang et al., Science 1992, 257:680–682; Zervos et al., Cell 1993, 72:223–232). For example, all or a part of the Tpk2 sequence may be fused to a DNA binding domain (such as the GAL4 or LexA DNA binding domain). After establishing that this fusion protein does not itself activate expression of a reporter gene (for example, a lacZ or LEU2 reporter gene) bearing appropriate DNA binding sites, this fusion protein is used as an interaction target. Candidate interacting proteins fused to an activation domain (for example, an acidic activation domain) are then co-expressed with the Tpk2 fusion in host cells, and interacting proteins are identified by their ability to contact the Tpk2 sequence and stimulate reporter gene expression. Tpk2-interacting proteins identified using this screening method provide good candidates for proteins that are involved in the acquired resistance signal transduction pathway. An example of this method is described herein (infra).

Isolatin Fungal Homologs which Complement *S. cerevisiae* Mutations

One use of the *S. cerevisiae* mutant strains is to screen for homologs in other fungi which can complement the *S. cerevisiae* mutations. Here we provide evidence for the efficacy of such an approach. We have identified the *C. albicans* homolog of INV8 (referred to as RIM1 (FIG. 5A;

SEQ ID NO: 3)). When the full length RIM1 was expressed from a plasmid in *S. cerevisiae* inv8 strains, the cells still showed an inv8 phenotype. However, the homologs of RIM1 (*S. cerevisiae* INV8, *Y. lipolytica* RIM101, and *A. nidulans* pacC) require proteolytic processing for activation. It is likely that the *S. cerevisiae* protease could not cleave *C. albicans* Rim1 (FIG. 5A; SEQ ID NO: 4). In support of this, a RIM1 gene truncated just prior to the protease cleavage site, was found to complement the inv8 phenotype in *S. cerevisiae* (FIG. 5B.) This makes it likely that a Rim1 protease exists in *C. albicans,* and this protease would be considered to be a homolog of INV14. Based on our discovery of the correlation between *S. cerevisiae* invasion and secondary metabolite production by other fungi, it is likely that many if not all of the *S. cerevisiae* INV genes will have homologs in diverse fungi. Indeed, INV5, INV9 and INV14 are predicted to encode proteins with high amino acid similarity to the products of the *A. nidulans* genes palA, palF, and palB, respectively. We found that the published sequence for the genomic region near INV9 contains several errors. The correct DNA sequence of INV9 (SEQ ID NO: 5) and the sequence of the predicted polypeptide (SEQ ID NO: 6) is shown in FIG. 6A–B. INV5/palA, INV9/palF, and INV 14/palB are required to activate Inv8/PacC in their respective organisms. Thus, these genes are structurally and functionally conserved genes. In addition, homologs of lNV9, INV11, and INV13 appear on the list of partially sequenced *C. albicans* genes (http://alces.med.umn.edu). An INV11 homolog in the fungus *Kluveromyces lactis* has also been partially sequenced (GENBANK locus: KLAJ9848), as have homologs of INV1 (GENBANK locus: SPBC3B9), INV13 (GENBANK locus: SPBC4B4) and INV15 (GENBANK locus: SPAC1B3) in the fungus *Schizosaccharomyces pombe.* An STP22 homolog has been identified in the fungus *Saccharomyces carlsbergensis* (GENBANK locus: SCZ86109). Of the 12 cloned genes in the INV pathway, six (INV5, INV8, and INV12–15) have obvious structural homologs outside the fungal kingdom. The existence of INV homologs in a wide variety of fungi, including the pathogenic fungus, *C. albicans,* and one that produces the important secondary metabolite penicillin, *A. nidulans,* underscores the potential utility of manipulating these genes and/or their activities to affect both pathogenesis and secondary metabolite production in diverse fungi. Additional homologs can be isolated by expressing genes from fungal cDNA or genomic libraries in *S. cerevisiae* mutant strains and selecting for those transformants in which the mutant phenotype is complemented or enhanced.

Mutating Genes in Other Fungi to Determine Their Roles in Invasion

Following isolation of any specific homolog of a *S. cerevisiae* gene involved in invasion from any fungal species, we can determine the role of that gene in pathogenesis or invasion by that fungus. Any such gene that activates or increases invasion is also likely to activate or increase virulence. Deletion or inactivation of the function of these genes would likely reduce the virulence of that fungal strain. The following gene deletion example utilizes the *C. albicans* RIM1 gene from the previous section.

We tested whether the *C. albicans* RIM1 gene was required for invasive hyphal growth in *C. albicans*. A homozygous rim1/rim1 deletion was created. The *C. albicans* rim1/rim1 mutant does not form invasive hyphae in the presence of serum on agar at 37° C., while nonmutant *C. albicans* does (FIG. 7). The virulence of the mutated strains can be determined using a variety of animal models. One model of systemic infection is described as an example. To test the relative virulence (infectivity) of a mutant strain of Candida compared to a normal "wild-type" strain, mutant and normal Candida cells are injected into the tail veins of separate healthy mice. The mice are then observed for a period of two weeks to one month. The relative numbers of mice killed by the mutant versus normal Candida provides an index of virulence (see Lo et al., Cell 1997, 90: 939–949). Furthermore, any fungal gene that inhibits or decreases invasion is also likely to inhibit or decrease secondary metabolite production. Deleting or disrupting the function of any such gene is likely to increase secondary metabolite production. Genetic engineering methods, including transformation and homologous recombination techniques, are practiced in many fungi (Punt and van den Hondel, Methods Enzymol. 1992, 216:447–457; Timberlake and Marshall, Science, 1989, 244:1313–1317; Fincham, Microbiol Rev. 1989, 53:148–170). Gene deletion techniques are currently practiced in many fungi, including, but not limited to, *Candida albicans* (Fonzi and Irwin, Genetics 1993, 134: 717–728), *Ustilago maydis* (Fotheringham and Hollman, Mol. Cell Biol. 1989, 9:4052–4055; Bolker et al., Mol. Gen. Genet. 1995, 248:547–552), *Yarrowia lipolytica* (Neuveglise et al., Gene 1998, 213:37–46; Chen et al., Appl. Microbiol. Biotechnol. 1997, 48:232–235; Cordero et al., Appl. Microbiol. Biotechnol. 1996, 46:143–148), *Acremonium chrysogenum* (Skatrud et al., Curr. Genet. 1987, 12:337–348; Walz and Kuck, Curr. Genet. 1993, 24:421–427), *Magnaporthe grisea* (Sweigard et al., Mol. Gen. Genet. 1992, 232:183–190); Kershaw et al., EMBO J. 1998, 17:3838–3849), *Histoplasma capsulatum* (Woods et al., J. Bacteriol. 1998, 180:5135–5143) and Aspergillus sp. (Miller et al., Mol. Cell Biol. 1985, 5:1714–1721; de Ruiter-Jacobs et al., Curr. Genet. 1989, 16:159–163; Gouka et al., Curr. Genet. 1995, 27:536–540; van den Hombergh et al., Mol. Gen. Genet. 1996, 251:542–550; D'Enfert, Curr. Genet. 1996, 30:76–82; Weidner et al., Curr. Genet. 1998, 33:378–385).

This gene deletion technique allows for the selection of fungal homologs which give the strongest phenotypes, as well as those which are invasion specific. Some of the gene disruptions will likely produce nonpathogenic fungi. These genes and the encoded proteins are excellent candidates to target with compounds. Other disruptions will likely produce hyperinvasive fungi. The mutation of these genes in fungi such as Aspergillus sp., Penicillium sp., *Acremonium chrysogenum, Yarrowia lipolytica,* and *Phaffia rhodozyma* should lead to increased production of secondary metabolites of commercial value, such as beta-lactam antibiotics and their derivatives, or anti-hypercholesterolemic agents such as the statins.

A System to Increase Production of Secondary Metabolites

Fungi secrete secondary metabolites in order to produce an environment favorable for their survival. These metabolites have also been shown to have a great number of commercial uses. We have discovered a correlation between secondary metabolite production and the regulation of invasion. The *A. nidulans* pacC gene, involved in regulation of the penicillin production, has a homolog in both *S. cerevisiae* and *C. albicans* which has a role in invasion. The *A. nidulans* genes palA, palD, and palF, involved in regulation of penicillin production, also have homologs in *S. cerevisiae* that are required for invasion. In addition, as described above, we have identified the homolog of pacC in *C. albicans* (RIM1) and showed that it is also necessary for invasion. Similarly, many of the nutritional conditions that induce substrate invasion by *S. cerevisiae* also lead to increased penicillin production in *A. nidulans.* For example, growth in the presence of limiting amounts of ammonia is important both for pseudohyphal growth in *S. cerevisiae* and production of penicillin in *A. nidulans* (see Gimeno et al., supra, and Brakhage, A. A., Micro. Mol. Biol. Rev. 1998, 62: 547–585). Many of the genes we have shown to regulate invasion, as well as expression from the FLO11 promoter (infra), will also regulate production of secondary metabolites in fungi such as Aspergillus sp., Penicillium sp., *Acremonium chrysogenum, Yarrowia lipolytica* and *Phaffia rhodozyma*. This knowledge can be used to produce fungal strains which produce greater amounts of these secondary metabolites, many of which are of great commercial value.

One example of how genetic manipulation can increase secondary metabolite production utilizes the fungal invasion-inhibiting gene, HOG1. We have shown that HOG1 is a negative regulator of haploid invasion and pseudohyphal growth in *S. cerevisiae*. Mutating or deleting HOG1 in *S. cerevisiae* produces a transgenic strain which invades its substrate in conditions in which a wild-type strain does not. Decreasing the activity of the Hog1 protein in fungal species such as Aspergillus sp., Penicillium sp, *Acremonium chrysogenum, Yarrowia lipolytica* and *Phaffia rhodozyma*, results in an increased production of secondary metabolites through a de-repression of the signal transduction pathway. There are a variety of ways to decrease protein activity. One method is to delete the entire HOG1 gene or a portion thereof, using homologous recombination techniques known to be applicable in fungi as described herein. Similarly, mutagenesis of genes could also lead to decreased protein activity. Another method would be to apply a gene or compound which, directly or indirectly, inhibits the expression of HOG1 or the activity of Hog1. These genes and compounds can be isolated using screening techniques described herein. The methods described for HOG1 are equally applicable to any fungal anti-invasion gene, including, but not limited to, GRR1, IRA1, BEM2, TPK3, SFL1, SSD1, RIM15, CDC55, SWI4, and ELM1.

A second mechanism to increase production is to increase the activity of a fungal invasion-promoting gene, such as homologs of INV8 or any other fungal invasion-promoting gene. One method is to express such a gene from a constitutively active promoter. Expression systems, such as those which drive expression of genes from promoter sequence from either the *Aspergillus nidulans* gpdA gene, the *Acremonium chrysogenum* ipnS gene, or the *Penicillium chrysogenum* phoA gene, are well-known to those skilled in the art (Skatrud et al., Curr. Genet. 1987, 12:337–348; Kolar et al., Gene 1988, 62:127–134; de Ruiter-Jacobs et al., Curr. Genet. 1989, 16:159–163; Smith et al., Gene 1988, 114:211–216; Graessle et al., Appl. Environ. Microbiol. 1997, 63:753–756).

Another method to increase activity of a fungal invasion-promoting gene is to genetically alter the fungal invasion gene, either through the introduction of an activating mutation or by creating fusions to other genes that result in increased activity. The fusion proteins are preferably constitutively active. A third method is to mutate the fungal invasion gene such that the activity of the encoded protein is increased. For example, *S. cerevisiae* Inv8 and its homolog, PacC, require proteolyic cleavage for transcriptional activating properties. We have shown that this cleavage is required for the nuclear localization of Inv8. Inability to truncate Inv8 results in its accumulation in the cytoplasm (FIG. 8). These data suggest that activation of Inv8 and its homologs is likely to be a consequence of allowing the protein to gain access to its target genes in the nucleus. Thus, truncation of Inv8 or PacC caused by the introduction of a stop codon upstream of the coding sequence for the protease cleavage site would create a constitutively active transcription factor. Another method is to apply a compound which, directly or indirectly, increases the expression of INV8 or the activity of Inv8. These compounds can be isolated using screening techniques described herein. *S. cerevisiae* INV8 is homologous to *Y. lipolytica* RIM101, and pacC from *A. nidulans, A. niger*, and *P. chrysogenum*. pacC is known to directly regulate penicillin production; penicillin production is regulated by the activated form of the transcription factor. Thus, increased PacC activity using any of the described methods will lead to increased penicillin production.

The FLO11 Promoter is a Reporter of Fungal Invasion

The cell surface protein Flo11 has been reported to be required for invasive and filamentous growth (Lambrechts et al., 1996; Liu et al., 1996; Lo and Dranganis, 1996; Lo and Dranganis, 1998; Flo11 is referred to as Muc1 in *S. cerevisiae* var. diastaticus). The FLO genes encode proteins required for cell-cell adhesion (Teunissen and Steensma, 1995). The MAP kinase pathway, involving four protein kinases (Ste20, Ste11, Ste7, and Kss1), regulates the activity of the transcription factor Ste12/Tec1. One of the genes regulated by this signal transduction cascade is FLO11.

We have discovered that FLO11 is a downstream target for other signal transduction pathways that regulate filamentous growth in diploids and invasion in haploids. While it was known that one pathway which regulated these phenotypes also regulated FLO11 expression, it was surprising that FLO11 appeared to be under such complex regulation by several signal transduction pathways. These findings are outlined below.

An example of another signal transduction cascade which regulates FLO11 expression is the cAMP/PKA pathway. The evidence which implicated FLO11 as a target of the cAMP pathway follows. Since both the MAPK pathway and the cAMP/PKA pathway are activated for filamentation by the same activator, Ras2, analysis of the distinct role of cAMP on filamentous growth requires the ability to activate the PKA branch independently of Ras. To achieve this goal, we constructed a strain (ras1 ras2 pde2) lacking both RAS genes (RAS1 and RAS2) and the high-affinity cAMP phosphodiesterase, PDE2. Since Ras1 and Ras2 are required for the activation of adenylate cyclase, Cyr1 and PDE2 encodes the phosphodiesterase required for cAMP hydrolysis, a ras1 ras2 pde2 strain is impaired in the synthesis and breakdown of cAMP. Such a strain should be dependent upon exogenous cAMP for induction of the A kinase and, as no Ras-induced signal can be transmitted to the MAPK cascade, the effects of cAMP on filamentation should be independent of the Ras/MAPK signal.

The ras1 ras2 pde2 strain (SR957) requires cAMP for growth on YPD (yeast extract, peptone, dextrose), but grows without cAMP on SC (synthetic complete), SLAD (synthetic low ammonia dextrose), and YNB (yeast nitrogen base), media where it displays hyper-accumulation of glycogen, indicative of low cAMP levels. We presume that the ability of this triple mutant to grow without added cAMP, as has been observed by others (Nikawa et al., 1987), results from basal cyclase activity that is sufficient to provide internal cAMP. In support of this notion, we observed that growth of our ras1 ras2 pde2 strain depended upon a functional cyclase (CYR1) gene.

A diploid ras1 ras2 pde2 (SR959) strain grows on SLAD medium without cAMP but does not form pseudohyphae. However, on SLAD medium containing cAMP, the strain is extremely filamentous. Moreover, the addition of cAMP leads not only to induction of filamentation, but also to invasion of the substrate. In the presence of cAMP, the ras1 ras2pde2 strain (SR959) is invasive on all media tested (YPD, SC, SLAD). Since invasive growth is usually observed with haploid strains on YPD, both the cell type signal and the nutritional signal can be bypassed by high cAMP levels in the cell.

To determine whether cAMP induces filamentation by activating the MAPK pathway, we measured the expression of the Kss1 MAPK pathway-specific reporter FG::Ty1-lacZ (Mosch et al., supra) in ras1 ras2,pde2 strains grown on SLAD plates containing concentrations of cAMP that induce filamentation. The level of expression of the FG::Ty1-lacZ reporter in the ras1 ras2 pde2 strain (SR959) was not altered by these cAMP levels. Moreover, cAMP induced filamentation in a ste12 ras1 ras2 pde2 deletion strain (SR1088), indicating that the cAMP/PKA pathway acts in parallel with the MAPK pathway.

We demonstrated the induction of FLO11 mRNA by cAMP in the ras1 ras2 pde2 strain, but not in a wild-type background. The FLO11 transcript was undetectable when the triple mutant strain is grown without cAMP and strongly induced in the presence of 2 mM cAMP. Expression of FLO1, which encodes Flo1, another cell surface protein required for flocculation and 26% identical to Flo11, is only induced 1.4 fold under identical conditions. This result shows that the strong induction of FLO11 is not a general feature of all flocculation genes. The correspondence between cAMP induction of FLO11 and the morphological changes observed when the cells are grown in the presence of cAMP is further supported by the phenotype of the FLO11 deletion; in the flo11 ras1 ras2pde2 strain (SR1121), cAMP fails to induce either invasion or filamentation. These data suggest that FLO11 is a key target of a cAMP-dependent signaling pathway, one that is required for the induction of invasive and filamentous growth.

The enhanced FLO11 transcription in the presence of cAMP is correlated with a change in cellular morphology. Cells grown in liquid SC with 2 mM cAMP show pseudohyphal-like chains of cells, whereas the majority of cells grown in liquid SC without CAMP are either single cells or cells with a single bud. The effect of cAMP on cell-cell attachment is much more pronounced than the effect of the cyclic nucleotide on cell elongation.

The use of the FLO11 promoter as a reporter of invasion and filamentous growth appears to be universal. As shown in FIG. 9, the FLO11 promoter is an excellent reporter for invasion and pseudohyphal growth. For mutants that reduce invasion or pseudohyphal growth, there was a direct correlation between FLO11 expression and invasion/pseudohyphal growth for afl1, ste12, tec1, flo8, inv8, ras2, tpk2, phd1, phd2, inv6, inv7, whi3, dhh1, mep2, ptc1, mcm1, inv1, inv13, and inv14. In addition, hog1, grr1, ira1, tpk3, and sfl1 mutants, which exhibited increased invasion/pseudohyphal growth, also displayed increased FLO11 expression. For example, FLO11 is transcriptionally regulated by both Tpk2 and Sfl1. tpk2 mutants showed a 10-fold reduction in FLO11 expression, whereas tpk3 mutants had a threefold elevation. The levels of FLO11 mRNA were also reduced 10-fold in tpk2 tpk3 double mutants. FLO11 mRNA levels were also increased threefold in an sfl1 mutant and were similarly increased in an sfl1 tpk2 double mutant. The levels of FLO11 mRNA in the sfl1 tpk3 double mutant exceeded that of either single mutant.

Not only is FLO11 an excellent reporter of pseudohyphal growth and invasion, it is also central to invasion and pseudohyphal growth. sfl1 flo11 haploid mutant strains were defective for invasive growth on rich medium, and sfl1 flo11 homozygous diploid mutants were defective for pseudohyphal development. Thus, flo11 loss of function blocked the hyperinvasive and hyperfilamentous phenotypes of sfl1 loss of function. However, the defect of the sfl1 flo11 double mutant was not as severe as that of the flo11 single mutant, suggesting that FLO11 is not the only downstream target of Sfl1 involved in pseudohyphal development and haploid invasion.

It is reasonable to assume that many other genes that have been placed in signal transduction pathways, including the genes shown in FIG. 10, will also be required for FLO11 expression. Based on these results, and our recent identification of a number of additional genes that regulate invasion (and quite likely FLO11 expression), we have constructed a wiring diagram for the genetic circuitry that regulates FLO11 (FIG. 10). These genes, listed in Table 1, all represent candidate targets for novel antifungal agents that act by blocking invasion and/or dimorphic growth.

To determine how much of this 5' region of FLO11 was required for the regulated expression of FLO11, we examined the expression of plasmid-based FLO11::lacZ reporter constructs containing deletions in this non-coding region. Fourteen serial 200 bp deletions were constructed that span the region 2800 bases (bp −2800) upstream from the FLO11 initiation codon. A FLO11-lacZ reporter plasmid was constructed by amplifying the 3 kb region 5' of the ATG by PCR using primers containing a BglII site at the end and cloning into YEp355. (Sequences of primers used are 5'-CGCACACTATGCAAAGACCGAGATCTTCC-3' (SEQ ID NO: 7) and 5'-GAAGATCTTCTCCACATACCAATCACTCG-3' (SEQ ID NO: 8). The 14 individual deletions in this reporter were constructed by primer overlap method using a KS+-Bluescript plasmid containing the 3 kb FLO11-promoter region (subcloned from YEp355-FLO11::lacZ as EcoRI/HindIII fragment). After mutagenesis the partially deleted flo11-nn promoter sequence was recloned into YEp355. The primers used for this purpose were:

```
                                 -3'
           #1F  5'-CAAGCATTTACGTTACTGCGAAAATCCATATACGCACACT-3'    (SEQ ID NO: 9)

#1R  5'-AGTGTGCGTATATGGATTTTCGCAGTAACGTAAATGCTTG-3'    (SEQ ID NO: 10)

#2F  5'-TGATGAGGTAACCTTTACAACTCTCTTCTAGTTCAAGAAC-3'    (SEQ ID NO: 11)

#2R  5'-GTTCTTGAACTAGAAGAGAGTTGTAAAGGTTACCTCATCA-3'    (SEQ ID NO: 12)

#3F  5'-TTTCAATTCAATGGATTTGGAATGTCATAGAGTTACCAAT-3'    (SEQ ID NO: 13)

#3R  5'-ATTGGTAACTCTATGACATTCCAAATCCATTGAATTGAAA-3'    (SEQ ID NO: 14)
```

-continued

| | | |
|---|---|---|
| #4F | 5'-ATTTCTGCCTATACTCTTAAAGGTATTCGTTTGTTTACTA-3' | (SEQ ID NO: 15) |
| #4R | 5'-TAGTAAACAAACGAATACCTTTAAGAGTATAGGCAGAAAT-3' | (SEQ ID NO: 16) |
| #5F | 5'-TTGGGGCTAAGAATGGACACAGATCAGTCATTCATGTTGT-3' | (SEQ ID NO: 17) |
| #5R | 5'-ACAACATGAATGACTGATCTGTGTCCATTCTTAGCCCCAA-3' | (SEQ ID NO: 18) |
| #6F | 5'-GGGTGTGCCTGGAAAGTTCATTCCCTTTTCTTTTTCTTTG-3' | (SEQ ID NO: 19) |
| #6R | 5'-CAAAGAAAAAGAAAAGGGAATGAACTTTCCAGGCACACCC-3' | (SEQ ID NO: 20) |
| #7F | 5'-CAAAACTTTAGGAATACCGGAAATTAAGGTTTTTTTCTTC-3' | (SEQ ID NO: 21) |
| #7R | 5'-GAAGAAAAAAACCTTAATTTCCGGTATTCCTAAAGTTTTG-3' | (SEQ ID NO: 22) |
| #8F | 5'-CGAATGTGAATGCGCTAATCTTGTGTGCCTACGCCAGCCC-3' | (SEQ ID NO: 23) |
| #8R | 5'-GGGCTGGCGTAGGCACACAAGATTAGCGCATTCACATTCG-3' | (SEQ ID NO: 24) |
| #9F | 5'-AGACAAAAAATAGGAAAAGTGGTATTTCCACCACATGAAA-3' | (SEQ ID NO: 25) |
| #9R | 5'-TTTCATGTGGTGGAAATACCACTTTTCCTATTTTTTGTCT-3' | (SEQ ID NO: 26) |
| #10F | 5'-TTAGTGCGGAATACTTTCCTTTAATTAGTGATGGTTCTCA-3' | (SEQ ID NO: 27) |
| #10R | 5'-TGAGAACCATCACTAATTAAAGGAAAGTATTCCGCACTAA-3' | (SEQ ID NO: 28) |
| #11F | 5'-CAGTGCTTTCAACACCTTTTATTCTCATCGAGAGCCGAGC-3' | (SEQ ID NO: 29) |
| #11R | 5'-GCTCGGCTCTCGATGAGAATAAAAGGTGTTGAAAGCACTG-3' | (SEQ ID NO: 30) |
| #12F | 5'-GTAGCTGAAAAGTCCATCTACATCTGTGTGCCATGTCAGA-3' | (SEQ ID NO: 31) |
| #12R | 5'-TCTGACATGGCACACAGATGTAGATGGACTTTTCAGCTAC-3' | (SEQ ID NO: 32) |
| #13F | 5'-GAGATTATCTTGGGATCTATTCGAATTATGAATGATACTA-3' | (SEQ ID NO: 33) |
| #13R | 5'-TAGTATCATTCATAATTCGAATAGATCCCAAGATAATCTC-3' | (SEQ ID NO: 34) |
| #14F | 5'-GTTTTGGCTCAATGGGACCGTTCACAAATTTACGGCTAAT-3' | (SEQ ID NO: 35) |
| #14R | 5'-ATTAGCCGTAAATTTGTGAACGGTCCCATTGAGCCAAAAC-3' | (SEQ ID NO: 36) |

The resulting 14 plasmids for the deletion series were transformed into strain 10560-2B. At least three independent clones were tested using filter assays for equivalent expression of β-galactosidase. Diploid strains were created by mating of the respective 10560-2B flo11-nn transformant with strain 10560-SB by selection on YNB containing only leucine as a supplement.

The 14 plasmids containing the 400 bp sequence elements were transformed into 10560-2B, L5795, L5816, L6149, L6150 and SR957. At least three independent clones were tested using filter assays for equivalent expression of β-galactosidase. Filter assays were used to test the effect of α-factor (5 μM).

The large number of FLO11 promoter elements and multiple conditions that affect those elements required some economy in the experimental design. The measurement of β-galactosidase from our plasmid-based reporter containing each of these elements permitted the rapid construction of strains and reproducible measurement of reporter activity. We confined the analysis to selective media so that the strains retained the plasmids. Our β-galactosidase assays show in general a higher activity for haploid strains than for diploid strains. For rich medium this result is in agreement with that found previously when FLO11 expression was monitored by measurement of steady state mRNA-levels. When we measure FLO11::lacZ after 24–26 h (post diauxic growth) or on SLAD medium, haploid cells show an induction of more than 10 fold and diploid cells, 5 fold induction. This large induction of FLO11::lacZ for haploid cells on SLAD was not observed in the experiments where FLO11 mRNA was measured. This discrepancy could be due either to a difference in the stability of mRNA vs. protein or the differences in the times at which the cultures were sampled. The expression of FLO11 as measured by either method is extremely sensitive to growth conditions and growth phase.

Total RNA was prepared using hot acid phenol and northern blots were performed as described in Ausubel et al., (supra). Strains deleted for ras1 ras2 pde2 were pre-grown in SC+1 mM cAMP to OD600=1.0. The cells were washed twice using SC and diluted to an OD600=0.3 into fresh SC medium or SC medium+2 mM cAMP. The cells were grown to OD600=1.0 and harvested. 10–15 μg of RNA were separated on a formaldehyde containing agarose gel. For hybridization to FLO11 mRNA, a probe corresponding to bp 3502–4093 of the FLO11 ORF was used.

Cells for β-galactosidase assays of FG::TyA-lacZ were incubated on SLAD-plates for three days; cells for FLO11::lacZ expression studies were grown in the respective liquid media and quantitated according to Mosch et al. (supra).

Cells for quantitation of FLO11::lacZ expression in exponential growth phase were inoculated from confluent 20 h grown cultures 1:20 in fresh medium and grown for 4–6 h. Cells for quantitation of FLO11::lacZ expression after the post-diauxic shift were grown for 24–26 h. The same cultures were used to inoculate the exponentially growing cultures. Cells for quantitation of FLO11::lacZ expression in SLAD-medium were pre-grown for 20 h in SC-medium, washed twice with 2% glucose, diluted 1:5 into SLAD-medium and grown for 4–6 hours. For detection of cAMP induced FLO11 promoter segments strain SR957 harboring the individual plasmids was grown overnight in selective medium containing 1 mM cAMP, transferred to media containing no cAMP for 10 h and split into 2 cultures containing 2 mM cAMP or no cAMP and grown for 4 h before harvesting.

Expression of the deletions was assayed in haploid and diploid strains. Since FLO11 expression varies with growth phase of the cells, we analyzed exponentially growing cells on SC, cells grown on SC until the glucose had been depleted (post-diauxic), and cells on SLAD, a medium that is high in glucose and low in nitrogen.

Enzymatic assays on the individual FLO11::lacZ promoter deletions reveals an unusually long promoter with many sites. In subsequent sections, a site is tentatively assigned as an upstream repression site (URS) if its deletion leads to at least 3-fold enhanced expression of lacZ, and as an upstream activation site (UAS) if its deletion leads to at least 30% reduced expression.

Analysis of cis-acting elements by enzymatic assays of the individual flo11-lacZ promoter deletions reveals that the intact FLO11 promoter is highly repressed. The deletions define at least nine URS elements whose activity depends on state of growth, nutrient conditions, and cell type. One of the URS elements is defined by flo11–14 (bp-2600–2800), showing that cis-acting elements are present at least 2800 bases from the putative FLO11 coding region. In general, haploid strains show stronger repression than diploid strains.

A clear way to visualize the activity of the sites of repression is by comparison of the lacZ activity for each of the conditions with that of a haploid grown on SLAD. This comparison reveals URS elements within flo11-4,-5,-7,-8,-12,-13, and flo11-14. A subset of these elements is key to repression on all media, but the strongest effect is in haploids grown on SLAD. Haploid-specific effects are found for deletions flo11-4,-10,-11,-12, and flo11-13. Clearly, there are sites in flo11-4,flo11-12, and flo11-13 that function in the haploid-specific nitrogen repression of FLO11.

There are other differences between haploid and diploid strains, the most notable of which being: 1) in diploids on SC (exponential growth), flo11-4 has a 2-fold reduced expression level, whereas in haploids it has 33-fold elevated expression; 2) in diploids after the diauxic shift, flo11-11 has a 3-fold reduced level whereas in haploids it has 12-fold elevated expression. In diploid cells, flo11-4,flo11-10, and flo11-11 act as UAS elements. flo11-5 is a strongly nitrogen-regulated site in both haploids and diploids.

Deletion analysis also revealed sequence elements required for expression of FLO11. Under all conditions tested, flo11-6 had a dramatic reduction in expression, suggesting that the sequence deleted in flo11-6 (−1200 to −1000) contained a strong UAS. Furthermore, flo11-1, flo11-2, and flo11-3 show consistently lower activity, as compared to the wild-type FLO11-lacZ reporter construct, identifying these as UAS elements in the FLO11 promoter. The reduced expression of flo11-1 is likely to be a consequence of the deletion of the TATAA region in this construct.

We made two flo11 promoter mutations in the chromosome at the FLO11 locus. In one, flo11-16, we deleted virtually the entire promoter region (from −150 to −2947). In the other, we replaced the entire wild-type promoter with flo11-6. Chromosomal deletion of the FLO11 promoter was done by replacing base pairs −2947 to −150 with URA3 (sequences of primers used:

5'-ACCACAACATGACGAGGGATAATAACTGAT GAATAGGGTGCTTTTTATAC

TCTGTGCGGTATTTCACACC-3' (SEQ ID NO: 37) and 5'-TAAGGAGTCGTACCGCCAACTAAATCTGAATAA CAATTTGGCTGCTAGAA GCAGATTGTACTGAGAGTGC-3'; SEQ ID NO: 38), resulting in flo11-16 (SR 1172) To generate flo11-6 in the chromosomal FLO11 promoter region, the URA3 gene was replaced by transformation with EcoRI/HindIII digested KS+flo11-D6 and selection on 5-FOA to yield deletion of base pairs −1000 to −1200 (SR 1174).

A strain carrying either flo11-16 or flo11-6 is completely defective in haploid invasive growth and, as diploids (e.g., flo11-6flo11-6), show severely reduced filamentation. The haploid invasion defect is as severe as that of a deletion of the FLO11 coding region. The results with flo11-6 support our conclusions based on the data from the lacZ plasmid constructs, which identified the segment deleted in the flo11-6 construct as a critical UAS for FLO11 expression.

In a second approach to identify UAS elements of the FLO11 promoter, we designed 14 individual sequence elements of approximately 400 base pairs, to test activation of a lacZ reporter fused to a basal transcriptional unit (FIG. 11). To determine UAS-sequence elements, 14 individual 400 bp elements, overlapping by 200 bp were amplified by PCR and cloned into pLG669Z. This vector contains one codon of the CYC1 gene fused to the lacZ gene, and the fused gene is preceded by 1100 nucleotides that lie upstream from CYC1. The promoter fragment has XhoI restriction sites at positions −683 and −249. The XhoI fragment has been excised and replaced with a fragment from the FLO11 promoter. The fragments correspond to the following positions relative to the start codon of FLO11: −1 to −421 (FLO11-2/1), −181 to −618 (FLO11-3/2), −380 to −819 (FLO11-4/3), −580 to −1017 (FLO11-5/4), −778 to −1219(FLO11-6/5), −980 to −1420 (FLO11-7/6), −1181 to −1619 (FLO11-8/7), −1380 to −1819 (FLO11-9/8), −1572 to −2019 (FLO11-10/9), −1780to −2219 (FLO11-11/10), −1980 to −2419 (FLO11-12/11), −2180 to −2619 (FLO11-13/12), −2380 to −2819 (FLO11-14/13), −2580 to −2983 (FLO11-15/14). For cloning purposes, a restriction site (XhoI) was introduced at the 5' end of the PCR-primers. The primers used for this purpose were:

| | | |
|---|---|---|
| #1R | 5'-CCGCTCGAGAGTGTGCGTATATGGATTTT-3' | (SEQ ID NO: 39) |
| #2F | 5'-CCGCTCGAGTGATGAGGTAACCTTTACAA-3' | (SEQ ID NO: 40) |
| #2R | 5'-CCGCTCGAGGTTCTTGAACTAGAAGAGAG-3' | (SEQ ID NO: 41) |
| #3F | 5'-CCGCTCGAGTTTCAATTCAATGGATTTGG-3' | (SEQ ID NO: 42) |
| #3R | 5'-CCGCTCGAGATTGGTAACTCTATGACATT-3' | (SEQ ID NO: 43) |
| #4F | 5'-CCGCTCGAGATTTCTGCCTATACTCTTAA-3' | (SEQ ID NO: 44) |
| #4R | 5'-CCGCTCGAGTAGTAAACAAACGAATACCT-3' | (SEQ ID NO: 45) |
| #5F | 5'-CCGCTCGAGTTGGGGCTAAGAATGGACTT-3' | (SEQ ID NO: 46) |
| #5R | 5'-CCGCTCGAGACAACATGAATGACTGATCT-3' | (SEQ ID NO: 47) |

-continued

| | | |
|---|---|---|
| #6F | 5'-CCGCTCGAGGGGTGTGCCTGGAAAGTTCA-3' | (SEQ ID NO: 48) |
| #6R | 5'-CCGCTCGAGCAAAGAAAAAGAAAAGGGAA-3' | (SEQ ID NO: 49) |
| #7F | 5'-CCGCTCGAGCAAAACTTTAGGAATACCGG-3' | (SEQ ID NO: 50) |
| #7R | 5'-CCGCTCGAGGAAGAAAAAAACCTTAATTT-3' | (SEQ ID NO: 51) |
| #8F | 5'-CCGCTCGAGCGAATGTGAATGCGCTAATC-3' | (SEQ ID NO: 52) |
| #8R | 5'-CCGCTCGAGGGGCTGGCGTAGGCACACAA-3' | (SEQ ID NO: 53) |
| #9F | 5'-CCGCTCGAGAGACAAAAAATAGGAAAAGT-3' | (SEQ ID NO: 54) |
| #9R | 5'-CCGCTCGAGGTAGCAGGTTTCATGTGGTG-3' | (SEQ ID NO: 55) |
| #10F | 5'-CCGCTCGAGTTAGTGCGGAATACTTTCCT-3' | (SEQ ID NO: 56) |
| #10R | 5'-CCGCTCGAGTGAGAACCATCACTAATTAA-3' | (SEQ ID NO: 57) |
| #11F | 5'-CCGCTCGAGCAGTGCTTTCAACACCTTTT-3' | (SEQ ID NO: 58) |
| #11R | 5'-CCGCTCGAGGCTCGGCTCTCGATGAGAAT-3' | (SEQ ID NO: 59) |
| #12F | 5'-CCGCTCGAGGTAGCTGAAAAGTCCATCTA-3' | (SEQ ID NO: 60) |
| #12R | 5'-CCGCTCGAGTCTGACATGGCACACAGATG-3' | (SEQ ID NO: 61) |
| #13F | 5'-CCGCTCGAGGAGATTATCTTGGGATCTAT-3' | (SEQ ID NO: 62) |
| #13R | 5'-CCGCTCGAGTAGTATCATTCATAATTCGA-3' | (SEQ ID NO: 63) |
| #14F | 5'-CCGCTCGAGGTTTTGGCTCAATGGGACCG-3' | (SEQ ID NO: 64) |
| #14R | 5'-CCGCTCGAGATTAGCCGTAAATTTGTGAA-3' | (SEQ ID NO: 65) |
| #15F | 5'-CCGCTCGAGCTCCACATACCAATCACTCG-3' | (SEQ ID NO: 66) |
| #15R | 5'-CCGCTCGAGTAGTTAAACGTTTTATTAGC-3' | (SEQ ID NO: 67) |

This reporter construct series identified UAS elements in the segments FLO11-2/1 and FLO11-3/2 that overlap between bp −200 and −400, FLO11-6/5 and FLO11-7/6 that overlap between bp −1200 and −1000, as well as FLO11-10/9 and FLO11-11/10 that overlap between bp −2000 and −1800. These sequence elements show a more than 2-fold increase in β-galactosidase activity as compared to the reporter plasmid containing the basal transcriptional unit but without any insert. The activity of FLO11-2/1, FLO11-3/2 and FLO11-11/10 are induced in post-diauxic cells, leading to an induction of up to 200-fold. These results suggested that elements FLO11-2, FLO11-3, and FLO11-11 are required for FLO11 expression in later stages of growth. Taken together with the deletion analysis, these data suggested that there were at least four UAS elements in the FLO11 promoter. The FLO11 promoter has extensive homologies to the promoter regions of the MUC1, STA1, STA2, and STA3 genes from S. cerevisiae var. diastaticus.

The types of promoter analyses described above, in combination with the series of mutant strains identified which have defects in diploid filamentous growth or haploid invasion, allows for the identification of trans-acting elements and the regions of the FLO11 promoter that are targeted by them. In one example, we transformed the 14 individual 400 bp sequence elements into strains deleted for FLO8, STE12, TEC1, or for both STE12 and TEC1.

Deletion of FLO8 led to a severe reduction in the expression of FLO11-6/5 and FLO11-7/6 in both exponential (8-fold and 4-fold reduction, respectively) and post-diauxic growth (5-fold for both elements). These elements are also induced by high cAMP levels. FLO8 function is also required for maximum expression of FLO11-3/2 and FLO11-8/7 in post-diauxic growth phase, but not in exponential growth, a result suggesting that Flo8 may function differently depending upon nutrient conditions.

Deletion of STE12 had a stronger effect in exponentially-growing cells than in post-diauxic cells. In exponentially-growing cells lacking Ste12, the FLO11-6/5, FLO11-10/9, and FLO11-11/10 segments showed at least a 3-fold reduction in expression. In post-diauxic cells, only FLO11-10/9 showed reduced expression in an STE12 deletion strain.

Deletion of TEC1 had significant effects on expression of the FLO11 insertion reporter series, but the reduction could be observed only in exponentially-growing cells and was less severe than that observed for strains deleted for STE12 or FLO8. This observation agrees with the northern analysis of the intact FLO11 promoter, where FLO11 mRNA levels showed less of a reduction in a strain deleted for TEC1 (L6149) than it did in strains deleted for STE12 (L5795) or FLO8 (L5816). FLO11-6/5, FLO11-10/9, and FLO11-12/11 were dependent upon TEC1 in exponentially-growing cells. Deletion of TEC1 in a ste12 strain showed a modest reduction in the expression of FLO11-10/9 as compared to the single mutant strains. However, since the deletion of STE12 led to a >10-fold stronger effect than deletion of TEC1, this result may indicate a Tec1-independent role for Ste12 at this site.

Our results suggest that Flo8 and Ste12/Tec1 act via multiple sites in the FLO11 promoter that are largely non-overlapping. The strongest effect of Flo8 and Ste12, both in exponential and post-diauxic cells, was observed with two distinct sequence elements of the FLO11 promoter. Flo8 acted on the sequence element defined by flo11-6 (bp −1200 to −1000),whereas Ste12 acted on FLO11-10/9 (bp −1800 to −1600). FLO11-12/11 and FLO11-10/9 were targeted both by Tec1 and Ste12. The existence of spatially distinct sites for different transcription factors provides strong evidence in support for the combinatorial control over FLO11 transcription.

In a second example, wve measured the expression of lacZ from fragments of the FLO11 promoter in strains mutant for AFL1. The diploids of this mutant strain do not forn filaments or invade under conditions where wild-type yeast do. We discovered that one element, FLO11-11/10, was completely dependent upon AFL1 for expression. We also found that expression from FLO11 promoter fragment 11/10 was induced more that 15-fold as yeast cells change from log phase growth to stationary phase growth. Furthermore, this stationary phase induction of transcription from FLO11-11/10 was completely dependent on AFL1.

As shown above, FLO11 expression is dependent upon numerous genes involved in pseudohyphal growth and haploid invasion. Thus, by combining the analysis of the FLO11 promoter with the variety of mutant strains, we will be able to map the trans-acting elements which regulate FLO11, as well as the important promoter elements which serve as targets. As many of the *S. cerevisiae* genes have homologs in other fungi, this analysis will allow for identification of putative targets for compounds which prevent fungal invasion or which promote production of secondary metabolites.

In another example of using FLO11 promoter fragments and deletions in combination with mutant strains, the sites within the promoter where the cAMP signal activates FLO11 transcription were determined. We transformed the 400 bp reporter series into a ras1 ras2pde2 mutant strain (SR957), a strain where internal cAMP levels can be manipulated by adding cAMP to the media. Addition of 2 mM cAMP to SR957 led to a 3-fold induction of FLO11-6/5 and a 2-fold induction of FLO11-7/6, FLO11-8/7 and FLO11-10/9, as compared to SR957 grown without cAMP. These results suggest that trans-acting elements upregulate FLO11 expression through a cAMP-mediated signal via more than one cis-acting element. The segment most strongly induced by cAMP is defined by the overlapping elements FLO11-6/5 and FLO11-7/6 (bp −1200 to −1000), the same element targeted by Flo8. As shown earlier, this element is also required for induction of invasive and filamentous growth.

As described above, FLO11 transcripts were not detectable in a strain (L5816, flo8-2) that contains a deletion of the FLO8 gene. Furthermore, FLO11 induction by cAMP is blocked in a ras1 ras2pde2 strain (SR108I) carrying a deletion of FLO8. The ste12 ras1 ras2pde2 strain (SR1088), like the flo8 ras1 ras2pde2 strain (SR1081), has dramatically reduced expression of FLO11. However, FLO11 transcription can be induced by cAMP in the ste12 ras1 ras2pde2 strain. The induction of FLO11 by cAMP in the ste12 mutant and not in the flo8 mutant is consistent with the phenotypes of the corresponding strains: a flo8 ras1 ras2 pde2 strain is unable to form filaments on SLAD plates or to invade the agar on YPD plates, even in the presence of cAMP, whereas ste12 ras1 ras2pde2 is both invasive and able to form filaments on YPD or SLAD plates containing 2 mM cAMP. Thus, high cAMP levels can bypass the requirement for the MAPK cascade transcription factor Ste12, but not the requirement for Flo8 in the activation of FLO11 transcription. These experiments support a model in which several signal transduction cascades converge on the promoter of FLO11.

The suppression patterns of ste12 and flo8 mutants by overexpression of FLO8 and STE12, respectively, supports a model of their joint control over FLO11. Overexpression of FLO8 in a ste12 strain (SR1021) and overexpression of STE12 in a flo8 strain (SR 1134) suppressed the pseudohyphal and invasion defects of the mutants. The morphologies of the pseudohyphae in the "suppressed" strains were not identical to that of wild-type. In flo8 strains overexpressing STE12, the cells of each pseudohyphal strand appear more elongate than the cells of wild-type pseudohyphae. In ste12 strains overexpressing FLO8, the cells are not longer than wild type. However, they have a denser network of filaments. This colony morphology is similar to that of strains that are induced to form filaments by cAMP (SR959).

The patterns of suppression by overexpression were reflected in the FLO11 expression pattern. Overexpression of FLO8 enhanced the expression of FLO11 10-fold in a ste12 mutant (SR1021). The reciprocal experiment in which STE12 was overexpressed is more difficult because high levels of Ste12 are toxic. To control the levels of STE12, we used a GAL::STE12 construct which could be regulated by galactose. In a flo8 strain (SR 1134) containing this GAL-::STE12 construct on a plasmid, the FLO11 transcript levels were increased 3-fold on SC-glucose medium as compared to the strain transformed with the control plasmid (SR1097). This increase probably represented incomplete repression of the GAL promoter. If STE12 was induced by incubation for four hours in SC-galactose medium, FLO11 expression was increased 10-fold.

To determine whether a high level of internal cAMP stimulated FLO11 transcription, we deleted IRA1 in an otherwise wild-type strain. Ira1 is a Ras-GAP that inactivates Ras-GTP by converting it to Ras-GDP. Loss of Ira1 function leads to a higher proportion of activated Ras and thus to elevated cAMP levels in the cell (Tanaka et al., 1989). In the ira1 mutant strain (SR599), FLO11 transcripts were strongly induced. This FLO11 induction was reflected in the hyperinvasive phenotype of strains devoid of IRA1 function. A ste12 Ira1 mutant (SR 1133) was still hyperinvasive, illustrating that at least some of the cAMP signal was independent of the MAPK pathway. However, flo11 ira1 (SR1079) or flo8 ira1 (SR 1132) strains failed to invade. These results are consistent with the interpretation that Flo8 is required for the induction of FLO11 by high internal and external cAMP levels. A strain (SR 1132) lacking both FLO8 and IRA1 had dramatically reduced levels of FLO11 transcripts, whereas deletion of STE12 in an ira1 background (SR 1133) still showed FLO11 transcript levels comparable to wild type. These results are consistent with the hyper-invasive phenotype of the ira1 ste12 strain and the non-invasive phenotype of the ira1 flo8 strain.

Analysis of the regulation of the FLO11 promoter in *S. cerevisiae* has provided, and is likely to continue to provide, valuable information regarding the regulation of invasion and secondary metabolite production in diverse fungal species. Promoters of other genes involved in invasion or secondary metabolite production from *S. cerevisiae* or other fungal species are similarly likely to provide further valuable information about the regulation of invasion and secondary metabolite production. An example of such a promoter is the ECE1 gene promoter from *Candida albicans*. Expression of the *Candida albicans* ECE1 gene is highly induced during the conversion from noninvasive yeast growth to invasive hyphal growth. In order to clone Candida regulators of invasive growth, a fusion between the ECE1 promoter and the *E. coli* lacZ gene was constructed. Specifically, PCR primers were designed to generate a DNA fragment consisting of 706 bases upstream of the ECE1 start codon and the first 10 codons of the ECE1 gene. That fragment was cloned to create an in-frame translational fusion with lacZ carried on a yeast 2 $\mu$/LEU2 shuttle vector. The fusion plasmid was used to transform a diploid *Saccharomyces cerevisiae* strain that was homozygous leu2/leu2 and ura3/ura3. The strain was subsequently transformed with a library of *Candida albicans* genomic DNA fragments cloned in a yeast 2 $\mu$/URA3 vector. Resulting double transformants were recovered on selective medium lacking supplemental amino acids, pooled, and then replated at low density (200–300 colonies/plate) on minimal medium that contained 50 mM phosphate buffer (pH 7) and 0.003% w/v XGAL. The plates were incubated for one week and dark blue colonies were picked with the idea that cloned Candida regulators of invasion would activate transcription of lacZ via the ECE1 promoter. The 2 $\mu$/URA3 plasmids were isolated from the blue transformants, retested and then the cloned DNA was sequenced. One of the genes identified was Candida AFL1. Expression of the Candida AFL1 gene in *S. cerevisiae* imparted enhanced invasive behavior on diploids under rich medium conditions where it normally does not invade the substrate. Standard database searching for homologs of the Candida AFL1 gene revealed an *S. cerevisiae* homolog. An *S. cerevisiae* strain containing a complete deletion of AFL1 did not form filaments or invade under conditions where wild-type yeast did.

AFL1 regulates the expression of both *S. cerevisiae* FLO11 (described above) and Candida ECE1. It is likely that homologs of other *S. cerevisiae* genes which regulate FLO11 will regulate the promoters of genes which themselves regulate hyphal growth or invasion in other fungi. The downstream genes can be determined through a number of teclniques known to those skilled in the art. One example is to use microarray analysis, as described in DeRisi et al. Science 1997, 278:680.

The use of Saccharomyces to clone a Candida gene by screening for its function as an inducer of Candida ECE11 gene transcription exemplifies another approach to isolate important fungal genes involved in invasion or production of secondary metabolites. The success of this experiment in cloning an important Candida regulator of invasion proves the concept that it is possible to clone regulators of transcription from potentially diverse species by using Saccharomyces as a heterologous host in which to screen. This technique gives the advantages of the sophisticated molecular genetic tools available for Saccharomyces, but not for other organisms. This has implications not only for fungi like Candida, but potentially for very disparate species such as mammalian species. This method may also be useful in performing more detailed analysis of the function of regulators of transcription from non-Saccharomyces species. The use of Saccharomyces as a heterologous host can be combined with selection-based screens to rapidly screen cDNA or genomic libraries to isolate regulators of transcription of Candida, or any other organism.

Screening Assays for Genes and Compounds

As discussed above, we have identified a number of fungal invasion-promoting and invasion-inhibiting factors that are involved in pathogenicity and that may therefore be used to screen for compounds that reduce the virulence of pathogenic fungi, as well as other microbial pathogens or, alternatively, increase the production of secondary metabolites. Any number of methods are available for carrying out such screening assays. According to one approach, candidate compounds are added at varying concentrations to the culture medium of pathogenic fungal cells expressing one of the nucleic acid sequences described herein. Gene expression is then measured, for example, by standard northern blot analysis (Ausubel et al., sitpra), using any appropriate fragment prepared from the nucleic acid molecule as a hybridization probe. The level of gene expression in the presence of the candidate compound is compared to the level measured in a control culture medium lacking the candidate molecule. A compound which promotes a decrease in the expression of the invasion-promoting factor is considered useful in the invention; such a molecule may be used, for example, as a therapeutic to combat the pathogenicity of an infectious organism. A compound which promotes an increase in the expression of the invasion-promoting factor is considered useful in the invention; such a molecule may be used, for example, as a potentiator, increasing production of commercially important secondary metabolites.

If desired, the effect of candidate compounds or genes may, in the alternative, be measured by assaying the protein polypeptide level. There are numerous preferred protein assays, including standard immunological techniques, such as western blotting or immunoprecipitation with an antibody specific for an invasin polypeptide. For example, immunoassays may be used to detect or monitor the expression of at least one of the polypeptides of the invention in a pathogenic organism. Polyclonal or monoclonal antibodies (produced as described in Harlow and Lane, Antibodies, a laboratory manual 1988, Cold Spring Harbor Press) which are capable of binding to such a polypeptide may be used in any standard immunoassay format (e.g., ELISA, western blot, or RIA assay) to measure the level of the pathogenicity polypeptide. In another example, polypeptide levels may be determined using enzymatic activity in standard assays. Standard kits are available (for example the Galacto-Plus and GUS light systems, available from Tropix, Inc., Bedford Mass.) which allow for measurement of enzymatic activity of, for example, Chloramphenicol acetyl transferase (CAT) and β-galactosidase (encoded by the lacZ gene). Protein levels can also be determined using techniques such as fluorescence-activated cell sorting (FACS), spectrophotometry, or luminescence. A compound which promotes a decrease in the expression of the invasion-promoting polypeptide is considered useful. Again, such a molecule may be used, for example, as a therapeutic to combat the pathogenicity of an infectious organism. A compound or which promotes an increase in the expression of the invasion-promoting polypeptide is also considered useful. Again, such a molecule may be used, for example, as a potentiator, increasing production of commercially important secondary metabolites.

Alternatively, or in addition, candidate compounds may be screened for those which specifically bind to and inhibit an invasin polypeptide of the invention. The efficacy of such a candidate compound is dependent upon its ability to interact with the invasin polypeptide. Such an interaction can be readily assayed using any number of standard binding techniques and functional assays (e.g., those described in Ausubel et al., supra). For example, a candidate compound may be tested in vitro for interaction and binding with a polypeptide of the invention and its ability to modulate pathogenicity may be assayed by any standard assays (e.g., those described herein).

In one particular example, a candidate compound that binds to a invasin polypeptide may be identified using a chromatography-based technique. For example, a recombinant polypeptide of the invention may be purified by standard techniques from cells engineered to express the polypeptide (e.g., those described above) and may be immobilized on a column. A solution of candidate compounds is then passed through the column, and a compound specific for the invasin polypeptide is identified on the basis of its ability to bind to the invasin polypeptide and be immobilized on the column. To isolate the compound, the column is washed to remove non-specifically bound molecules, and the compound of interest is then released from the column and collected. Compounds isolated by this method (or any other appropriate method) may, if desired, be further purified (e.g., by high performance liquid chromatography). In addition, these candidate compounds may be tested for their ability to render a pathogen less virulent (e.g., as described herein). Compounds isolated by this approach may also be used, for example, as therapeutics to treat or prevent the onset of a pathogenic infection, disease, or both. Compounds which are identified as binding to pathogenicity polypeptides with an affinity constant less than or equal to 10 mM are considered particularly useful in the invention.

In yet another approach, candidate genes and compounds are screened for the ability to inhibit the virulence of a fungal cell by monitoring expression from a promoter element Inown to be positively or negatively regulated during filamentous invasion, hyphal growth, pseudohyphal growth or haploid digging. These same selection-based systems may be configured to screen for genes or compounds which lead to increased expression from the FLO11 promoter ($P_{FLO11}$). In one example, $P_{FLO11}$ is fused to a gene that confers a growth advantage when their expression is increased. For example, a $P_{FLO11}$-HIS3 fusion that allows growth on SC-HIS when present in a his3 mutant has been generated. This fusion has the added advantage that expression levels can be titrated by the compound 3-aminotriazole (3-AT). 3-AT is a competitive inhibitor of His3 that, when present in sufficient amounts, will inhibit the His3 expressed from $P_{FLO11}$ and prevent this strain from growing on SC-HIS. Therefore, growth of a strain containing $P_{FLO11}$-HIS3 only occurs on SC-HIS+3-AT plated when $P_{FLO11}$-HIS3 expression is increased to overcome the competitive inhibition of His3 by 3-AT. Increased expression of the transcription factor Tec1 confers increased resistance to 3-AT in such a strain. By varying the amount of 3-AT used, the extent of increased $P_{FLO11}$-HIS3 necessary for growth can be modulated. Numerous markers could be used for such positive selection systems, including, but not limited to, URA3, TRP1, ADE2, LEU2. Those skilled in the art will recognize that other positive selection systems will also work in this system.

In another example, gene fusions that link $P_{FLO11}$ to a gene product that confers a growth disadvantage (in its most extreme case-death) can be used to select for genes and compounds which down-regulate FLO11 expression. In this case, any condition that decreases and/or eliminates FLO11 expression will alleviate the growth disadvantage and allow strains to grow. For example, a fusion of $P_{FLO11}$ to the URA3 open reading frame that allows for growth on SC-URA in a $P_{FLO11}$-dependent manner has been created. Since expression of URA3 is toxic in the presence of 5-fluoro-orotic acid (5-FOA), selection against FLO11 expression can be accomplished by screening for growth on SC+5-FOA of a strain carrying a $P_{FLO11}$URA3 fusion. Those skilled in the art will recognize that other negative selection systems will also work in this system.

While the systems described above allow for the selection for or against FLO11 expression, similar technologies can be used to screen for changes in FLO11 expression. Other examples of useful $P_{FLO11}$ reporter gene fusions that can be quantified include, but are not limited to, enzymatic or fluorescent reporters such as lacZ and green fluorescent protein (GFP).

The selection and screening systems described here have a number of potential applications beyond those stated above. For example, they can be used to identify, by selection methods, functional homologs for many of the genes that regulate FLO11. For example, mutation of a gene that eliminates FLO11 expression in a strain deleted for his3 and carrying a $P_{FLO11}$HIS3 fusion will cause this strain to be a histidine auxotroph (unable to grow in media lacking histidine). However, cDNA or genomic DNA clones from other organisms that restore FLO11 expression in such strains (either by complementation or suppression of the mutant allele) can be directly selected for by selecting for growth on media lacking histidine. Similarly, novel regulators of FLO11 expression from *S. cerevisiae* and heterologous organisms can be identified using the same selection schemes.

In another application of using promoters known to be regulated during hyphal or pseudohyphal growth, deletion constructs can be generated in order to map the cis elements of the promoter required for each signal transduction pathway. As an example, the FLO11 promoter screening and selection assays, in which nested deletions of 200 bp steps from the 3 kb region upstream of the FLO11 ORF have been generated, are being analyzed for effects on lacZ expression in various wild-type and mutant background strains. In another example, overlapping 400 bp fragments of the FLO11 promoter have been cloned into the CYC1 transcriptional unit (FIG. 11). Together, these examples will demonstrate which DNA regions are required for expression (and to what extent each of these regions is required). Furthermore, reporter gene fusions with subcloned pieces of promoters regulated during hyphal growth or pseudohyphal growth, such as the FLO11 promoter, can be assessed for expression in various mutants that block (or activate) distinct pathways. A person skilled in the art will recognize that regulatory elements from other invasins, including those described herein, can be isolated as described using the methods described herein, in conjunction with standard techniques described in Ausubel et al. (supra). These methods include fusion of a DNA segment from a putative regulatory or promoter region to a reporter gene, as well as deletion analysis. Moreover, the pathway specificity of any invasin promoter can be determined through the use of wild-type and mutant host strains. If a given DNA segment confers reporter expression in a wild-type strain, but shows either no or increased expression in specific mutants, then this sequence can be inferred to mediate invasin expression by whatever pathway that mutant defines. Using this approach, a set of gene fusions that report distinct pathways that regulate FLO11 can be generated. A variety of basal or inducible promoter elements are applicable for this technique, including, but not limited to, CYC1, PGK1, ADH1, GAL1-10, tet-R, MET25, and CUP1. Using the above system, a mode of action can be assigned for any given treatment on FLO11 expression. Assessment of the effect of a chemical or genetic treatment on pathway-specific reporters will make it possible to determine which pathway is altered by this treatment. For example, consider two different reporter fusions, one (Reporter 1) that reports STE pathway-mediated expression of FLO11, and the other (Reporter 2) that reports INV pathway-mediated expression of FLO11. If compound X, which was identified by its ability to eliminate expression of the full-length $P_{FLO11}$, is shown to affect Reporter 1 but not Reporter 2, then it is inferred that compound X blocks FLO11 expression by affecting STE pathway activity. Similarly, where the compound affects a given pathway will also be refined using pathway-specific $P_{FLO11}$ reporter constructs and activated alleles of certain signaling components. For example, the mutant STE11-4 and overexpression of STE12 are both predicted to increase FLO11 expression. If compound X blocks the increased expression of FLO11 mediated by STE11-4, but not STE12 overexpression, then compound X can be inferred to antagonize the STE pathway before STE12, but at or below STE11. Assessing reporter expression in various deletion mutants will enable similar approaches to assess the effect of compounds that activate expression of FLO11.

The reporters used in these experiments can be utilized in the same way as those described for the full-length FLO11 promoter to allow for positive and negative selections and a variety of screening methods. This will make it possible to identify pathway-specific modulators (heterologous genes, compounds, peptides etc.) of FLO11 expression. Such a system is also useful in identifying modulators of important homologs of these regulatory genes from other organisms. For example, the small G-protein Ras is activated in many kinds of human tumors, and it is of interest to identify inhibitors of RAS as candidate antitumor agents. Having a FLO11 promoter fragment fusion that reports the activity of human RAS in yeast (e.g., in a yeast strain deleted for the two yeast RAS genes and expressing human RAS) would allow one to select and/or screen for modulators of human Ras in yeast.

Another example of a screen is based on the observation that yeast from haploid *S. cerevisiae* invade agar when grown on rich (YPD) medium without forming pseudohyphae. This nonfilamentous invasion behavior has been termed "digging," and the assay used to detect this behavior has been termed the "dig assay." Roberts and Fink, supra. Mutations that block digging of haploid *S. cerevisiae* on rich media also inhibit pseudohyphal growth and agar invasion of diploid *S. cerevisiciae* under low nitrogen conditions. Mutant strains defective for digging are referred to as "dig minus," or "dig–." The correlation of pseudohyphal invasion and behavior in the dig assay is an essential aspect of this screen. The dig assay is comparatively easy to perform relative to pseudohyphal invasion assays, and, as it occurs in haploid cells, is more amenable to genetic approaches that rely upon recessive mutations.

We have discovered that pathogenic fungi can display similar digging behavior, characterized by increased invasion into or adherence to a defined substrate. For example, *C. albicans* displays a nonfilamentous invasion of substrate in a variety of suitable conditions (e.g., YPD, and SPIDER). This behavior is similar to the reported digging behavior of *S. cerevisiae*. As is true for *S. cerevisiae*, non-hyphal agar invasion by any given *C. albicans* mutant strain correlates with the ability of that strain to form filaments under filament-inducing conditions (e.g., agar+serum). Thus, screening for compounds that block the digging phenotype in fungi will allow for identification of compounds that block filament formation and, as a result, pathogenesis. These compounds are considered useful as fungicides or fungistats. Similarly, screening for compounds that increase substrate invasion will allow for identification of compounds which may also increase production or yield of secondary metabolites.

An example of the dig assay is given below. To test whether a chemical compound would affect the nonfilamentous agar invasion behavior of nonmutant *S. cerevisiae* or *C. albicans* at concentrations much lower than the lowest growth inhibitory concentration, these fungi were spotted onto agar plates containing rich medium (YPD) and a gradient of the antifungal fluconazole. The plates were then incubated for two days at optimum growth temperatures and washed with water. Both fungi exhibited inhibition of agar invasion at significantly lower concentrations of fluconazole than those necessary to inhibit growth (FIG. 12). This assay can be performed on other dimorphic fungi, such as *U. maydis*, as well as on other fungi. In all cases, the invasion assay can be used to isolate compounds which inhibit invasion, or those which promote invasion. Each type of compound would have valued uses as described herein.

Optionally, invasion-inhibiting compounds identified in any of the above-described assays may be confirmed as useful in conferring protection against the development of a pathogenic infection in any standard animal model. One example is described herein. Candidate compounds, if successful, may be used for anti-pathogen therapeutics. Invasion-promoting compounds may be confirmed by assessing production of secondary metabolites. Candidate compounds, if successful, may be used as potentiators to increase production or yield of these or other secondary metabolites.

Test Compounds and Extracts

In general, compounds are identified from large libraries of both natural product and synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their anti-pathogenic activity should be employed whenever possible.

When a crude extract is found to have an invasion-promoting or invasion-inhibiting activity, or a binding activity, further fractionation of the positive lead extract is necessary to isolate chemical constituents responsible for the observed effect. Thus, the goal of the extraction, fractionation, and purification process is the careful characterization and identification of a chemical entity within the crude extract having the desired activity. Methods of fractionation and purification of such heterogenous extracts are known in the art. If desired, compounds shown to be useful agents for the treatment of pathogenicity or increased production of secondary metabolites are chemically modified according to methods known in the art.

Pharmaceutical Therapeutics and Plant Protectants The invention provides a simple means for identifying compounds (including peptides, small molecule inhibitors, and mimetics) capable of inhibiting the pathogenicity or virulence of a pathogen. Accordingly, chemical entities discovered to have medicinal or agricultural value using the methods described herein are useful as either drugs, plant protectants, or as information for structural modification of existing anti-pathogenic compounds, e.g., by rational drug design. Such methods are useful for screening compounds having an effect on a variety of pathogens including, but not limited to, bacteria, viruses, fungi, annelids, nematodes, Platyhelminthes, and protozoans. Examples of pathogenic fungi include, without limitation, *Candida albicans*, Aspergillus sp, Mucor sp, Rhizopus sp., Fusarium sp, *Peni-*

*cillium marneffei,* Microsporum sp. *Cryptococcis neoformans, Pneumocystis carinii,* and Trichophyton sp.

For therapeutic uses, the compositions or agents identified using the methods disclosed herein may be administered systemically, for example, formulated in a pharmaceutically-acceptable buffer such as physiological saline. Treatment may be accomplished directly, e.g., by treating the animal with antagonists which disrupt, suppress, attenuate, or neutralize the biological events associated with a pathogenicity polypeptide. Preferable routes of administration include, for example, inhalation or subcutaneous, intravenous, interperitoneally, intramuscular, or intradermal injections which provide continuous, sustained levels of the drug in the patient. Treatment of human patients or other animals will be carried out using a therapeutically effective amount of an anti-pathogenic agent in a physiologically-acceptable carrier. Suitable carriers and their formulation are described, for example, in Remington's *Pharmaceutical Sciences* by E. W. Martin. The amount of the anti-pathogenic agent to be administered varies depending upon the manner of administration, the age and body weight of the patient, and with the type of disease and extensiveness of the disease. Generally, amounts will be in the range of those used for other agents used in the treatment of other microbial diseases, although in certain instances lower amounts will be needed because of the increased specificity of the compound. A compound is administered at a dosage that inhibits microbial proliferation. For example, for systemic administration a compound is administered typically in the range of 0.1 ng–10 g/kg body weight.

For agricultural uses, the compositions or agents identified using the methods disclosed herein may be used as chemicals applied as sprays or dusts on the foliage of plants, or in irrigation systems. Typically, such agents are to be administered on the surface of the plant in advance of the pathogen in order to prevent infection. Seeds, bulbs, roots, tubers, and corms are also treated to prevent pathogenic attack after planting by controlling pathogens carried on them or existing in the soil at the planting site. Soil to be planted with vegetables, ornamentals, shrubs, or trees can also be treated with chemical fumigants for control of a variety of microbial pathogens. Treatment is preferably done several days or weeks before planting. The chemicals can be applied by either a mechanized route, e.g., a tractor or with hand applications. In addition, chemicals identified using the methods of the assay can be used as disinfectants.

In addition, the antipathogenic agent may be added to materials used to make catheters, including but not limited to intravenous, urinary, intraperitoneal, ventricular, spinal and surgical drainage catheters, in order to prevent colonization and systemic seeding by potential pathogens. Similarly, the antipathogenic agent may be added to the materials that constitute various surgical prostheses and to dentures to prevent colonization by pathogens and thereby prevent more serious invasive infection or systemic seeding by pathogens.

Enhancement of Secondary Metabolite Production

The invention provides a simple means for identifying compounds (including peptides, small molecules and mimetics) that are capable of activating secondary metabolite production in fungi. Accordingly, a chemical entity discovered to have such characteristics using the methods described herein is useful as a means to increase the yields of currently marketed pharmaceuticals whose production, in whole or in part, is dependent upon a fungal fermentation. Examples of marketed secondary metabolites whose yields during fermentation could be increased by such compounds include, without limitation, cyclosporin, penicillin, cephalosporin, ergot alkaloids, lovastatin, mevastatin, and the biosynthetic intermediates thereof. In addition, such chemical entities can also be used to increase the likelihood of identifying new secondary metabolites with medicinal or agricultural value by increasing the concentration of such metabolites (and hence, the likelihood of detection by chemical or bioassay) in a fermentation broth. In both instances, increased yield of metabolite can be accomplished by contacting fungi with the entity and/or transforming a fungus with a gene expression construct or constructs that would result in the production of said entity within the fungus.

The invention also provides a simple means for identifying candidate genes that both positively and negatively regulate secondary metabolite production in fungi. In addition, methods to identify activated and dominant negative versions of these genes are described. Accordingly, such genes and their derivatives are likely candidates to enable the genetic engineering of fungi to increase production of secondary metabolites both through the introduction of altered forms of these genes into production fungi by standard transformation methods and also by elimination of relevant gene function through the construction of knockouts. Examples of marketed secondary metabolites whose yields during fermentation could be increased by genetic engineering methods such as these include, without limitation, cyclosporin, penicillin, cephalosporin, ergot alkaloids, lovastatin, mevastatin, and the biosynthetic intermediates thereof.

Production and Detection Methods for Fungal Secondary Metabolites

Methods for fermentation and production of beta-lactam antibiotics, statins, ergot alkaloids, cyclosporin, and other fungal metabolites are described in Masurekar (Biotechnology 1992, 21: 241–301), and references therein. The detection of secondary metabolites is specific for each metabolite and well-known to those practiced in the art. General methods to assess production and integrity of compounds in fermentation broths include, but are not limited to, bioassays for antimicrobial activity, high-performance liquid chromatography (HPLC) analysis, nuclear magnetic resonance, thin-layer chromatography, and absorbance spectrometry. Purification of metabolites from a fermentation broth can include removal of fungal cells or hyphae by centrifugation or filtration, adjustment of pH and/or salt concentrations after fermentation (to enhance solubility and/or subsequent extraction efficiency), and extraction of broths with appropriate organic solvents.

Other Embodiments

In general, the invention includes any nucleic acid sequence which may be isolated as described herein or which is readily isolated by homology screening or PCR amplification using the nucleic acid sequences of the invention. Also included in the invention are polypeptides which are modified in ways which do not abolish their pathogenic activity (assayed, for example as described herein). Such changes may include certain mutations, deletions, insertions, or post-translational modifications, or may involve the inclusion of any of the polypeptides of the invention as one component of a larger fusion protein.

Thus, in other embodiments, the invention includes any protein which is substantially identical to a polypeptide of the invention. Such homologs include other substantially pure naturally-occurring polypeptides as well as allelic variants; natural mutants; induced mutants; proteins encoded by DNA that hybridizes to any one of the nucleic acid sequences of the invention under high stringency conditions or, less preferably, under low stringency conditions (e.g., washing at 2×SSC at 40° C. with a probe length of at least 40 nucleotides); and proteins specifically bound by antisera of the invention.

The invention further includes analogs of any naturally-occurring polypeptide of the invention. Analogs can differ from the naturally-occurring polypeptide of the invention by amino acid sequence differences, by post-translational modifications, or by both. Analogs of the invention will generally exhibit at least 85%, more preferably 90%, and most preferably 95% or even 99% identity with all or part of a naturally-occurring amino acid sequence of the invention. The length of sequence comparison is at least 15 amino acid residues, preferably at least 25 amino acid residues, and more preferably more than 35 amino acid residues. Again, in an exemplary approach to determining the degree of identity, a BLAST program may be used, with a probability score between $e^{-3}$ and $e^{-100}$ indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the invention by alterations in primary sequence. These include genetic variants, both natural and induced (for example, resulting from random mutagenesis by irradiation or exposure to ethanemethylsulfate or by site-specific mutagenesis as described in Sanbrook, Fritsch and Maniatis, *Molecular Cloning: A Laboratory Manual* (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., β or γ amino acids.

In addition to full-length polypeptides, the invention also includes fragments of any one of the polypeptides of the invention. As used herein, the term "fragment," means at least five, preferably at least 20 contiguous amino acids, preferably at least 30 contiguous amino acids, more preferably at least 50 contiguous amino acids, and most preferably at least 60 to 80 or more contiguous amino acids. Fragments of the invention can be generated by methods known to those skilled in the art or may result from normal protein processing (e.g., removal of amino acids from the nascent polypeptide that are not required for biological activity or removal of amino acids by alternative mRNA splicing or alternative protein processing events).

The invention further provides compositions (e.g., nucleotide sequence probes) and methods for the diagnosis of a pathogenic condition.

All publications and patent applications mentioned in this specification are herein incorporated by reference to the same extent as if each independent publication or patent application was specifically and individually indicated to be incorporated by reference.

Other embodiments are within the scope of the claims.

What is claimed is:

1. A method of isolating a fungal invasin gene, said method comprising
   (a) providing a fungus expressing a gene operably linked to a fungal invasin gene promoter;
   (b) mutagenizing said fungus;
   (c) measuring expression of the gene, wherein an increase or decrease in the expression of said gene identifies a mutation in said invasin gene; and
   (d) using said mutation as a marker for isolating said invasin gene.

2. The method of claim 1, wherein said fungus is a wild-type strain.

3. The method of claim 2, wherein said wild-type strain is *Saccharomyces cerevisiae*.

4. The method of claim 1, wherein said fungus is a mutant strain.

5. The method of claim 1, wherein said gene comprises a fungal invasin gene.

6. The method of claim 5, wherein said fungal invasin gene is FLO11 or MUC1.

7. The method of claim 5, wherein said fungal invasin gene is AFL1, DHH1, INV1, INV5, INV6, INV7, INV8, INV9, INV10, INV11, INV12, INV13, INV14, INV15, BEM2, CDC25, HOG1, IRA1, MCM1, MGA1, PET9, PHD2, PHO23, RIM1, PTC1, RIM15, SFL1, SRB11, SSD1, STE21, STP22, SWI4, TPK2, TPK3, or YPR1.

8. The method of claim 1, wherein said gene comprises a reporter gene.

9. The method of claim 8, wherein said reporter gene is lacZ, URA3, or HIS3.

10. The method of claim 1, wherein said fungal invasin gene promoter is the FLO11, MUC1, STA1, STA2, or STA3 gene promoter.

11. The method of claim 1, wherein said fungal invasin gene promoter is the AFL1, DHH1, INV1, INV5, INV6, INV7, INV8, INV9, INV10, INV11, INV12, INV13, INV14, INV15, BEM2, CDC25, RIM1, HOG1, IRA1, MCM1, MGA1, PET9, PHD2, PHO23, PTC1, RIM15, SFL1, SRB11, SSD1, STE21, STP22, SWI4, TPK2, TPK3, or YPR1 gene promoter.

12. The method of claim 1, wherein said fungal invasin gene promoter is a fragment or deletion of the FLO11, MUC1, STA1, STA2, or STA3 gene promoter.

13. The method of claim 12, wherein said fragment is fused to a basal promoter.

14. The method of claim 13, wherein said basal promoter is PGK1, ADH1, GAL1-10, tet-R, MET25, CYC1 or CUP1.

15. The method of claim 1, wherein said gene expression is measured by assaying the protein level of the expressed gene.

16. The method of claim 1, wherein said gene expression is measured by assaying the RNA level of the expressed gene.

\* \* \* \* \*

UNITED STATES PATENT AND TRADEMARK OFFICE
CERTIFICATE OF CORRECTION

PATENT NO. : 6,599,705 B2
DATED : July 29, 2003
INVENTOR(S) : Steffen Ruff et al.

It is certified that error appears in the above-identified patent and that said Letters Patent is hereby corrected as shown below:

Column 23,
Line 38, delete the 2 spaces after "2"
Line 40, delete "CAMP", insert -- cAMP --

Column 24,
Lines 44 and 45, delete "(SEQID NO: 7) and", insert -- (SECID NO: 7 and --

Column 26,
Line 48, delete the space between "SC-1" and "mM"
Line 67, delete the space between "20" and "h"

Column 28,
Line 12, delete "flo11-6flo121-6", insert -- flo11-6/flo11-6 --

Column 30,
Line 52, delete "wve", insert -- we --
Line 55, delete "forn", insert -- form --

Column 31,
Lines 10, 27, 28, 29, 31 and 37, insert a space between "ras2" and "pde2"
Line 27, delete "SR108I", insert -- SR1081 --
Line 47, insert a space between "their" and "joint"

Column 32,
Line 16, delete "Ira1", insert -- ira1 --
Line 16, delete the spaces between "SR" and "1133"
Lines 19 and 22, delete the spaces between "SR" and 1132"

Column 33,
Line 33, delete "sitpra", insert -- supra --

UNITED STATES PATENT AND TRADEMARK OFFICE
CERTIFICATE OF CORRECTION

PATENT NO. : 6,599,705 B2
DATED : July 29, 2003
INVENTOR(S) : Steffen Ruff et al.

It is certified that error appears in the above-identified patent and that said Letters Patent is hereby corrected as shown below:

Column 34,
Line 66, delete "a" before "invasion", insert -- an --

Column 42,
Line 1, delete "Sanbrook", insert -- Sambrook --

Signed and Sealed this

Twenty-seventh Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,599,705 B2
DATED : July 29, 2003
INVENTOR(S) : Steffen Ruff et al.

It is certified that error appears in the above-identified patent and that said Letters Patent is hereby corrected as shown below:

Title page,
Item [56], References Cited, OTHER PUBLICATIONS, insert -- Lambrechts et al., "Muc 1, a mucin-like protein that is regulated by Mss10, is critical for…" Proc. Natl. Acad. Sci. USA 93:8419-8424, 1996. --

Column 2,
Line 54, delete "ST2", insert -- STA2 --

Column 5,
Line 24, insert a space after "Rim1,"
Line 26, insert -- Tpk2, -- after "Stp22,"

Column 7,
Line 40, delete "J-glucosidase", insert -- J-glucoronidase --

Column 17,
Line 14, delete the comma after "mg"

Column 18,
Line 38, delete "Interaction," insert -- Interacting --
Line 61, delete "Isolation", insert -- Isolating --

Column 23,
Line 2, insert a space between "ras2" and "pde2"
Line 10, delete the comma after "ras2"
Line 22, delete the space after "2"
Line 31, insert a space between "ras2" and "pde2"

Column 23,
Line 38, delete the 2 spaces after "2"
Line 40, delete "CAMP", insert -- cAMP --

UNITED STATES PATENT AND TRADEMARK OFFICE
CERTIFICATE OF CORRECTION

PATENT NO.    : 6,599,705 B2
DATED         : July 29, 2003
INVENTOR(S)   : Steffen Ruff et al.

It is certified that error appears in the above-identified patent and that said Letters Patent is hereby corrected as shown below:

Column 24,
Lines 44 and 45, delete "(SEQID NO: 7) and", insert -- (SECID NO: 7 and --

Column 26,
Line 48, delete the space between "SC-1" and "mM"
Line 67, delete the space between "20" and "h"

Column 28,
Line 12, delete "flo11-6flo121-6", insert -- flo11-6/flo11-6 --

Column 30,
Line 52, delete "wve", insert -- we --
Line 55, delete "forn", insert -- form --

Column 31,
Lines 10, 27, 28, 29, 31 and 37, insert a space between "ras2" and "pde2"
Line 27, delete "SR108I", insert -- SR1081 --
Line 47, insert a space between "their" and "joint"

Column 32,
Line 16, delete "Ira1", insert -- ira1 --
Line 16, delete the spaces between "SR" and "1133"
Lines 19 and 22, delete the spaces between "SR" and 1132"

Column 33,
Line 33, delete "sitpra", insert -- supra --

Column 34,
Line 66, delete "a" before "invasion", insert -- an --

UNITED STATES PATENT AND TRADEMARK OFFICE
CERTIFICATE OF CORRECTION

PATENT NO.   : 6,599,705 B2
DATED        : July 29, 2003
INVENTOR(S)  : Steffen Ruff et al.

It is certified that error appears in the above-identified patent and that said Letters Patent is hereby corrected as shown below:

Column 42,
Line 1, delete "Sanbrook", insert -- Sambrook --

This certificate supersedes Certificate of Correction issued July 27, 2004.

Signed and Sealed this

Twelfth Day of October, 2004

JON W. DUDAS
*Director of the United States Patent and Trademark Office*

SEQUENCE LISTING

<160> NUMBER OF SEQ ID NOS: 67

<210> SEQ ID NO 1
<211> LENGTH: 39
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (28)..(28)
<223> OTHER INFORMATION: Nucleotide 28 is "n" wherein "n" = a, t, g, or c.

<400> SEQUENCE: 1
gaattaaccc tcactaaagg gaaarmgnga ycayathac                               39

<210> SEQ ID NO 2
<211> LENGTH: 38
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (30)..(30)
<223> OTHER INFORMATION: Nucleotide 30 is "n" wherein "n" = a, t, g, or c.

<400> SEQUENCE: 2
gtaatacgac tcactatagg gtgyttyttn arrtcytg                                38

<210> SEQ ID NO 3
<211> LENGTH: 3463
<212> TYPE: DNA
<213> ORGANISM: Candida RIM1

<400> SEQUENCE: 3

```
ttaaaaagtt tttgattgtt gaacttttaa attttttctt ggcaatccat tcccagacaa      60
agtaataact acgaatagat cattcattgg tttattattt ttgcatggaa atatttgaat     120
ttccattttt ttttttttata gtggttgttt aagcttcgca gttttttttt ttctagggag    180
aaattattat acattatata tatattatca acttttctc gttacaaaag tcacaccttt     240
ttttttctta cttgttcttc tttcaacaac taactaattt tatactatcc acgaactata     300
gatattacat ataagttttt aacctagaca acgagagttt ttagacaatg aattacaaca    360
ttcatcccgt aacatactta aatgctgata gcaataccgg tgcaagtgag agtactgcaa     420
gtcaccatgg ttccaagaaa tcaccttcct cagatattga tgtagataat gctwcgtcac    480
cttcatcttt tacttcgtcc caatcacctc acattaatgc tatgggtaac agtccccatt    540
cctcattcac ttctcaatct gcagccaatt ctcctatcac tgatgccaaa caacatttgg    600
ttaaaccaac caccaccaag ccagcagctt tgctcctag tgctaatcaa tctaacacca     660
cagctccgca atcttatacc caaccagcac aacaattacc aactcagtta cacccaagtc    720
ttaaccaagc ctacaacaac caaccatctt attatttaca ccaaccaact tatggctacc    780
aacaacaaca acaacaacaa caacaccaag agtttaacca accatcacag caataccacg    840
accatcacgg atactactca aacaacaaca ttttgaatca gaatcaacca gctccacaac    900
aaaatccagt caagccattc aaaaagacat acaagaaaat cagagacgaa gatttgaaag    960
gtcctttcaa gtgtttgtgg agcaactgta gcattatttt cgagactcca gaaattttgt   1020
acgatcattt gtgtgacgac catgttggta gaaagtcttc gaacaatttg tcattgactt   1080
gtctttggga aaattgtggc acaactacag ttaagagaga tcacattact tctcacttga   1140
gagtccatgt cccattgaag cctttccatt gtgacttgtg tcccaaatcg ttcaagagac   1200
ctcaagattt gaagaaacat tccaagactc acgctgaaga ccatccaaag aagttaaaaa   1260
aggcacaaag agagttgatg aaacaacaac aaaaagaggc caagcaacaa cagaaattgg   1320
ccaacaagag agcaaactcg atgaatgcaa ctaccgcatc cgatttgcaa ttgaactact   1380
attctggtaa ccctgctgat ggattgaact acgacgacac ctccaaaaaa agaagatacg   1440
aaaacaattc tcaacacaac atgtatgtgg ttaatagtat tttgaacgat ttcaacttcc   1500
aacaaatggc tcaagctcca cagcaaccag gcgttgttgg aaccgcaggt tctgctgagt   1560
tcaccaccaa gaggatgaaa gccggcactg agtataacat tgatgtgttt aacaagttga   1620
atcatttgga cgaccacttg caccaccacc accctcaaca gcaacaccca caacaacaat   1680
atggcggtaa catctatgaa gctgaaaaat tcttcaactc cttatcgaat tccatcgaca   1740
tgcaatatca aaacatgtca acccaatatc aacaacaaca tgctggttct acttttgctc   1800
aacagaaacc aactcaacaa gcaagtggcc aattgtatcc ttctttacca accattggca   1860
atggctcata caccagtgga tcatcacaca agaagggtt ggttaataac cataacggat   1920
acttgccatc ttatcctcaa atcaaccgtt ctttgccata ttcttctggt gtggcacaac   1980
aaccaccaag tgcattagag tttggcggtg tttcaaccta ccagaaatct gcacaatcat   2040
atgaagaaga cagcagcgac agttcagagg aagacgatta cagcacttct tcagaagacg   2100
agcttgacac cttgtttgat aaattaaaca tcgatgacaa taaagttgaa gaagtgacga   2160
ttgatgggtt caatttgaag gatgttgcca agcacagaga aatgatccat gctgttcttg   2220
gctatttgag aaaccaaatc gaacaacaag aaaaggaaaa gagcaaagaa caaaggagg   2280
ttgacgttaa tgaaactaaa ttatatccaa ctataactgc tttctaagca attatatcga   2340
```

-continued

```
ttttactttt ttatttattt ttatttttt gtttagggtg gttttcaatt tttttttttt    2400
atttcctcat gtttgatttt agtgtgtttt attgtatatt acgtataagt ttatttatt     2460
agtacaagtt ttgaaagtag tgttaccgtt ctctatttac atggttctat taatcattcc    2520
acctcccaat acttgattcc ctttgtacaa cacaccagct tgacctggcg ccaaagcacg    2580
aactggggtt tctaattcga cggttaacct atcttgcagc tcaataattc ttgtaacagg    2640
gattgacttc agcaatgaat gatactgaaa ttgcaatgat tggagacaaa acaccttttc    2700
cttagggtgt aaccattcta actgcgtcaa ttccacagtt tgtttgaaca acttggggtt    2760
atcgtgacct ttaactatga tgatttgatt tttctcataa ttcttatcgc tgacaaacca    2820
aatgccttgg tattgtggat ctgcttgcgg catgcacact gaagatttct ggcctatcgt    2880
agcatgccat agcccttgt gttgaccca aaccttacca tcttcagtga ttatgtcacc      2940
tgggttttct gggatataat catttaaaaa ctctcggaag tttgactgct gcggattaac    3000
aaagcatagc ccttgggagt cgggttttgt tgctgtgtgt aatttaaact ggtcatgtgc    3060
caattcccga atctgtggtt tgatatagtg ccaatgggt aataagattt tcgataacga     3120
agattgtggg atcgacgaaa gatagtaact ttggtctttc cgttgactca aacctcgcaa    3180
taaatggtac tctccagttt cgttgtgttt catgattcgg gcgtaatgac cagtgactaa    3240
ccaccaatct ttgcctgtgc catcgtattt cttatgcaag taatcaatca acttcccaaa    3300
tttgacaaat ttgttgcacc caatgtcagg gttcggcgtt agtcccttt cgtatttctc     3360
tatcattggc ataaacacat cctgccaata ttcgtgttca aagttaactc tctcacaact    3420
ggaaatacct agatcgacct cgagggggg cccggtacca gtt                       3463
```

<210> SEQ ID NO 4
<211> LENGTH: 659
<212> TYPE: PRT
<213> ORGANISM: Candida RIM1
<220> FEATURE:
<221> NAME/KEY: MISC_FEATURE
<222> LOCATION: (43)..(43)
<223> OTHER INFORMATION: Amino acid 43 is "Xaa" wherein "Xaa" = any amino acid.

<400> SEQUENCE: 4

```
Met Asn Tyr Asn Ile His Pro Val Thr Tyr Leu Asn Ala Asp Ser Asn
1               5                   10                  15

Thr Gly Ala Ser Glu Ser Thr Ala Ser His His Gly Ser Lys Lys Ser
            20                  25                  30

Pro Ser Ser Asp Ile Asp Val Asp Asn Ala Xaa Ser Pro Ser Ser Phe
        35                  40                  45

Thr Ser Ser Gln Ser Pro His Ile Asn Ala Met Gly Asn Ser Pro His
    50                  55                  60

Ser Ser Phe Thr Ser Gln Ser Ala Ala Asn Ser Pro Ile Thr Asp Ala
65                  70                  75                  80

Lys Gln His Leu Val Lys Pro Thr Thr Lys Pro Ala Ala Phe Ala
                85                  90                  95

Pro Ser Ala Asn Gln Ser Asn Thr Thr Ala Pro Gln Ser Tyr Thr Gln
            100                 105                 110

Pro Ala Gln Gln Leu Pro Thr Gln Leu His Pro Ser Leu Asn Gln Ala
        115                 120                 125

Tyr Asn Asn Gln Pro Ser Tyr Tyr Leu His Gln Pro Thr Tyr Gly Tyr
    130                 135                 140

Gln Gln Gln Gln Gln Gln Gln Gln His Gln Glu Phe Asn Gln Pro Ser
```

```
                145                 150                 155                 160
Gln Gln Tyr His Asp His His Gly Tyr Tyr Ser Asn Asn Asn Ile Leu
                    165                 170                 175

Asn Gln Asn Gln Pro Ala Pro Gln Gln Asn Pro Val Lys Pro Phe Lys
                180                 185                 190

Lys Thr Tyr Lys Lys Ile Arg Asp Glu Asp Leu Lys Gly Pro Phe Lys
                195                 200                 205

Cys Leu Trp Ser Asn Cys Ser Ile Ile Phe Glu Thr Pro Glu Ile Leu
            210                 215                 220

Tyr Asp His Leu Cys Asp Asp His Val Gly Arg Lys Ser Ser Asn Asn
225                 230                 235                 240

Leu Ser Leu Thr Cys Leu Trp Glu Asn Cys Gly Thr Thr Val Lys
            245                 250                 255

Arg Asp His Ile Thr Ser His Leu Arg Val His Val Pro Leu Lys Pro
                260                 265                 270

Phe His Cys Asp Leu Cys Pro Lys Ser Phe Lys Arg Pro Gln Asp Leu
                275                 280                 285

Lys Lys His Ser Lys Thr His Ala Glu Asp His Pro Lys Lys Leu Lys
            290                 295                 300

Lys Ala Gln Arg Glu Leu Met Lys Gln Gln Lys Glu Ala Lys Gln
305                 310                 315                 320

Gln Gln Lys Leu Ala Asn Lys Arg Ala Asn Ser Met Asn Ala Thr Thr
                325                 330                 335

Ala Ser Asp Leu Gln Leu Asn Tyr Tyr Ser Gly Asn Pro Ala Asp Gly
                340                 345                 350

Leu Asn Tyr Asp Asp Thr Ser Lys Lys Arg Arg Tyr Glu Asn Asn Ser
            355                 360                 365

Gln His Asn Met Tyr Val Val Asn Ser Ile Leu Asn Asp Phe Asn Phe
            370                 375                 380

Gln Gln Met Ala Gln Ala Pro Gln Gln Pro Gly Val Val Gly Thr Ala
385                 390                 395                 400

Gly Ser Ala Glu Phe Thr Thr Lys Arg Met Lys Ala Gly Thr Glu Tyr
                405                 410                 415

Asn Ile Asp Val Phe Asn Lys Leu Asn His Leu Asp Asp His Leu His
                420                 425                 430

His His His Pro Gln Gln Gln His Pro Gln Gln Gln Tyr Gly Gly Asn
            435                 440                 445

Ile Tyr Glu Ala Glu Lys Phe Phe Asn Ser Leu Ser Asn Ser Ile Asp
    450                 455                 460

Met Gln Tyr Gln Asn Met Ser Thr Gln Tyr Gln Gln His Ala Gly
465                 470                 475                 480

Ser Thr Phe Ala Gln Gln Lys Pro Thr Gln Gln Ala Ser Gly Gln Leu
                485                 490                 495

Tyr Pro Ser Leu Pro Thr Ile Gly Asn Gly Ser Tyr Thr Ser Gly Ser
                500                 505                 510

Ser His Lys Glu Gly Leu Val Asn Asn His Asn Gly Tyr Leu Pro Ser
            515                 520                 525

Tyr Pro Gln Ile Asn Arg Ser Leu Pro Tyr Ser Ser Gly Val Ala Gln
                530                 535                 540

Gln Pro Pro Ser Ala Leu Glu Phe Gly Gly Val Ser Thr Tyr Gln Lys
545                 550                 555                 560

Ser Ala Gln Ser Tyr Glu Glu Asp Ser Ser Asp Ser Ser Glu Glu Asp
                565                 570                 575
```

-continued

```
Asp Tyr Ser Thr Ser Ser Glu Asp Glu Leu Asp Thr Leu Phe Asp Lys
            580                 585                 590
Leu Asn Ile Asp Asp Asn Lys Val Glu Val Thr Ile Asp Gly Phe
        595                 600                 605
Asn Leu Lys Asp Val Ala Lys His Arg Glu Met Ile His Ala Val Leu
        610                 615                 620
Gly Tyr Leu Arg Asn Gln Ile Glu Gln Gln Glu Lys Glu Lys Ser Lys
625                 630                 635                 640
Glu Gln Lys Glu Val Asp Val Asn Glu Thr Lys Leu Tyr Pro Thr Ile
                645                 650                 655
Thr Ala Phe

<210> SEQ ID NO 5
<211> LENGTH: 4792
<212> TYPE: DNA
<213> ORGANISM: Saccharomyces cerevisiae INV9

<400> SEQUENCE: 5
cccagtttct cataacccgt catttgagcg attgctagtt gaaactatat acagctagtt      60
agtaagattt taaagacga aaagaacgga aagtaggaca actaccaaaa aaaaagatgg      120
aaggtttctt tggttagtta gcagtatccg cgtaatgcct tagacgtttt tgatcagaaa    180
aaaataaaac ttgatttcgc ccaggatcga actggggacg ttctgcgtgt taagcagatg    240
ccataaccga ctagaccacg aaaccagttt tttgatgttt cgtttaggac aagagtccta    300
tgagagtcca ctaaaattct aaaaataatt gtatcaacaa ccgtcatgca gctgttgtat    360
caagaatcga ccaccatcta tagactattg ttcatagctg tattacaata tcatataaga    420
tgtaaggata gaacgtgaag atcgagaaac agtcagcaga tttaatggaa gctgaaatgc    480
acggattgat aatgtaatag aataagtgac aacataagaa atgaaagaaa aaaaataaca    540
ttaatataat ttagaaatgt tagtttcctt ctatgaactc tcgtatccct ggggaggact    600
ttcaatatat tcagtatacc taccgttcaa atgatactct aaaatatcat ctattaagtg    660
gtattcaggt tttccccacg caagattgag tgcgtcaggc aaagccacga tcgcagatta    720
ctctcctaac aatattaaga tcgtcaagaa catccggttt tactcaagcg cttaatacaa    780
cacgtcggct ttcgctcaac tgcagtatat tgtgtctgta acctctcccg tcaagtttgc    840
gccacgggcc caataaccaa cttctgcgcc attgttacgg aaaagtggcc atctttgcta    900
tgctcgtaag gctagcgctc tctaagtacg ccagcccaaa aactccgtat cgctcttcat    960
cggaattgct atatctacag ccggacgggc actctatgta tactcatatc acagccactg   1020
ttgcactaca ttattcgcag ggactccgag atcgctgagc atgttgctaa gcaacttacc   1080
aaggttggaa tgcattatat agtccgatat agacccgct cggactatat tatataaatt    1140
caaatagcac tttcaacgag tgtcttaatc cgtcctagtt cctgctctcg ctccacgttg   1200
tcatcccacc cattcgcacg ggtcttctgt gcgaatgagc cacaacgggg ccgagttcag   1260
gccgtgtccg cctacaacgt ccgccaacta gtggcaattg ctacgtacgc cgaccacgct   1320
gacacgcacc gttctactcg ctctatgctg cggtgtgacg tgtgaacgcg cgatcgttcg   1380
caatcgtatc gtttgccaag aaaaaaagcc aatcggagaa tctgaaaatc gctattcggc   1440
ttgcaggtcg cacgcactca gagtacgaaa tgccaagtac cggaatttcc ttggccttt   1500
ttaagttct tctcttctat tctttttccc ctttcttttc tcctttgcta tctgtctggt   1560
ttaaataaac atagtatttt tttgtgtcta agcctcttcc tcttctctcg tacttgctct   1620
```

```
actaccactt tacttaatcg cctttctttg ttttctttct tcgttatttg ttcttggaac    1680
ttttccgctc caatcccaac gattggcttc aaaacacgtt ctactgtcta gcaatttctg    1740
caggtgccat ttttcttagg cttataccct ttccttttcc ccttacattt gatttcttct    1800
tcaaagttcc ttatagtatt attgtctaag ctctattgag tcaaaagtaa caatctagac    1860
gaaggaaaaa aaaaaaatag aaaatagaca tccccgaata cgcatcatct cacgcacgta    1920
caagatttta acgttaaagc caaagtacgc tagtatagta tcatcagcat caccctcact    1980
atcggtagca ttgaccaaac atgtcgttac tgagactgtg gaacaaagaa tcaagggcac    2040
catcaaaaat aaagagtcat ggtattgttg gcagttacgg caacagcatg ctggcccata    2100
acaacgtgaa gcaatttcgt atagacatag acgaaccgca tagagtatgg aaaccgaatg    2160
aaagcataac cggagaagcg gtcattgaca taaagagaga cataactaac gtagcgatca    2220
aattatcgct agtatgtgag gttcgcgtga aaacggggaa cagtccaacc tccaagaata    2280
agagaattga gaaaacctta gagaagtcga cgtttcttta tggacaggac tacgtaaaga    2340 cagcttttt  ggctaaggaa aagaaaccgc atgttgacaa aaccaccatt ctcaatggtt    2400
taagcaaggg ggaacacagg tttcccttta ggatacgaat accacgaggc agaggaatgt    2460
tgagctctat aaagttcgaa aggggctcga taacatactt cctctcttgc actttagaat    2520
ccctcaacaa catcaacgga ttaaaaaaac cggaagcaag atgcgaacgt gagtttgcag    2580
tcatagttcc gctggacgtc tcgaggctgc ccaagccgaa aactaagaca gtggttttac    2640
aatcagcatc tatggtccaa acaaaaaga acaaatctac agaggacgaa tcctcatcgt    2700
atacacaatt aactcaaaag tctactactt ctaattcttc tagcagttca gtaaactcca    2760
agacgtcccc cttaccaaat aaaacggtga ctatatccgt agacataccg caggctggat    2820
tcatgattgg tgaaattatc cctatagacg ttaagattga ccactataag cctttctatg    2880
ccctgcgggg tctcaccacc actttggtga ggatatgtag ggtgggcggt gcaggcaaag    2940
atgatcctat ggagactttc agaaaagata tatgtcagag tatctctcct atatatatta    3000
accctgaaac gttgcagttt caatctagag tttatctgaa agtgcccctt gatgcatttt    3060
cgacccttac tactgtggga aaatttttct ccttccaata ctatatcgag ttatggttta    3120
acttatcaaa aaaaacgtg gtttacacag aatctaatag aataatagga actcctattg    3180
gagaacaaaa tggcttgggc gtagagaata atatcaaccg tatccaaagg aaaatgctac    3240
gtatggtcaa tccagaaacg ttggagaacg attctgaggg ttatgaatcc agtatatttt    3300
tcaaagatat ggtaaatgtg gaaaagctaa agagactgag gaatgtaact ggtatgtcca    3360
tagaaaccgt cataggaacg acgagatccg aacagcagca atctgatgca agcatcccat    3420
cccaatcctc aatcacggct cctcaaaatt ctccatcgaa tttaagagat tggttggccc    3480
cattaaatgc atatgatagt gacgatgttc cagttccaaa gtattcgcca aatgataaag    3540
tcagtgtacc gtcggaagac aaacaagaac ttgaacaaaa aagactacaa cagttagaaa    3600
gcgatcctcc cccttgtgat gactattaaa aagtgcaggt aacaagtcat atactcgcag    3660
cttgcgccgt gttggaacta ggcgccttaa tcatgtttgc atatttccac tatcccagcc    3720
acgtaatgat ccatgacatt aacatagaaa aaaaaaatcg aagcatgcac aaacctgaga    3780
tttatatatg ttcatgtgta cttaatatac gtttaatgat taaaactata gccgtcctca    3840
ggcaaactga gataagaaac gaaaaaatag cagtaacgta aacgttattc tatatttata    3900
aagacgtcaa aaaaaaaagt gattgtgata ttgagatgta agctatatac cgaactttga    3960
```

-continued

```
gctccctcac gtggaaaata tgatagattg ttgcctcatc attgcggaac cgcattttt    4020 ttttgtattt ttgcctccct agtttcaaaa tgcaccaaat tctcccctta atgcttttg    4080 ttttaagtcc caaatagcca tcctttcatc atcgggcaag atagaaattt gactgtcatt   4140
cagttgtaac acctgtttca gtagttcttt ctgtttgtta agcacagctg gatccaccac   4200
ctcgttcacg ctattgttat tcgtagccga tgcctcttct tgcggcctgg aagctaacgg   4260
gatcaaatca tccactttac atatcccatt cgttagcaat aattcagccg taacaaaact   4320
caactgtgga cacagctcta atagcgaaac agcatcttca ggatgcgctc ttgtccattc   4380
ttggaatttt tgtaaaaatt tcaactgcac ctctttcggt tttttagcta gttcgctcga   4440
tatcatcata gcagggtgg tcatgtttat gttaacgtcg ataccagagg gcaattctgg    4500
aaacttttga cttagaaaat tggcatttcc gctgttttga aagtccggcc cattactatt   4560
attattatta tttccattgt tgttattgtt cccattaatg ttgttgtact gttgttgttg   4620
ctgttgtgaa actcccgata tatcactatt gctggagtaa ccgcatttca aaaacctaga   4680
gcctaattgg tatccattca aattacgtac tgcgctggca ctggactcta aatctctaaa   4740
ttcaataaac gcgtaccctt tcgacctacc agtttggggg tcgaacatca tt           4792
```

<210> SEQ ID NO 6
<211> LENGTH: 542
<212> TYPE: PRT
<213> ORGANISM: Saccharomyces cerevisiae INV9

<400> SEQUENCE: 6

```
Met Ser Leu Leu Arg Leu Trp Asn Lys Glu Ser Arg Ala Pro Ser Lys
  1               5                  10                  15

Ile Lys Ser His Gly Ile Val Gly Ser Tyr Gly Asn Ser Met Leu Ala
                 20                  25                  30

His Asn Asn Val Lys Gln Phe Arg Ile Asp Ile Asp Glu Pro His Arg
             35                  40                  45

Val Trp Lys Pro Asn Glu Ser Ile Thr Gly Glu Ala Val Ile Asp Ile
         50                  55                  60

Lys Arg Asp Ile Thr Asn Val Ala Ile Lys Leu Ser Leu Val Cys Glu
 65                  70                  75                  80

Val Arg Val Lys Thr Gly Asn Ser Pro Thr Ser Lys Asn Lys Arg Ile
                 85                  90                  95

Glu Lys Thr Leu Glu Lys Ser Thr Phe Leu Tyr Gly Gln Asp Tyr Val
            100                 105                 110

Lys Thr Ala Phe Ser Ala Lys Glu Lys Lys Pro His Val Asp Lys Thr
        115                 120                 125

Thr Ile Leu Asn Gly Leu Ser Lys Gly Glu His Arg Phe Pro Phe Arg
    130                 135                 140

Ile Arg Ile Pro Arg Gly Arg Gly Met Leu Ser Ser Ile Lys Phe Glu
145                 150                 155                 160

Arg Gly Ser Ile Thr Tyr Phe Leu Ser Cys Thr Leu Glu Ser Leu Asn
                165                 170                 175

Asn Ile Asn Gly Leu Lys Lys Pro Glu Ala Arg Cys Glu Arg Glu Phe
            180                 185                 190

Ala Val Ile Val Pro Leu Asp Val Ser Arg Leu Pro Lys Pro Lys Thr
        195                 200                 205

Lys Thr Val Val Leu Gln Ser Ala Ser Met Val Gln Asn Lys Lys Asn
    210                 215                 220

Lys Ser Thr Glu Asp Glu Ser Ser Ser Tyr Thr Gln Leu Thr Gln Lys
```

```
                225                 230                 235                 240
Ser Thr Thr Ser Asn Ser Ser Ser Ser Val Asn Ser Lys Thr Ser
                245                 250                 255
Pro Leu Pro Asn Lys Thr Val Thr Ile Ser Val Asp Ile Pro Gln Ala
                260                 265                 270
Gly Phe Met Ile Gly Glu Ile Ile Pro Ile Asp Val Lys Ile Asp His
                275                 280                 285
Tyr Lys Pro Phe Tyr Ala Pro Ala Gly Leu Thr Thr Thr Leu Val Arg
                290                 295                 300
Ile Cys Arg Val Gly Gly Ala Gly Lys Asp Asp Pro Met Glu Thr Phe
305                 310                 315                 320
Arg Lys Asp Ile Cys Gln Ser Ile Ser Pro Ile Tyr Ile Asn Pro Glu
                325                 330                 335
Thr Leu Gln Phe Gln Ser Arg Val Tyr Leu Lys Val Pro Leu Asp Ala
                340                 345                 350
Phe Ser Thr Leu Thr Thr Val Gly Lys Phe Phe Ser Phe Gln Tyr Tyr
                355                 360                 365
Ile Glu Val Met Val Asn Leu Ser Lys Lys Asn Val Val Tyr Thr Glu
                370                 375                 380
Ser Asn Arg Ile Ile Gly Thr Pro Ile Gly Glu Gln Asn Gly Leu Gly
385                 390                 395                 400
Val Glu Asn Asn Ile Asn Arg Ile Gln Arg Lys Met Leu Arg Met Val
                405                 410                 415
Asn Pro Glu Thr Leu Glu Asn Asp Ser Glu Gly Tyr Glu Ser Ser Ile
                420                 425                 430
Phe Phe Lys Asp Met Val Asn Val Glu Lys Leu Lys Arg Leu Arg Asn
                435                 440                 445
Val Thr Gly Met Ser Ile Glu Thr Val Ile Gly Thr Thr Arg Ser Glu
                450                 455                 460
Gln Gln Gln Ser Asp Ala Ser Ile Pro Ser Gln Ser Ser Ile Thr Ala
465                 470                 475                 480
Pro Gln Asn Ser Pro Ser Asn Leu Arg Asp Trp Leu Ala Pro Leu Asn
                485                 490                 495
Ala Tyr Asp Ser Asp Asp Val Pro Val Pro Lys Tyr Ser Pro Asn Asp
                500                 505                 510
Lys Val Ser Val Pro Ser Glu Asp Lys Gln Glu Leu Glu Gln Lys Arg
                515                 520                 525
Leu Gln Gln Leu Glu Ser Asp Pro Pro Pro Cys Asp Asp Tyr
                530                 535                 540

<210> SEQ ID NO 7
<211> LENGTH: 29
<212> TYPE: DNA
<213> ORGANISM: Artificial Sequence
<220> FEATURE:
<223> OTHER INFORMATION: PCR primer

<400> SEQUENCE: 7
cgcacactat gcaaagaccg agatcttcc                                29

<210> SEQ ID NO 8
<211> LENGTH: 29
<212> TYPE: DNA
<213> ORGANISM: Artificial Sequence
<220> FEATURE:
<223> OTHER INFORMATION: PCR primer
```

<400> SEQUENCE: 8
gaagatcttc tccacatacc aatcactcg                29

<210> SEQ ID NO 9
<211> LENGTH: 40
<212> TYPE: DNA
<213> ORGANISM: Artificial Sequence
<220> FEATURE:
<223> OTHER INFORMATION: #1F primer

<400> SEQUENCE: 9
caagcattta cgttactgcg aaaatccata tacgcacact             40

<210> SEQ ID NO 10
<211> LENGTH: 40
<212> TYPE: DNA
<213> ORGANISM: Artificial Sequence
<220> FEATURE:
<223> OTHER INFORMATION: #1R primer

<400> SEQUENCE: 10
agtgtgcgta tatggatttt cgcagtaacg taaatgcttg             40

<210> SEQ ID NO 11
<211> LENGTH: 40
<212> TYPE: DNA
<213> ORGANISM: Artificial Sequence
<220> FEATURE:
<223> OTHER INFORMATION: #2F primer

<400> SEQUENCE: 11
tgatgaggta acctttacaa ctctcttcta gttcaagaac             40

<210> SEQ ID NO 12
<211> LENGTH: 40
<212> TYPE: DNA
<213> ORGANISM: Artificial Sequence
<220> FEATURE:
<223> OTHER INFORMATION: #2R primer

<400> SEQUENCE: 12
gttcttgaac tagaagagag ttgtaaaggt tacctcatca             40

<210> SEQ ID NO 13
<211> LENGTH: 40
<212> TYPE: DNA
<213> ORGANISM: Artificial Sequence
<220> FEATURE:
<223> OTHER INFORMATION: #3F primer

<400> SEQUENCE: 13
tttcaattca atggatttgg aatgtcatag agttaccaat             40

<210> SEQ ID NO 14
<211> LENGTH: 40
<212> TYPE: DNA
<213> ORGANISM: Artificial Sequence
<220> FEATURE:
<223> OTHER INFORMATION: #3R primer

<400> SEQUENCE: 14
attggtaact ctatgacatt ccaaatccat tgaattgaaa             40

<210> SEQ ID NO 15
<211> LENGTH: 40

-continued

```
<212> TYPE: DNA
<213> ORGANISM: Artificial Sequence
<220> FEATURE:
<223> OTHER INFORMATION: #4F primer

<400> SEQUENCE: 15
atttctgcct atactcttaa aggtattcgt ttgtttacta                    40

<210> SEQ ID NO 16
<211> LENGTH: 40
<212> TYPE: DNA
<213> ORGANISM: Artificial Sequence
<220> FEATURE:
<223> OTHER INFORMATION: #4R primer

<400> SEQUENCE: 16
tagtaaacaa acgaatacct ttaagagtat aggcagaaat                    40

<210> SEQ ID NO 17
<211> LENGTH: 40
<212> TYPE: DNA
<213> ORGANISM: Artificial Sequence
<220> FEATURE:
<223> OTHER INFORMATION: #5F primer

<400> SEQUENCE: 17
ttggggctaa gaatggacac agatcagtca ttcatgttgt                    40

<210> SEQ ID NO 18
<211> LENGTH: 40
<212> TYPE: DNA
<213> ORGANISM: Artificial Sequence
<220> FEATURE:
<223> OTHER INFORMATION: #5R primer

<400> SEQUENCE: 18
acaacatgaa tgactgatct gtgtccattc ttagccccaa                    40

<210> SEQ ID NO 19
<211> LENGTH: 40
<212> TYPE: DNA
<213> ORGANISM: Artificial Sequence
<220> FEATURE:
<223> OTHER INFORMATION: #6F primer

<400> SEQUENCE: 19
gggtgtgcct ggaaagttca ttcccttttc tttttctttg                    40

<210> SEQ ID NO 20
<211> LENGTH: 40
<212> TYPE: DNA
<213> ORGANISM: Artificial Sequence
<220> FEATURE:
<223> OTHER INFORMATION: #6R primer

<400> SEQUENCE: 20
caaagaaaaa gaaaagggaa tgaactttcc aggcacaccc                    40

<210> SEQ ID NO 21
<211> LENGTH: 40
<212> TYPE: DNA
<213> ORGANISM: Artificial Sequence
<220> FEATURE:
<223> OTHER INFORMATION: #7F primer

<400> SEQUENCE: 21
```
caaaacttta ggaataccgg aaattaaggt tttttcttc                                40

<210> SEQ ID NO 22
<211> LENGTH: 40
<212> TYPE: DNA
<213> ORGANISM: Artificial Sequence
<220> FEATURE:
<223> OTHER INFORMATION: #7R primer

<400> SEQUENCE: 22
gaagaaaaaa accttaattt ccggtattcc taaagttttg                                40

<210> SEQ ID NO 23
<211> LENGTH: 40
<212> TYPE: DNA
<213> ORGANISM: Artificial Sequence
<220> FEATURE:
<223> OTHER INFORMATION: #8F primer

<400> SEQUENCE: 23
cgaatgtgaa tgcgctaatc ttgtgtgcct acgccagccc                                40

<210> SEQ ID NO 24
<211> LENGTH: 40
<212> TYPE: DNA
<213> ORGANISM: Artificial Sequence
<220> FEATURE:
<223> OTHER INFORMATION: #8R primer

<400> SEQUENCE: 24
gggctggcgt aggcacacaa gattagcgca ttcacattcg                                40

<210> SEQ ID NO 25
<211> LENGTH: 40
<212> TYPE: DNA
<213> ORGANISM: Artificial Sequence
<220> FEATURE:
<223> OTHER INFORMATION: #9F primer

<400> SEQUENCE: 25
agacaaaaaa taggaaaagt ggtatttcca ccacatgaaa                                40

<210> SEQ ID NO 26
<211> LENGTH: 40
<212> TYPE: DNA
<213> ORGANISM: Artificial Sequence
<220> FEATURE:
<223> OTHER INFORMATION: #9R primer

<400> SEQUENCE: 26
tttcatgtgg tggaaatacc acttttccta tttttgtct                                 40

<210> SEQ ID NO 27
<211> LENGTH: 40
<212> TYPE: DNA
<213> ORGANISM: Artificial Sequence
<220> FEATURE:
<223> OTHER INFORMATION: #10F primer

<400> SEQUENCE: 27
ttagtgcgga atactttcct ttaattagtg atggttctca                                40

<210> SEQ ID NO 28
<211> LENGTH: 40
<212> TYPE: DNA
<213> ORGANISM: Artificial Sequence

```
<220> FEATURE:
<223> OTHER INFORMATION: #10R primer

<400> SEQUENCE: 28
tgagaaccat cactaattaa aggaaagtat tccgcactaa                              40

<210> SEQ ID NO 29
<211> LENGTH: 40
<212> TYPE: DNA
<213> ORGANISM: Artificial Sequence
<220> FEATURE:
<223> OTHER INFORMATION: #11F primer

<400> SEQUENCE: 29
cagtgctttc aacaccttt attctcatcg agagccgagc                               40

<210> SEQ ID NO 30
<211> LENGTH: 40
<212> TYPE: DNA
<213> ORGANISM: Artificial Sequence
<220> FEATURE:
<223> OTHER INFORMATION: #11R primer

<400> SEQUENCE: 30
gctcggctct cgatgagaat aaaaggtgtt gaaagcactg                              40

<210> SEQ ID NO 31
<211> LENGTH: 40
<212> TYPE: DNA
<213> ORGANISM: Artificial Sequence
<220> FEATURE:
<223> OTHER INFORMATION: #12F primer

<400> SEQUENCE: 31
gtagctgaaa agtccatcta catctgtgtg ccatgtcaga                              40

<210> SEQ ID NO 32
<211> LENGTH: 40
<212> TYPE: DNA
<213> ORGANISM: Artificial Sequence
<220> FEATURE:
<223> OTHER INFORMATION: #12R primer

<400> SEQUENCE: 32
tctgacatgg cacacagatg tagatggact tttcagctac                              40

<210> SEQ ID NO 33
<211> LENGTH: 40
<212> TYPE: DNA
<213> ORGANISM: Artificial Sequence
<220> FEATURE:
<223> OTHER INFORMATION: #13F primer

<400> SEQUENCE: 33
gagattatct tgggatctat tcgaattatg aatgatacta                              40

<210> SEQ ID NO 34
<211> LENGTH: 40
<212> TYPE: DNA
<213> ORGANISM: Artificial Sequence
<220> FEATURE:
<223> OTHER INFORMATION: #13R primer

<400> SEQUENCE: 34
tagtatcatt cataattcga atagatccca agataatctc                              40
```

<210> SEQ ID NO 35
<211> LENGTH: 40
<212> TYPE: DNA
<213> ORGANISM: Artificial Sequence
<220> FEATURE:
<223> OTHER INFORMATION: #14F primer

<400> SEQUENCE: 35
gttttggctc aatgggaccg ttcacaaatt tacggctaat           40

<210> SEQ ID NO 36
<211> LENGTH: 40
<212> TYPE: DNA
<213> ORGANISM: Artificial Sequence
<220> FEATURE:
<223> OTHER INFORMATION: #14R primer

<400> SEQUENCE: 36
attagccgta aatttgtgaa cggtcccatt gagccaaaac           40

<210> SEQ ID NO 37
<211> LENGTH: 70
<212> TYPE: DNA
<213> ORGANISM: Artificial Sequence
<220> FEATURE:
<223> OTHER INFORMATION: URA3 primer sequence

<400> SEQUENCE: 37
accacaacat gacgagggat aataactgat gaatagggtg ctttttatac tctgtgcggt           60
atttcacacc           70

<210> SEQ ID NO 38
<211> LENGTH: 70
<212> TYPE: DNA
<213> ORGANISM: Artificial Sequence
<220> FEATURE:
<223> OTHER INFORMATION: URA3 primer sequence

<400> SEQUENCE: 38
taaggagtcg taccgccaac taaatctgaa taacaatttg gctgctagaa gcagattgta           60
ctgagagtgc           70

<210> SEQ ID NO 39
<211> LENGTH: 29
<212> TYPE: DNA
<213> ORGANISM: Artificial Sequence
<220> FEATURE:
<223> OTHER INFORMATION: #1R primer

<400> SEQUENCE: 39
ccgctcgaga gtgtgcgtat atggattt           29

<210> SEQ ID NO 40
<211> LENGTH: 29
<212> TYPE: DNA
<213> ORGANISM: Artificial Sequence
<220> FEATURE:
<223> OTHER INFORMATION: #2F primer

<400> SEQUENCE: 40
ccgctcgagt gatgaggtaa cctttacaa           29

<210> SEQ ID NO 41
<211> LENGTH: 29

```
<212> TYPE: DNA
<213> ORGANISM: Artificial Sequence
<220> FEATURE:
<223> OTHER INFORMATION: #2R primer

<400> SEQUENCE: 41
ccgctcgagg ttcttgaact agaagagag                                29

<210> SEQ ID NO 42
<211> LENGTH: 29
<212> TYPE: DNA
<213> ORGANISM: Artificial Sequence
<220> FEATURE:
<223> OTHER INFORMATION: #3F primer

<400> SEQUENCE: 42
ccgctcgagt ttcaattcaa tggatttgg                                29

<210> SEQ ID NO 43
<211> LENGTH: 29
<212> TYPE: DNA
<213> ORGANISM: Artificial Sequence
<220> FEATURE:
<223> OTHER INFORMATION: #3R primer

<400> SEQUENCE: 43
ccgctcgaga ttggtaactc tatgacatt                                29

<210> SEQ ID NO 44
<211> LENGTH: 29
<212> TYPE: DNA
<213> ORGANISM: Artificial Sequence
<220> FEATURE:
<223> OTHER INFORMATION: #4F primer

<400> SEQUENCE: 44
ccgctcgaga tttctgccta tactcttaa                                29

<210> SEQ ID NO 45
<211> LENGTH: 29
<212> TYPE: DNA
<213> ORGANISM: Artificial Sequence
<220> FEATURE:
<223> OTHER INFORMATION: #4R primer

<400> SEQUENCE: 45
ccgctcgagt agtaaacaaa cgaatacct                                29

<210> SEQ ID NO 46
<211> LENGTH: 29
<212> TYPE: DNA
<213> ORGANISM: Artificial Sequence
<220> FEATURE:
<223> OTHER INFORMATION: #5F primer

<400> SEQUENCE: 46
ccgctcgagt tggggctaag aatggactt                                29

<210> SEQ ID NO 47
<211> LENGTH: 29
<212> TYPE: DNA
<213> ORGANISM: Artificial Sequence
<220> FEATURE:
<223> OTHER INFORMATION: #5R primer

<400> SEQUENCE: 47
```

```
ccgctcgaga caacatgaat gactgatct                                        29
```

<210> SEQ ID NO 48
<211> LENGTH: 29
<212> TYPE: DNA
<213> ORGANISM: Artificial Sequence
<220> FEATURE:
<223> OTHER INFORMATION: #6F primer

<400> SEQUENCE: 48

```
ccgctcgagg ggtgtgcctg gaaagttca                                        29
```

<210> SEQ ID NO 49
<211> LENGTH: 29
<212> TYPE: DNA
<213> ORGANISM: Artificial Sequence
<220> FEATURE:
<223> OTHER INFORMATION: #6R primer

<400> SEQUENCE: 49

```
ccgctcgagc aaagaaaaag aaaagggaa                                        29
```

<210> SEQ ID NO 50
<211> LENGTH: 29
<212> TYPE: DNA
<213> ORGANISM: Artificial Sequence
<220> FEATURE:
<223> OTHER INFORMATION: #7F primer

<400> SEQUENCE: 50

```
ccgctcgagc aaaactttag gaataccgg                                        29
```

<210> SEQ ID NO 51
<211> LENGTH: 29
<212> TYPE: DNA
<213> ORGANISM: Artificial Sequence
<220> FEATURE:
<223> OTHER INFORMATION: #7R primer

<400> SEQUENCE: 51

```
ccgctcgagg aagaaaaaaa ccttaattt                                        29
```

<210> SEQ ID NO 52
<211> LENGTH: 29
<212> TYPE: DNA
<213> ORGANISM: Artificial Sequence
<220> FEATURE:
<223> OTHER INFORMATION: #8F primer

<400> SEQUENCE: 52

```
ccgctcgagc gaatgtgaat gcgctaatc                                        29
```

<210> SEQ ID NO 53
<211> LENGTH: 29
<212> TYPE: DNA
<213> ORGANISM: Artificial Sequence
<220> FEATURE:
<223> OTHER INFORMATION: #8R primer

<400> SEQUENCE: 53

```
ccgctcgagg ggctggcgta ggcacacaa                                        29
```

<210> SEQ ID NO 54
<211> LENGTH: 29
<212> TYPE: DNA
<213> ORGANISM: Artificial Sequence
<220> FEATURE:
<223> OTHER INFORMATION: #9F primer

<400> SEQUENCE: 54
ccgctcgaga gacaaaaaat aggaaaagt                                29

<210> SEQ ID NO 55
<211> LENGTH: 29
<212> TYPE: DNA
<213> ORGANISM: Artificial Sequence
<220> FEATURE:
<223> OTHER INFORMATION: #9R primer

<400> SEQUENCE: 55
ccgctcgagg tagcaggttt catgtggtg                                29

<210> SEQ ID NO 56
<211> LENGTH: 29
<212> TYPE: DNA
<213> ORGANISM: Artificial Sequence
<220> FEATURE:
<223> OTHER INFORMATION: #10F primer

<400> SEQUENCE: 56
ccgctcgagt tagtgcggaa tactttcct                                29

<210> SEQ ID NO 57
<211> LENGTH: 29
<212> TYPE: DNA
<213> ORGANISM: Artificial Sequence
<220> FEATURE:
<223> OTHER INFORMATION: #10R primer

<400> SEQUENCE: 57
ccgctcgagt gagaaccatc actaattaa                                29

<210> SEQ ID NO 58
<211> LENGTH: 29
<212> TYPE: DNA
<213> ORGANISM: Artificial Sequence
<220> FEATURE:
<223> OTHER INFORMATION: #11F primer

<400> SEQUENCE: 58
ccgctcgagc agtgctttca acaccttttt                               29

<210> SEQ ID NO 59
<211> LENGTH: 29
<212> TYPE: DNA
<213> ORGANISM: Artificial Sequence
<220> FEATURE:
<223> OTHER INFORMATION: #11R primer

<400> SEQUENCE: 59
ccgctcgagg ctcggctctc gatgagaat                                29

<210> SEQ ID NO 60
<211> LENGTH: 29
<212> TYPE: DNA
<213> ORGANISM: Artificial Sequence
<220> FEATURE:
<223> OTHER INFORMATION: #12F primer

<400> SEQUENCE: 60
ccgctcgagg tagctgaaaa gtccatcta                                29

<210> SEQ ID NO 61
<211> LENGTH: 29
<212> TYPE: DNA
<213> ORGANISM: Artificial Sequence
<220> FEATURE:
<223> OTHER INFORMATION: #12R primer

<400> SEQUENCE: 61
ccgctcgagt ctgacatggc acacagatg                               29

<210> SEQ ID NO 62
<211> LENGTH: 29
<212> TYPE: DNA
<213> ORGANISM: Artificial Sequence
<220> FEATURE:
<223> OTHER INFORMATION: #13F primer

<400> SEQUENCE: 62
ccgctcgagg agattatctt gggatctat                               29

<210> SEQ ID NO 63
<211> LENGTH: 29
<212> TYPE: DNA
<213> ORGANISM: Artificial Sequence
<220> FEATURE:
<223> OTHER INFORMATION: #13R primer

<400> SEQUENCE: 63
ccgctcgagt agtatcattc ataattcga                               29

<210> SEQ ID NO 64
<211> LENGTH: 29
<212> TYPE: DNA
<213> ORGANISM: Artificial Sequence
<220> FEATURE:
<223> OTHER INFORMATION: #14F primer

<400> SEQUENCE: 64
ccgctcgagg ttttggctca atgggaccg                               29

<210> SEQ ID NO 65
<211> LENGTH: 29
<212> TYPE: DNA
<213> ORGANISM: Artificial Sequence
<220> FEATURE:
<223> OTHER INFORMATION: #14R primer

<400> SEQUENCE: 65
ccgctcgaga ttagccgtaa atttgtgaa                               29

<210> SEQ ID NO 66
<211> LENGTH: 29
<212> TYPE: DNA
<213> ORGANISM: Artificial Sequence
<220> FEATURE:
<223> OTHER INFORMATION: #15F primer

<400> SEQUENCE: 66
ccgctcgagc tccacatacc aatcactcg                               29

<210> SEQ ID NO 67
<211> LENGTH: 29
<212> TYPE: DNA
<213> ORGANISM: Artificial Sequence
<220> FEATURE:
<223> OTHER INFORMATION: #15R primer

```
<400> SEQUENCE: 67
ccgctcgagt agttaaacgt tttattagc                                        29
```